(12) United States Patent
Cha et al.

(10) Patent No.: US 10,573,824 B2
(45) Date of Patent: Feb. 25, 2020

(54) COMPOUND AND ORGANIC ELECTRONIC ELEMENT COMPRISING SAME

(71) Applicant: LG Chem, Ltd., Seoul (KR)

(72) Inventors: Yongbum Cha, Daejeon (KR); Sung Kil Hong, Daejeon (KR); Kichul Koo, Daejeon (KR)

(73) Assignee: LG Chem, Ltd. (KR)

( * ) Notice: Subject to any disclaimer, the term of this patent is extended or adjusted under 35 U.S.C. 154(b) by 197 days.

(21) Appl. No.: 15/562,658

(22) PCT Filed: Sep. 23, 2016

(86) PCT No.: PCT/KR2016/010648
§ 371 (c)(1),
(2) Date: Sep. 28, 2017

(87) PCT Pub. No.: WO2017/052261
PCT Pub. Date: Mar. 30, 2017

(65) Prior Publication Data
US 2018/0090688 A1    Mar. 29, 2018

(30) Foreign Application Priority Data

Sep. 24, 2015    (KR) .................. 10-2015-0135770

(51) Int. Cl.
*H01L 51/50* (2006.01)
*H01L 51/00* (2006.01)
*C09K 11/06* (2006.01)
*C07D 209/80* (2006.01)

(52) U.S. Cl.
CPC ........ *H01L 51/0072* (2013.01); *C07D 209/80* (2013.01); *C09K 11/06* (2013.01); *C07B 2200/05* (2013.01)

(58) Field of Classification Search
None
See application file for complete search history.

(56) References Cited

U.S. PATENT DOCUMENTS

| 2004/0251816 | A1  | 12/2004 | Leo et al. |
| 2007/0018569 | A1* | 1/2007  | Kawamura ........... C07C 211/61 313/504 |
| 2008/0014464 | A1  | 1/2008  | Kawamura et al. |
| 2008/0124455 | A1* | 5/2008  | Shin .................... C07D 209/80 427/66 |
| 2009/0053557 | A1* | 2/2009  | Spindler ............. H01L 51/0058 428/690 |

(Continued)

FOREIGN PATENT DOCUMENTS

| CN | 101473464 A    | 7/2009 |
| KR | 20110084797 A  | 7/2011 |

(Continued)

OTHER PUBLICATIONS

Search report from International Application No. PCT/KR2016/010648, dated Jan. 23, 2017.

(Continued)

*Primary Examiner* — Gregory D Clark
(74) *Attorney, Agent, or Firm* — Lerner, David, Littenberg, Krumholz & Mentlik, LLP

(57) ABSTRACT

The present specification relates to a compound and an organic electronic device comprising the same.

17 Claims, 1 Drawing Sheet

(56) References Cited

U.S. PATENT DOCUMENTS

2014/0319472 A1* 10/2014 Cho ..................... H01L 51/006
257/40
2015/0318484 A1 11/2015 Buesing et al.
2016/0149140 A1 5/2016 Kang et al.

FOREIGN PATENT DOCUMENTS

| KR | 20140145428 A | 12/2014 |
| KR | 20150010016 A | 1/2015 |
| KR | 20150022461 A | 3/2015 |
| KR | 20150088295 A | 7/2015 |
| WO | 2003012890 A2 | 2/2003 |
| WO | 2014079527 A1 | 5/2014 |
| WO | 2015009076 A1 | 1/2015 |

OTHER PUBLICATIONS

Taiwanese Search Report for Application No. 105130781 dated May 22, 2018.

* cited by examiner

[Figure 1]
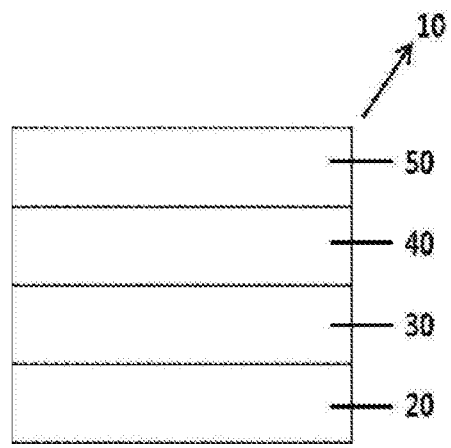
[Figure 2]
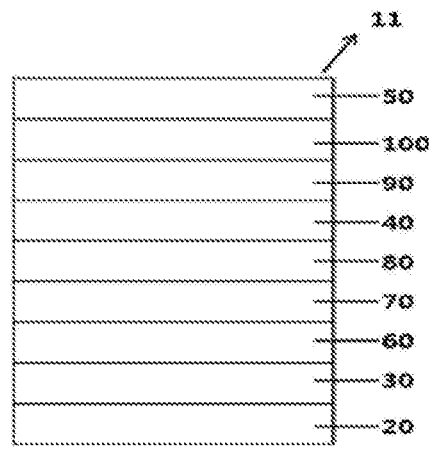

COMPOUND AND ORGANIC ELECTRONIC ELEMENT COMPRISING SAME

TECHNICAL FIELD

The present application is a national phase entry under 35 U.S. C. § 371 of International Application No. PCT/KR2016/010648, filed Sep. 23, 2016, published in Korean, which claims priority from Korean Patent Application No. 10-2015-0135770, filed in the Korean Intellectual Property Office on Sep. 24, 2015, the disclosures of which are incorporated herein by reference.

The present specification relates to a compound and an organic electronic device including the same.

BACKGROUND ART

Representative examples of an organic electronic device include an organic light emitting device. In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multi-layered structure composed of different materials in order to improve the efficiency and stability of an organic light emitting device in many cases, and for example, may be composed of a hole injection layer, a hole transport layer, a light emitting layer, an electron transport layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

International Publication No. 2003-012890

DISCLOSURE

Technical Problem

The present specification has been made in an effort to provide a compound and an organic electronic device comprising the same.

Technical Solution

The present specification provides a compound represented by the following Chemical Formula 1.

[Chemical Formula 1]

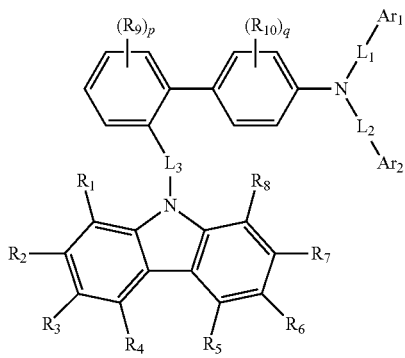

in Chemical Formula 1, $L_1$ to $L_3$ are the same as or different from each other, and are each independently a direct bond; or a substituted or unsubstituted arylene group, $Ar_1$ and $Ar_2$ are the same as or different from each other, and are each independently hydrogen; deuterium; a halogen group; a cyano group; a nitro group; a substituted or unsubstituted silyl group; a substituted or unsubstituted alkyl group; a substituted or unsubstituted cycloalkyl group; or a substituted or unsubstituted aryl group, $R_1$ to $R_8$ are the same as or different from each other, and are each independently hydrogen; deuterium; a halogen group; a cyano group; a substituted or unsubstituted alkyl group; or a substituted or unsubstituted aryl group, or may combine with an adjacent group to form a substituted or unsubstituted ring, $R_9$ and $R_{10}$ are the same as or different from each other, and are each independently hydrogen; deuterium; a halogen group; a cyano group; a substituted or unsubstituted alkyl group; or a substituted or unsubstituted aryl group, p and q are an integer of 1 to 4, when p is 2 or more, a plurality of $R_9$'s is the same as or different from each other, and when q is 2 or more, a plurality of $R_{10}$'s is the same as or different from each other.

Further, the present specification provides an organic electronic device including: a first electrode; a second electrode provided to face the first electrode; and one or more organic material layers provided between the first electrode and the second electrode, in which one or more layers of the organic material layers include the compound of Chemical Formula 1.

Advantageous Effects

The compound according to an exemplary embodiment of the present specification is used for an organic electronic device including an organic light emitting device, and thus may lower the driving voltage of the organic electronic device and improve the light efficiency, and enhance lifetime characteristics of the device by thermal stability of the compound.

DESCRIPTION OF DRAWINGS

FIG. 1 illustrates an organic light emitting device 10 according to an exemplary embodiment of the present specification.

FIG. 2 illustrates an organic light emitting device 11 according to another exemplary embodiment of the present specification.

MODE FOR INVENTION

Hereinafter, the present specification will be described in more detail.

The present specification provides the compound represented by Chemical Formula 1.

According to an exemplary embodiment of the present specification, the compound represented by Chemical Formula 1 has a structure where a carbazole is substituted at the ortho position in a benzene ring, and since the structure is in a state where the conjugation is broken as compared to a structure where the carbazole is substituted at the meta and para positions in the benzene ring, the compound has a structure where the HOMO and LUMO values are relatively easily adjusted depending on the type of substituent due to a large bandgap. Accordingly, when the compounds represented by Chemical Formula 1 are synthesized to perform a device evaluation on a hole injection layer, a hole transport layer, or an electron blocking layer, the driving voltage may be lowered and the light efficiency may be further improved in the organic electronic device.

In the present specification,

means a moiety to be linked.

Examples of the substituents in the present specification will be described below, but are not limited thereto.

The term "substitution" means that a hydrogen atom bonded to a carbon atom of a compound is changed into another substituent, and a position to be substituted is not limited as long as the position is a position at which the hydrogen atom is substituted, that is, a position at which the substituent may be substituted, and when two or more are substituted, the two or more substituents may be the same as or different from each other.

In the present specification, the term "substituted or unsubstituted" means being substituted with one or two or more substituents selected from the group consisting of deuterium; a halogen group; a cyano group; a nitro group; an imide group; an amino group; a silyl group; a boron group; a hydroxy group; a carbonyl group; an alkyl group; a cycloalkyl group; an alkenyl group; an alkoxy group; an aryloxy group; an alkylthioxy group; an arylthioxy group; an aryl group; an aralkyl group; an aralkenyl group; an alkylaryl group; a heteroaryl group; an amine group; an alkylamine group; an aralkylamine group; a heteroarylamine group; an arylamine group; a phosphoryl group; an arylphosphine group; a phosphine oxide group; or a heteroaryl group including one or more of N, O, S, Se, and Si atoms or being substituted with a substituent to which two or more substituents are linked among the exemplified substituents, or having no substituent. For example, "the substituent to which two or more substituents are linked" may be a biphenyl group. That is, the biphenyl group may also be an aryl group, and may be interpreted as a substituent to which two phenyl groups are linked. The biphenyl group means a substituent to which two aryl groups are linked, but "the substituent to which two or more substituents are linked" may also be a substituent to which two or more different substituents are linked. For example, "the substituent to which two or more substituents are linked" may be a phenyl group substituted with a pyridyl group, which is a substituent to which the pyridyl group and the phenyl group are linked, or a phenyl group substituted with a quinolinyl group, which is a substituent to which the quinolinyl group and the phenyl group are linked, or a phenyl group substituted with a cyano group, which is a substituent to which the cyano group and the phenyl group are linked.

In the present specification, examples of a halogen group include fluorine, chlorine, bromine or iodine.

In the present specification, an alkyl group may be straight-chained or branch-chained, and the number of carbon atoms thereof is not particularly limited, but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethylpropyl, isohexyl, 2-methylpentyl, 4-methylhexyl, 5-methylhexyl, and the like, but are not limited thereto.

In the present specification, a cycloalkyl group is not particularly limited, but a cycloalkyl group having 3 to 30 carbon atoms is preferred, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, specific examples of a silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, an aryl group is not particularly limited, but has preferably 6 to 30 carbon atoms, and the aryl group may be monocyclic or polycyclic.

When the aryl group is a monocyclic aryl group, the number of carbon atoms thereof is not particularly limited, but is preferably 6 to 30. Specific examples of the monocyclic aryl group include a phenyl group, a biphenyl group, a terphenyl group, and the like, but are not limited thereto.

When the aryl group is a polycyclic aryl group, the number of carbon atoms thereof is not particularly limited, but is preferably 10 to 30. Specific examples of the polycyclic aryl group include a naphthyl group, an anthracenyl group, a phenanthryl group, a triphenyl group, a pyrenyl group, a perylenyl group, a chrysenyl group, a fluorenyl group, and the like, but are not limited thereto.

In the present specification, the fluorenyl group may be substituted, and adjacent substituents may combine with each other to form a ring.

When the fluorenyl group is substituted, the fluorenyl group may be

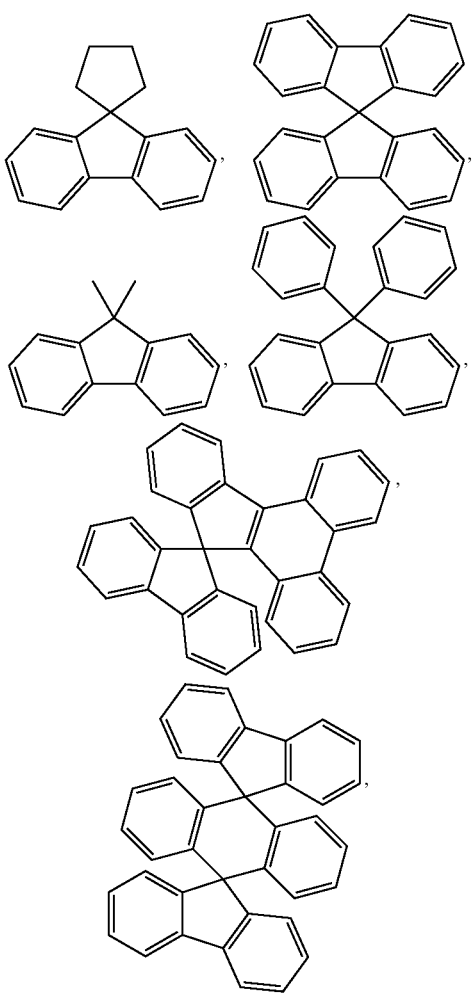

and the like. However, the fluorenyl group is not limited thereto.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, the case where adjacent groups combine with each other to form a ring means that adjacent groups combine with each other to form a 5-membered to 8-membered hydrocarbon ring or a 5-membered to 8-membered hetero ring as described above, and the ring may be monocyclic or polycyclic, may be an aliphatic ring, an aromatic ring, or a fused form thereof, and is not limited thereto.

In the present specification, a hydrocarbon ring may be an aromatic ring, an aliphatic ring, or a fused ring of the aromatic ring and the aliphatic ring, and may be selected from the examples of the cycloalkyl group or the aryl group, except for the hydrocarbon ring which is not monovalent.

In the present specification, an aromatic ring may be monocyclic or polycyclic, and may be selected from the examples of the aryl group, except for the aromatic ring which is not monovalent.

In the present specification, the above-described description on the aryl group may be applied to arylene except for a divalent arylene group.

According to an exemplary embodiment of the present specification, $L_1$ to $L_3$ are the same as or different from each other, and are each independently a direct bond; or a substituted or unsubstituted arylene group.

According to an exemplary embodiment of the present specification, $L_1$ to $L_3$ are a substituted or unsubstituted arylene group having 6 to 60 carbon atoms.

According to an exemplary embodiment of the present specification, $L_1$ to $L_3$ are the same as or different from each other, and are each independently a direct bond, or a substituted or unsubstituted phenylene group, a substituted or unsubstituted biphenylene group, a substituted or unsubstituted terphenylene group, a substituted or unsubstituted naphthylene group, a substituted or unsubstituted anthracenylene group, a substituted or unsubstituted phenanthrylene group, a substituted or unsubstituted triphenylene group, or a substituted or unsubstituted fluorenylene group.

According to an exemplary embodiment of the present specification, $L_1$ to $L_3$ are the same as or different from each other, and are each independently a direct bond, or a phenylene group, a biphenylene group, a terphenylene group, a naphthylene group, an anthracenylene group, a phenanthrylene group, a triphenylene group, or a fluorenylene group.

According to an exemplary embodiment of the present specification, $L_1$ to $L_3$ are the same as or different from each other, and are each independently a direct bond, or a phenylene group, a biphenylene group, a terphenylene group, a naphthylene group, an anthracenylene group, a phenanthrylene group, a triphenylene group, or a fluorenylene group, which is unsubstituted or substituted with deuterium, an alkyl group, a silyl group, a cyano group, or a halogen group.

According to an exemplary embodiment of the present specification, $L_1$ to $L_3$ are the same as or different from each other, and are each independently a direct bond, or a phenylene group or a biphenylene group, which is unsubstituted or substituted with deuterium, an alkyl group, a silyl group, a cyano group, or a halogen group.

According to an exemplary embodiment of the present specification, $L_1$ to $L_3$ are the same as or different from each other, and are each independently a direct bond, or a substituted or unsubstituted fluorenylene group.

According to an exemplary embodiment of the present specification, $L_1$ to $L_3$ are the same as or different from each other, and are each independently a direct bond, or a substituted or unsubstituted spirobifluorenylene group.

According to an exemplary embodiment of the present specification, $L_1$ to $L_3$ are the same as or different from each other, and are each independently a direct bond, or

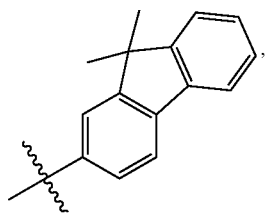

-continued

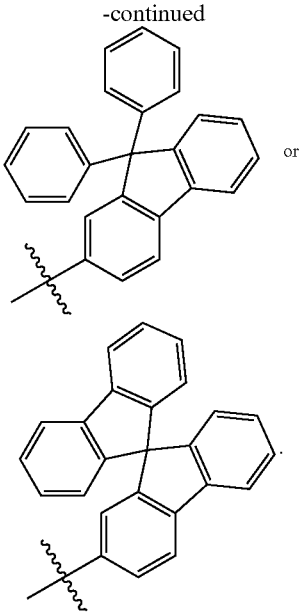

According to an exemplary embodiment of the present specification, Ar$_1$ and Ar$_2$ are the same as or different from each other, and are each independently hydrogen; deuterium; a halogen group; a cyano group; a nitrile group; a nitro group; a silyl group; a substituted or unsubstituted alkyl group; a substituted or unsubstituted cyclaoalkyl group; or a substituted or unsubstituted aryl group.

According to an exemplary embodiment of the present specification, Ar$_1$ and Ar$_2$ are an unsubstituted aryl group having 6 to 60 carbon atoms.

According to an exemplary embodiment of the present specification, Ar$_1$ and Ar$_2$ are the same as or different from each other, and are each independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthryl group, a substituted or unsubstituted triphenyl group, or a substituted or unsubstituted fluorenyl group.

According to an exemplary embodiment of the present specification, Ar$_1$ and Ar$_2$ are the same as or different from each other, and are each independently a phenyl group, a biphenyl group, a terphenyl group, a naphthyl group, an anthracenyl group, a phenanthryl group, a triphenyl group, or a fluorenyl group.

According to an exemplary embodiment of the present specification, Ar$_1$ and Ar$_2$ are the same as or different from each other, and are each independently a phenyl group, a biphenyl group, a terphenyl group, a naphthyl group, an anthracenyl group, a phenanthryl group, or a triphenyl group, which is unsubstituted or substituted with deuterium, an alkyl group, a silyl group, a cyano group, or a halogen group.

According to an exemplary embodiment of the present specification, Ar$_1$ and Ar$_2$ are the same as or different from each other, and are each independently a phenyl group or a biphenyl group, which is unsubstituted or substituted with deuterium, an alkyl group, a silyl group, a cyano group, or a halogen group.

According to an exemplary embodiment of the present specification, Ar$_1$ and Ar$_2$ are the same as or different from each other, and are each independently a substituted or unsubstituted triphenyl group.

According to an exemplary embodiment of the present specification, Ar$_1$ and Ar$_2$ are the same as or different from each other, and are each independently a substituted or unsubstituted fluorenyl group.

According to an exemplary embodiment of the present specification, Ar$_1$ and Ar$_2$ are the same as or different from each other, and are each independently a substituted or unsubstituted spirobifluorenyl group.

According to an exemplary embodiment of the present specification, Ar$_1$ and Ar$_2$ are the same as or different from each other, and are each independently

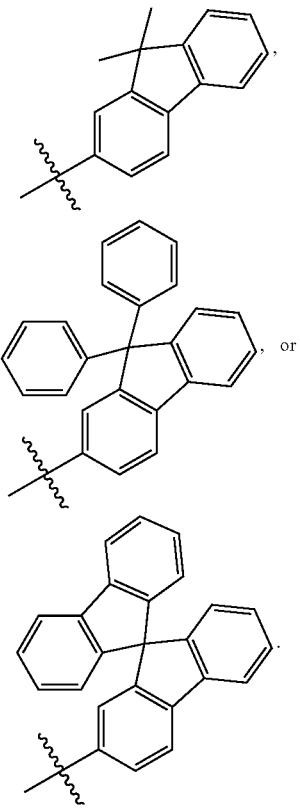

According to an exemplary embodiment of the present specification, R$_1$ to R$_8$ are the same as or different from each other, and are each independently hydrogen; deuterium; a halogen group; a cyano group; a substituted or unsubstituted alkyl group; or a substituted or unsubstituted aryl group, or combine with an adjacent group to form a substituted or unsubstituted ring.

According to an exemplary embodiment of the present specification, R$_1$ to R$_8$ are a substituted or unsubstituted aryl group having 6 to 20 carbon atoms.

According to an exemplary embodiment of the present specification, R$_1$ to R$_8$ are hydrogen.

According to an exemplary embodiment of the present specification, R$_1$ and R$_2$, R$_2$ and R$_3$, or R$_3$ and R$_4$ combine with each other to form a substituted or unsubstituted ring.

According to an exemplary embodiment of the present specification, R$_1$ and R$_2$, R$_2$ and R$_3$, or R$_3$ and R$_4$ combine with each other to form a substituted or unsubstituted aromatic hydrocarbon ring.

According to an exemplary embodiment of the present specification, $R_9$ and $R_{10}$ are the same as or different from each other, and are each independently hydrogen; deuterium; a halogen group; a cyano group; a substituted or unsubstituted alkyl group; or a substituted or unsubstituted aryl group.

According to an exemplary embodiment of the present specification, $R_9$ and $R_{10}$ are a substituted or unsubstituted alkyl group having 1 to 10 carbon atoms.

According to an exemplary embodiment of the present specification, $R_9$ and $R_{10}$ are hydrogen.

According to an exemplary embodiment of the present specification, p and q are an integer of 1 to 4.

According to an exemplary embodiment of the present specification, Chemical Formula 1 may be represented by any one of the following Chemical Formulae 2 to 4.

In Chemical Formulae 2 to 4, $L_1$ to $L_3$, $Ar_1$, $Ar_2$, $R_1$ to $R_{10}$, p, and q are the same as those defined in Chemical Formula 1, R' is hydrogen; deuterium; a halogen group; a cyano group; a substituted or unsubstituted alkyl group; or a substituted or unsubstituted aryl group, r is an integer of 1 to 4, and when r is 2 or more, a plurality of R's is the same as or different from each other.

According to an exemplary embodiment of the present specification, the compound represented by Chemical Formula 1 is represented by any one of the following compounds.

[Chemical Formula 2]

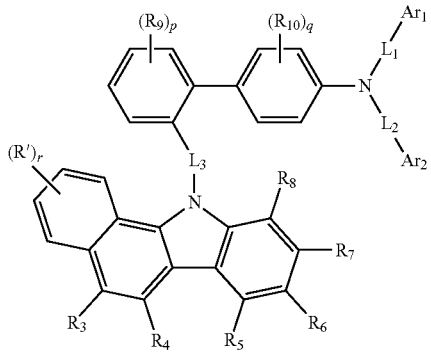

[Chemical Formula 3]

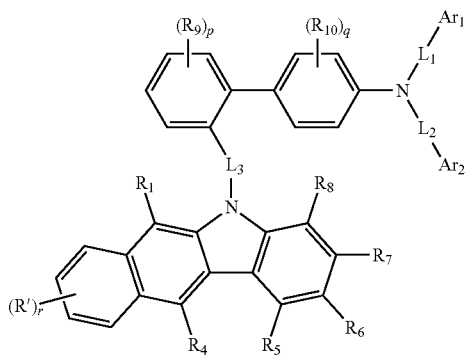

[Chemical Formula 4]

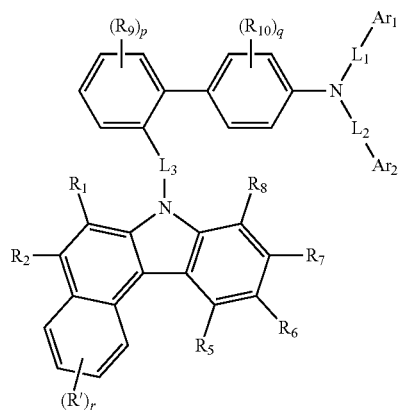

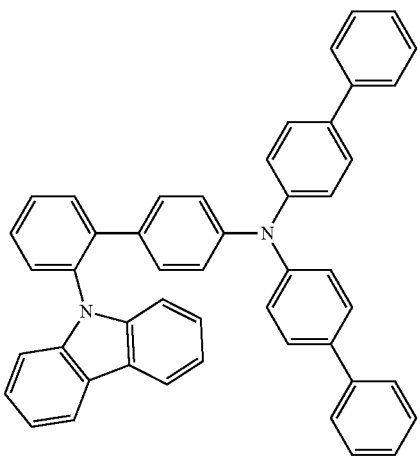

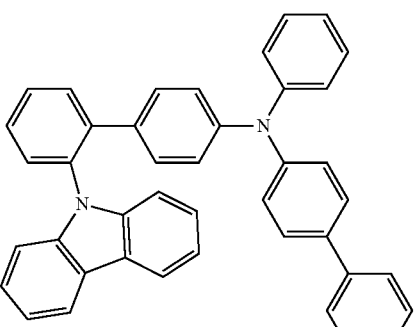

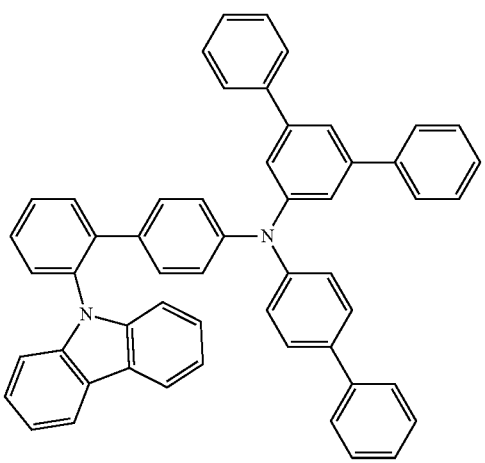

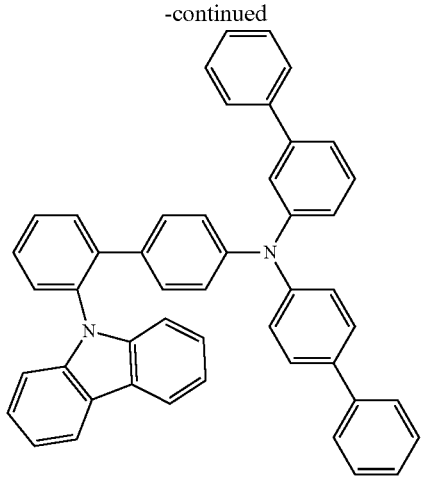
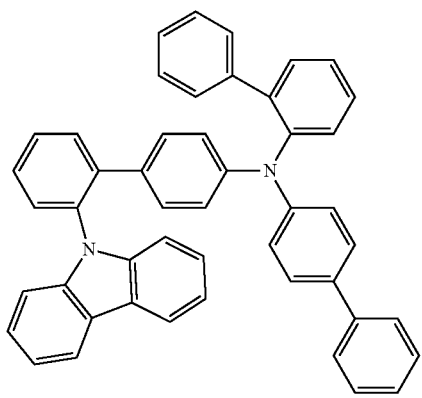
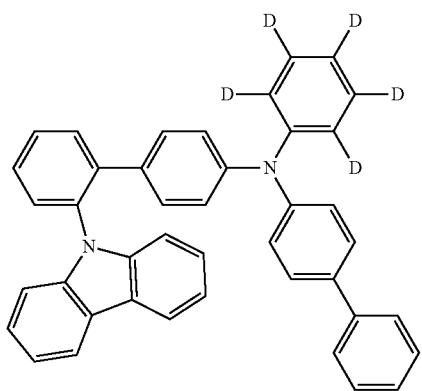
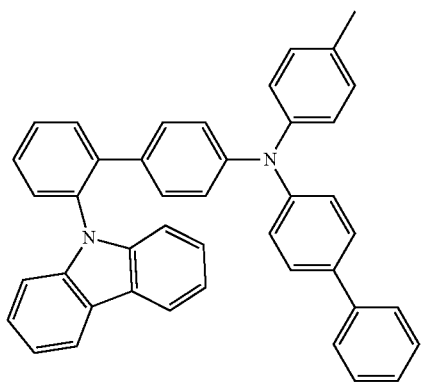
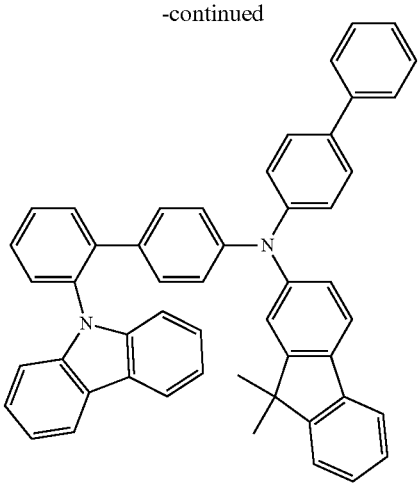
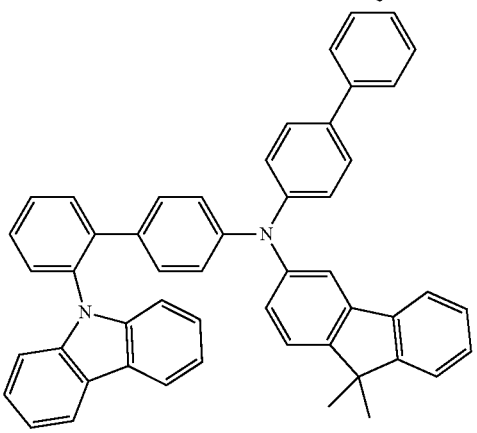
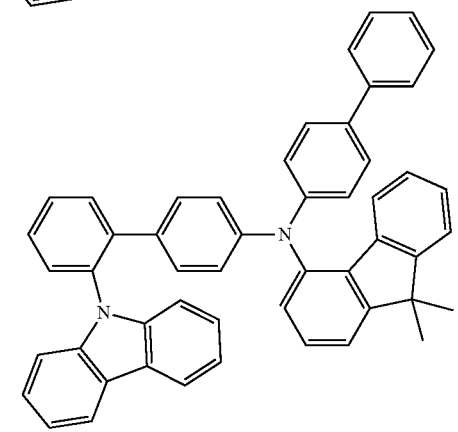
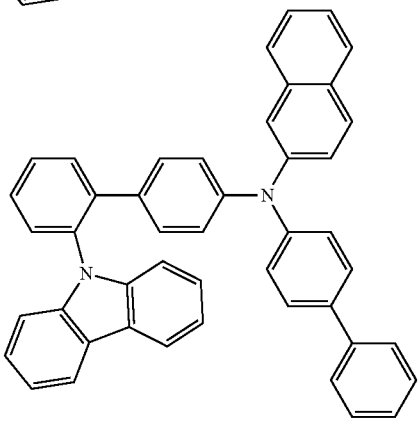

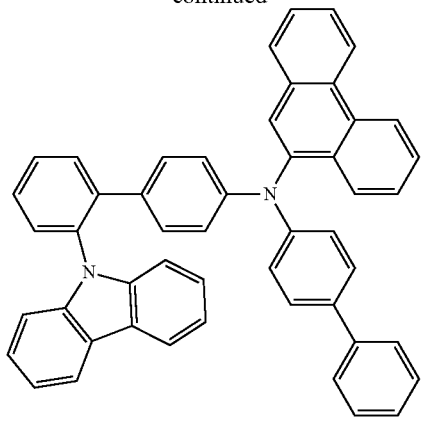
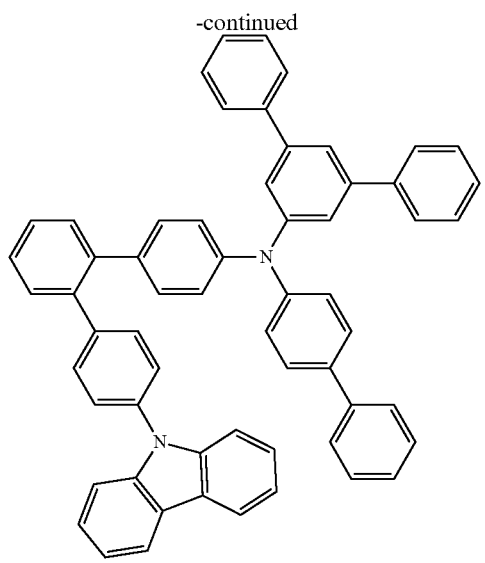
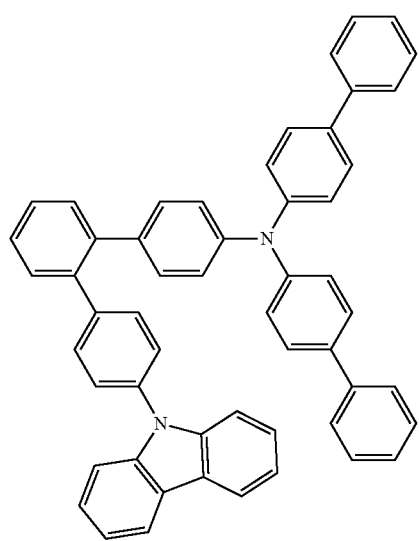
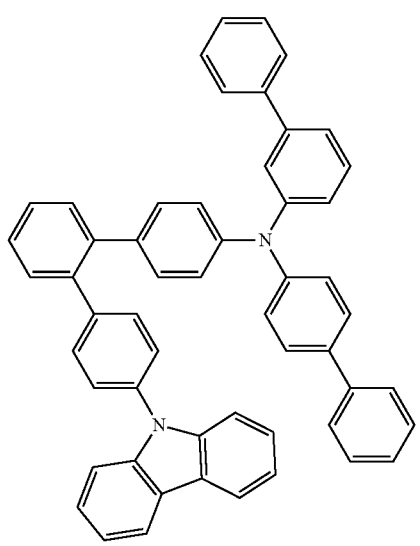
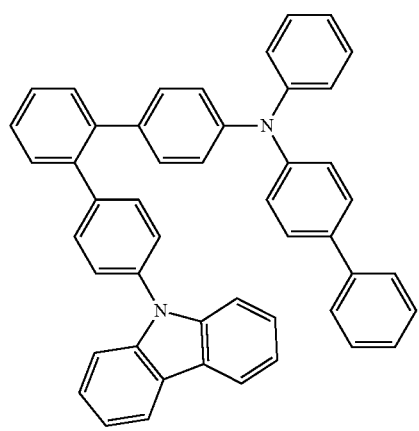
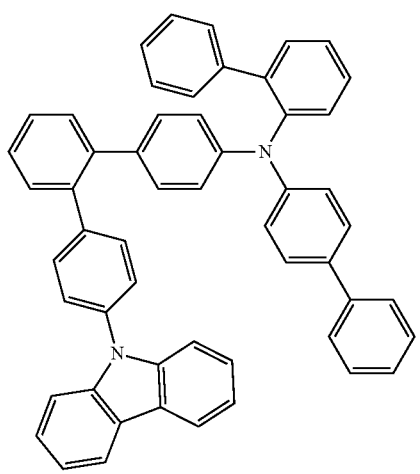

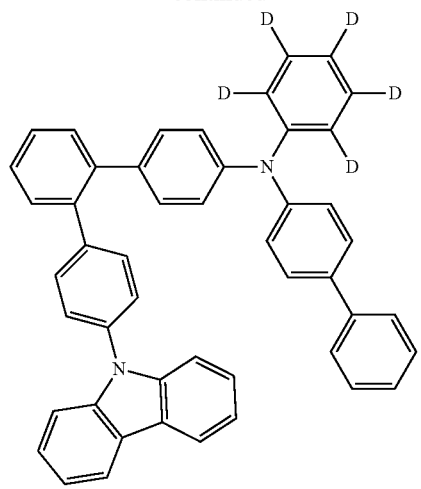
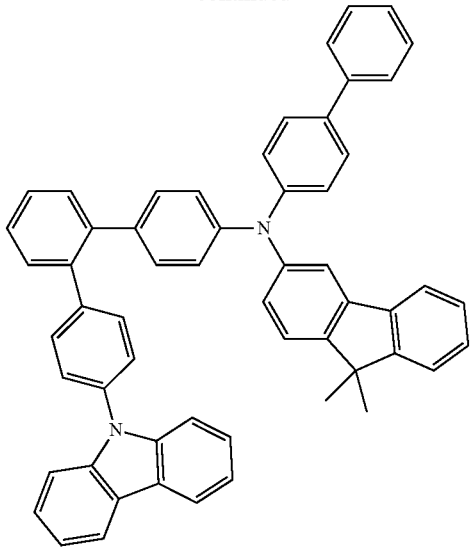
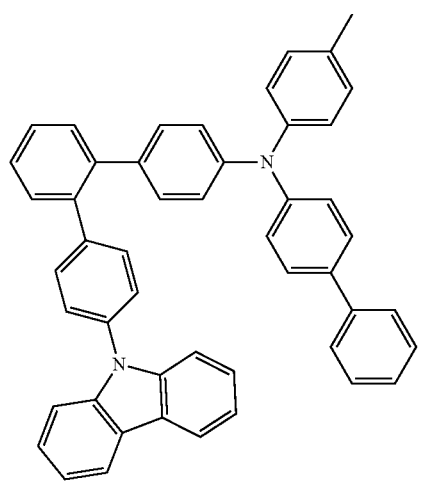
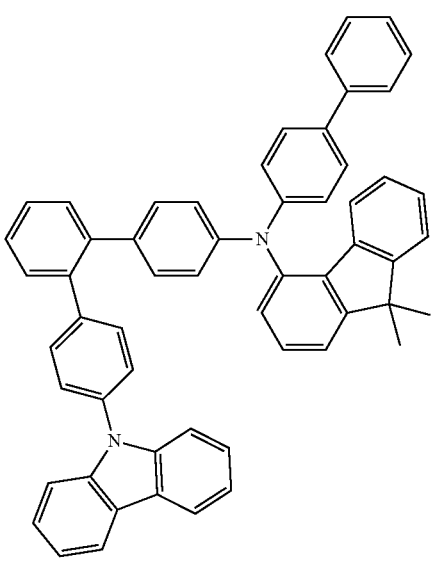
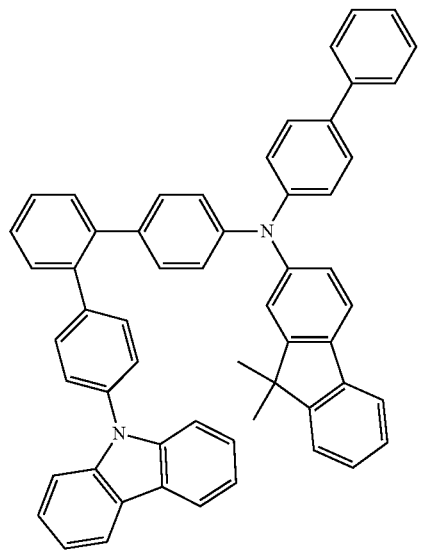
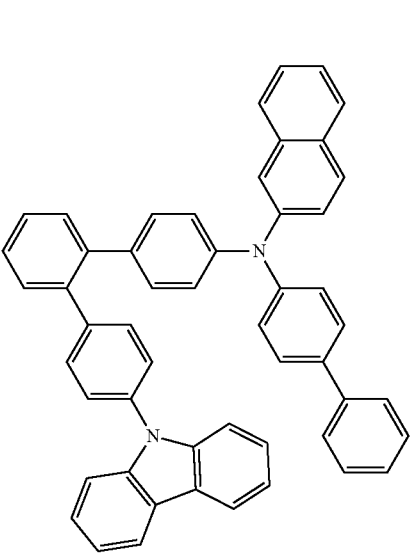

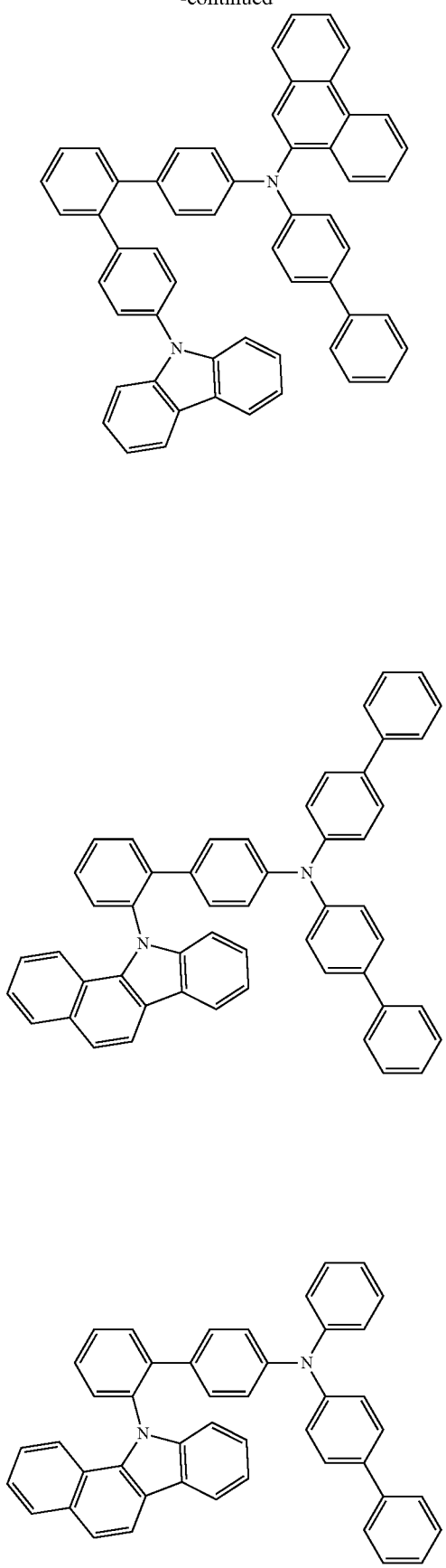
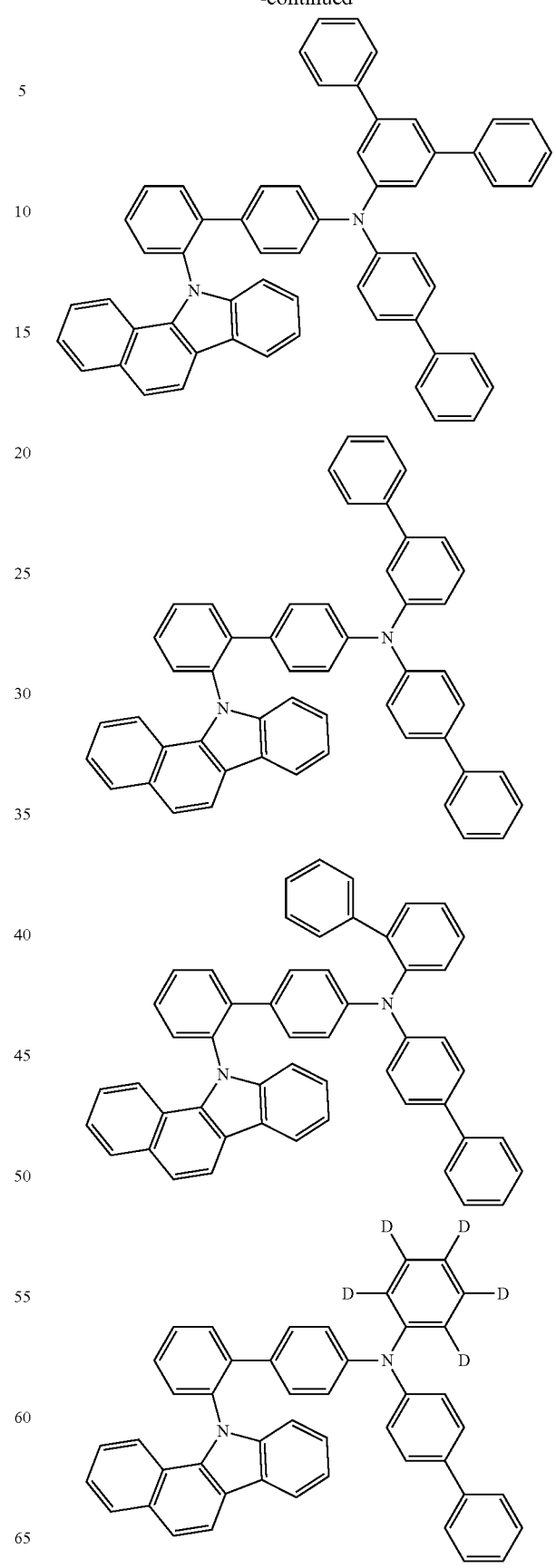

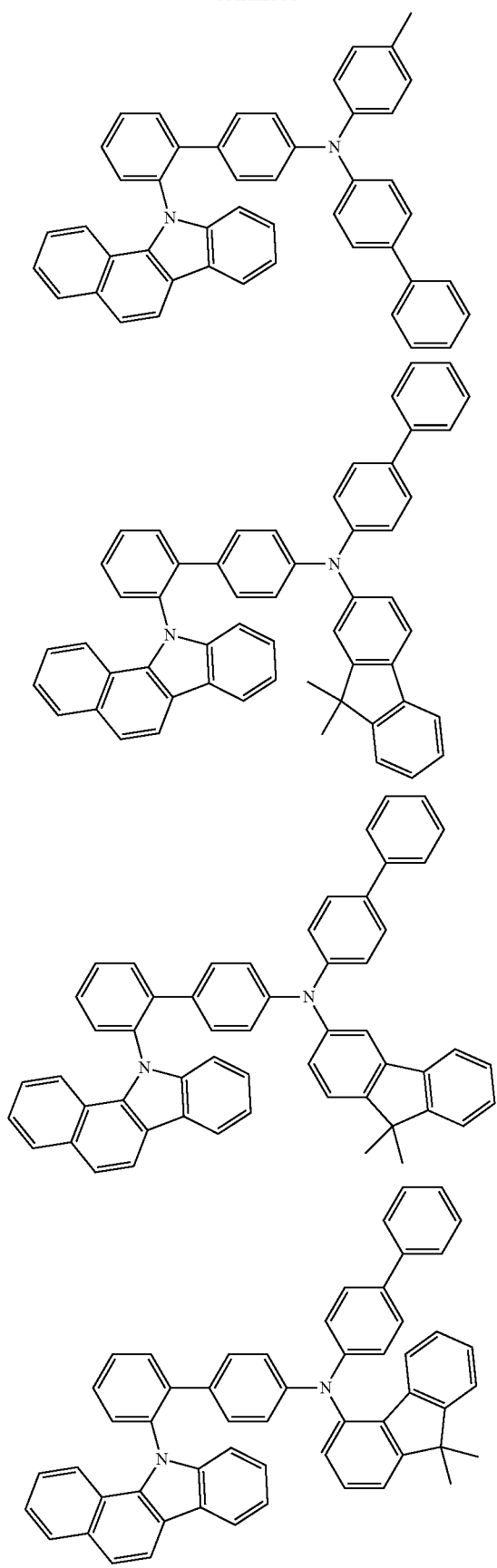
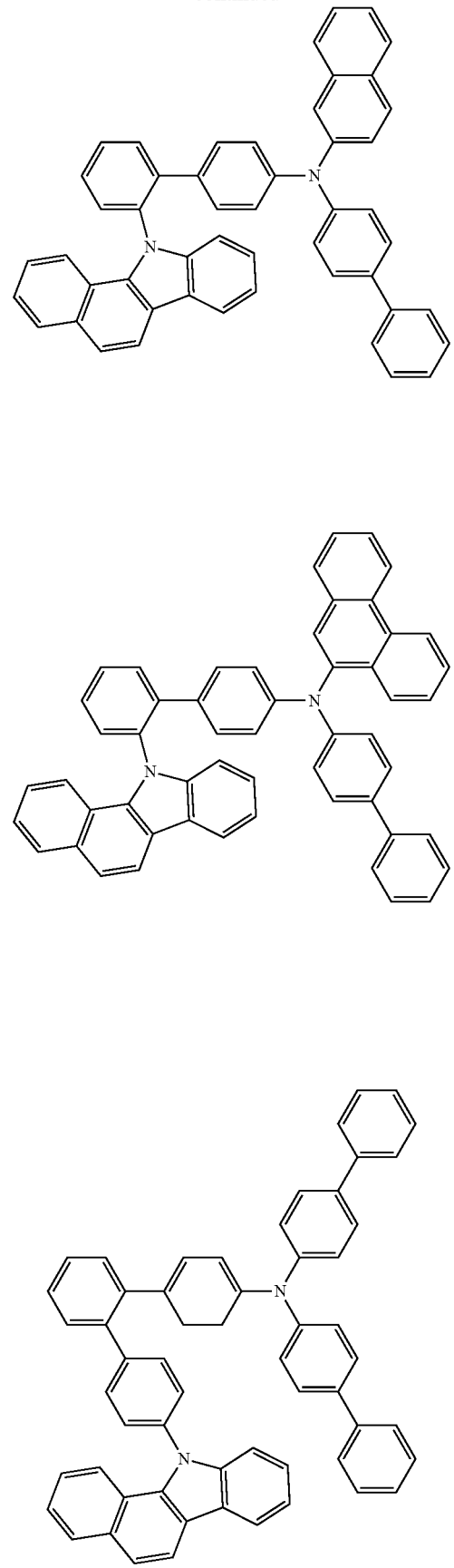

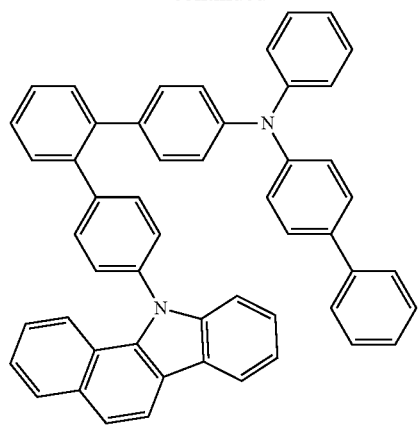
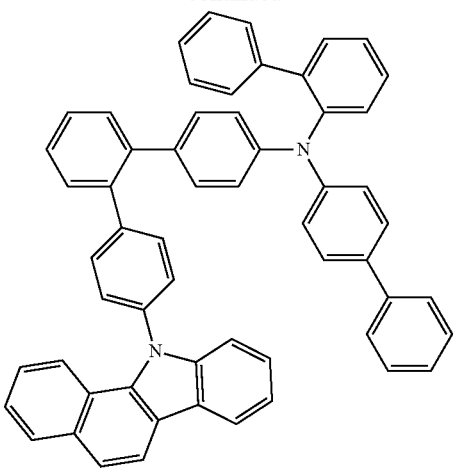
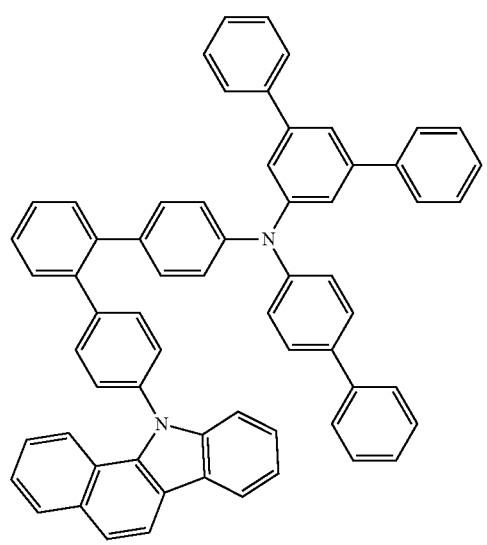
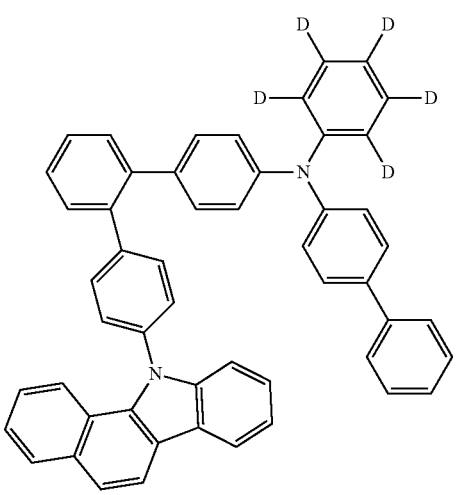
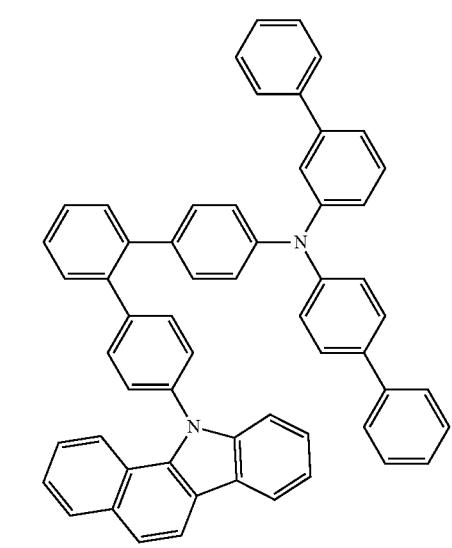
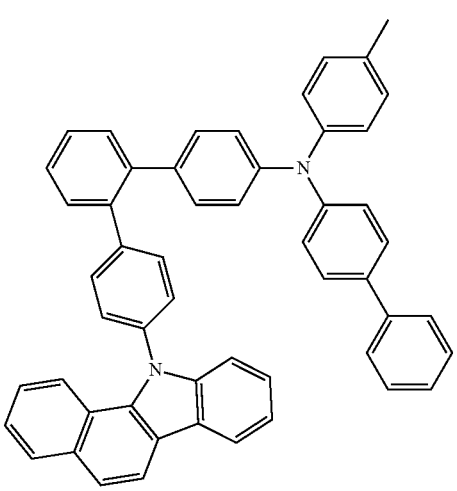

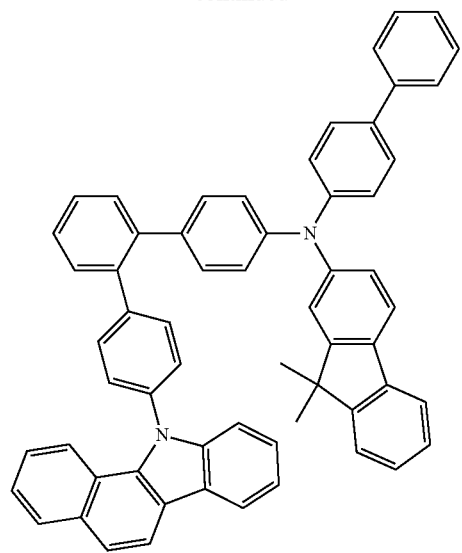
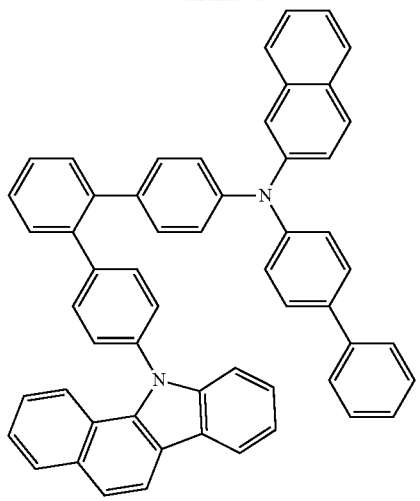
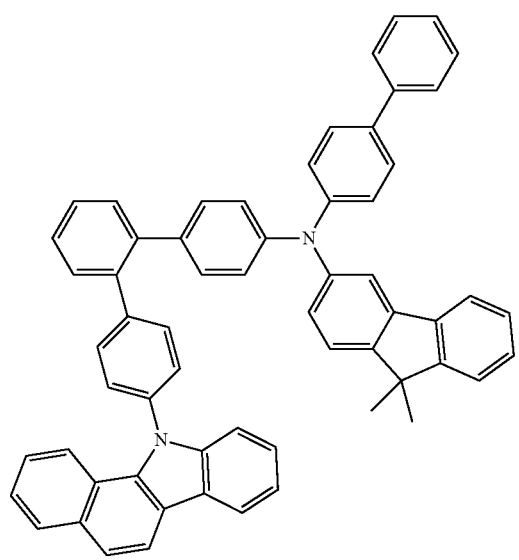
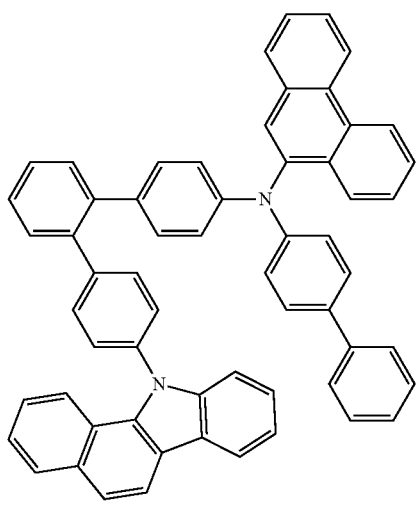
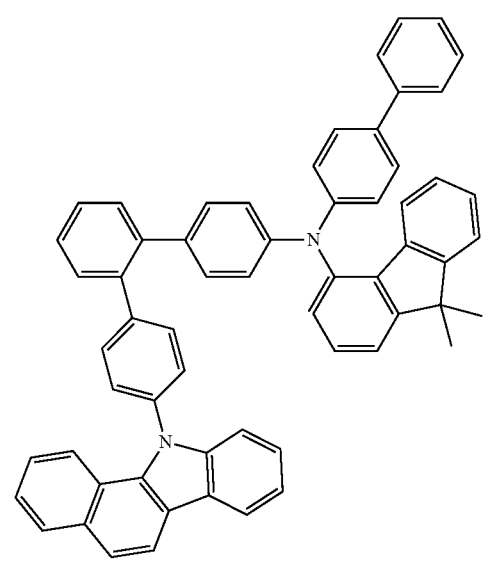
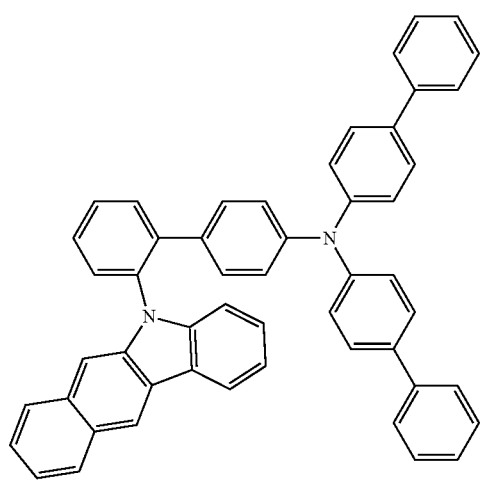

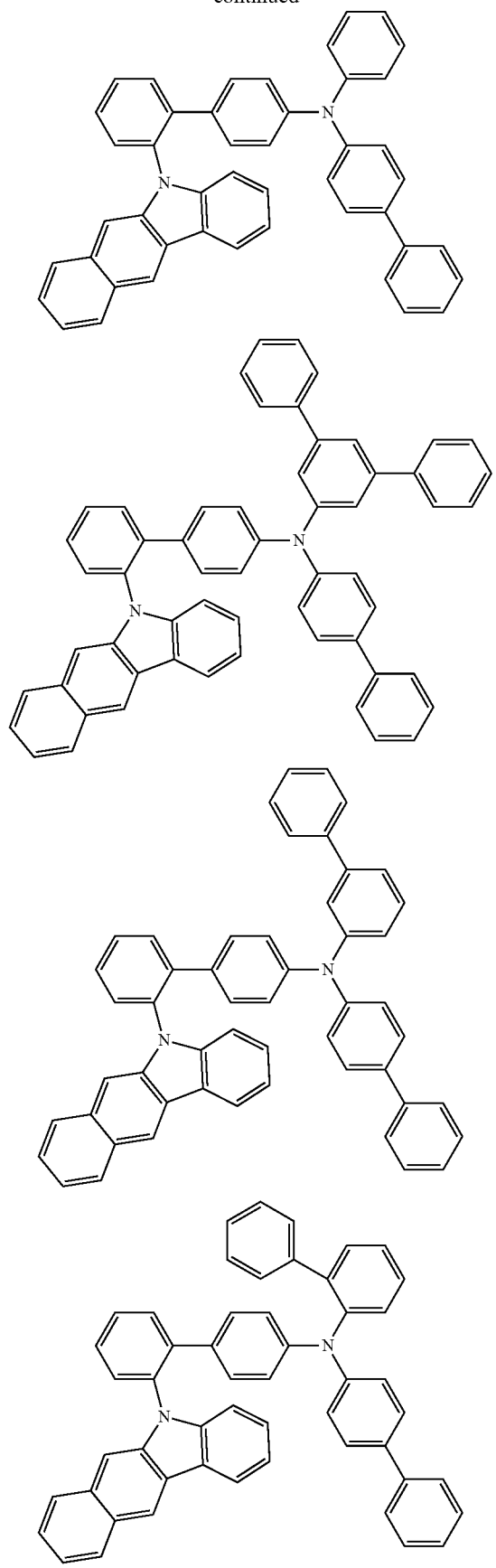
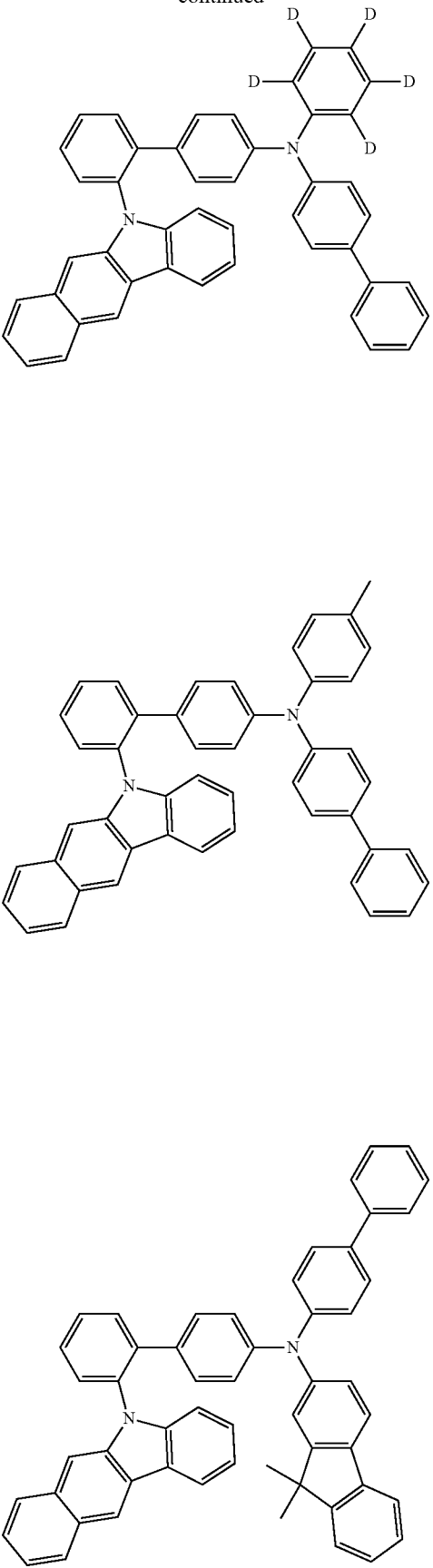

27
-continued
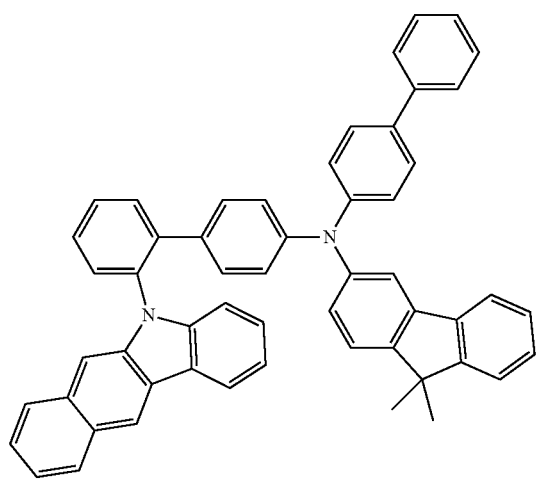
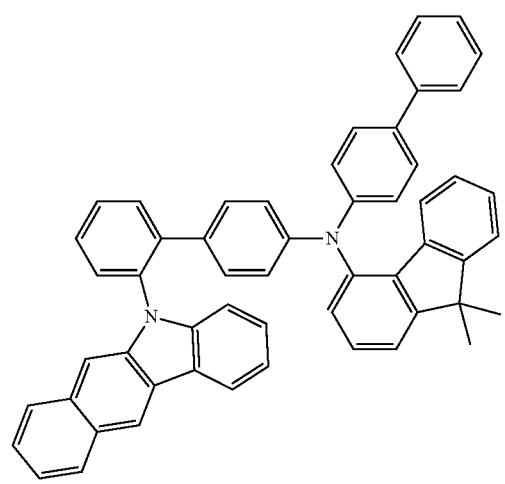
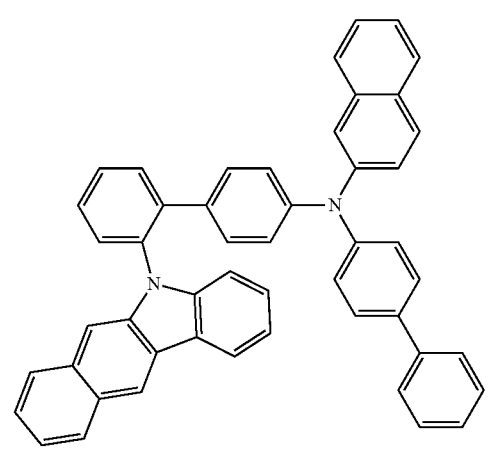
28
-continued
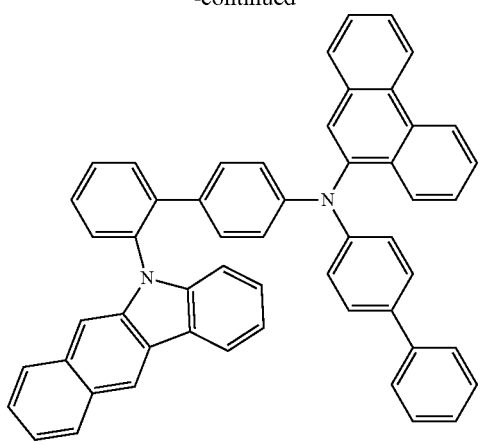
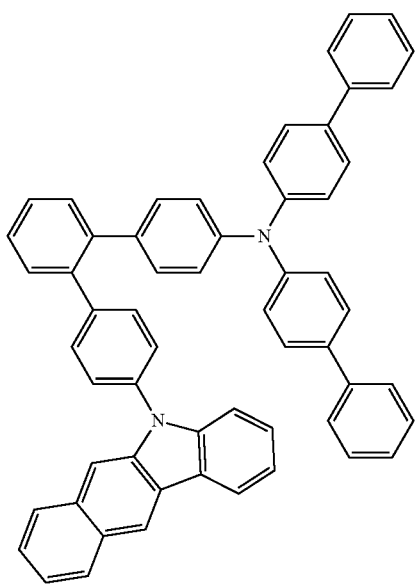
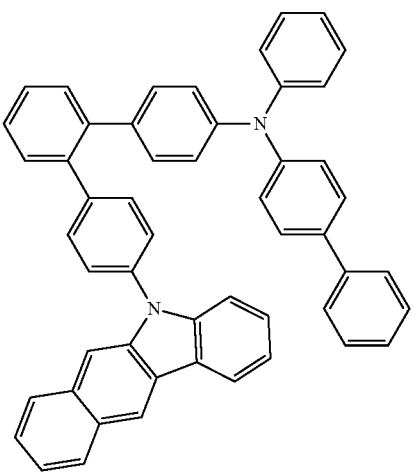

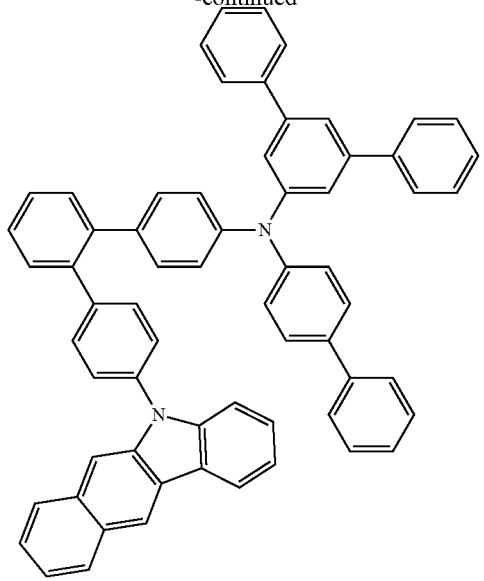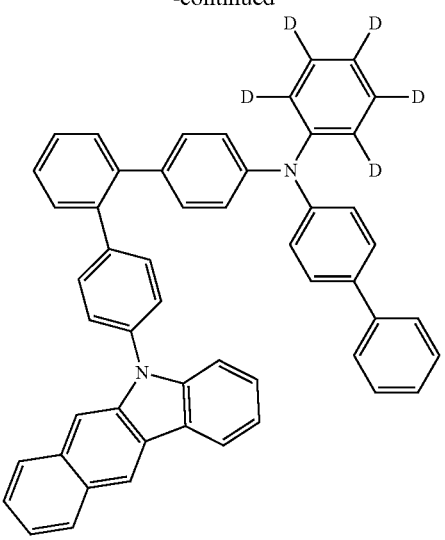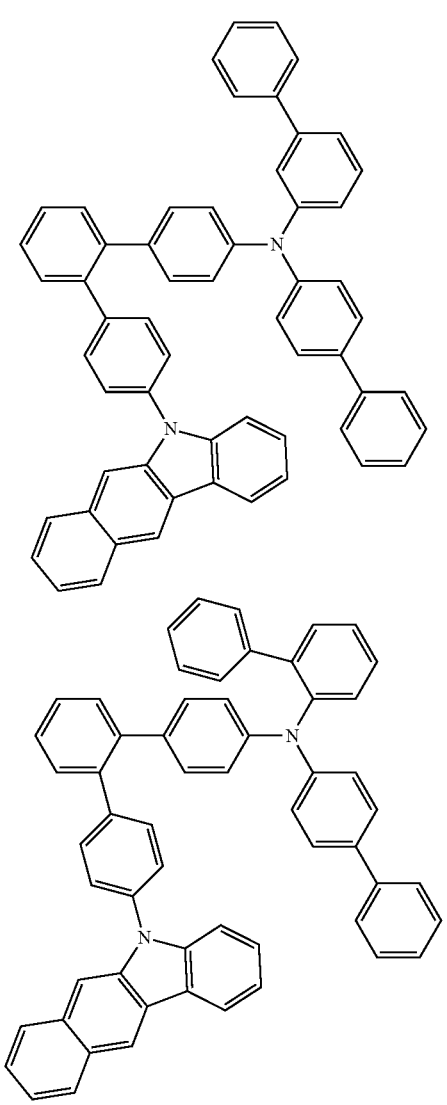

-continued
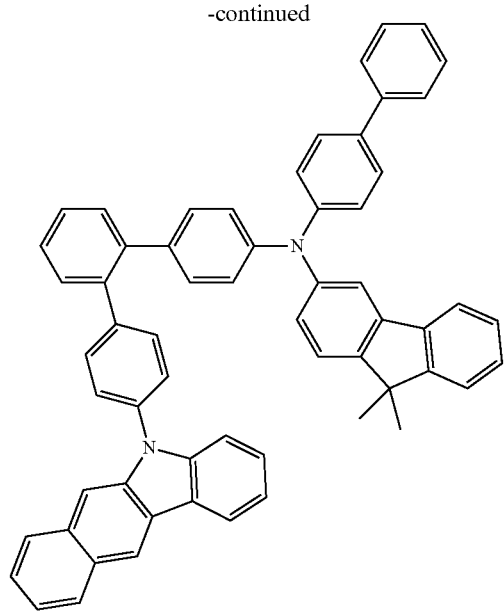
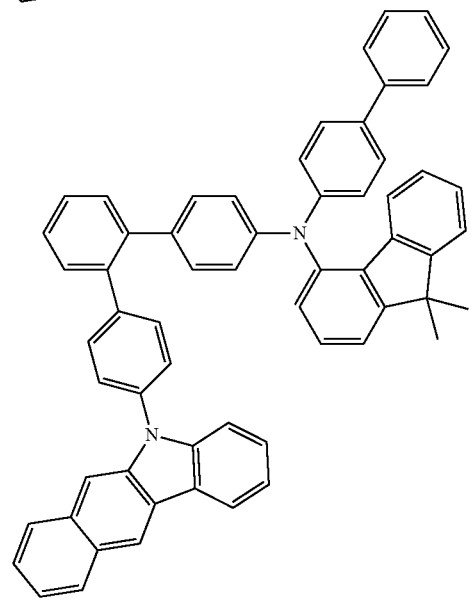
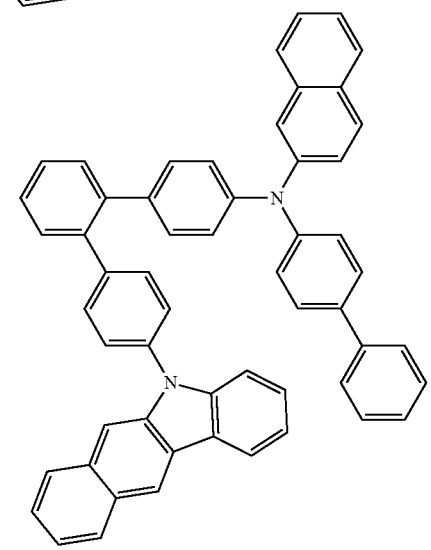
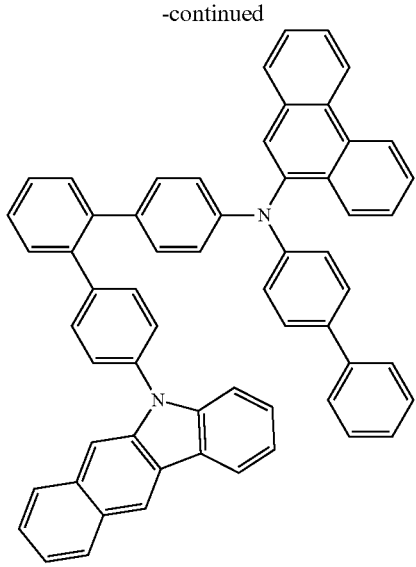
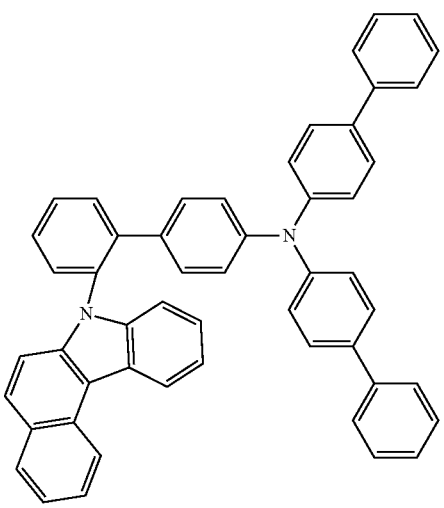
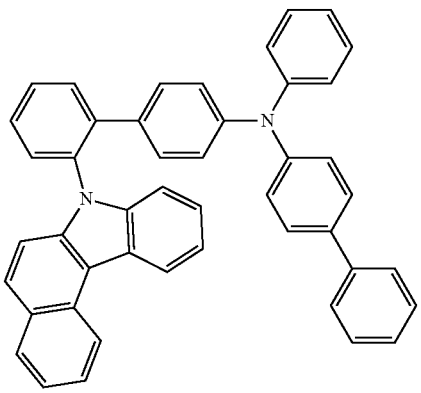

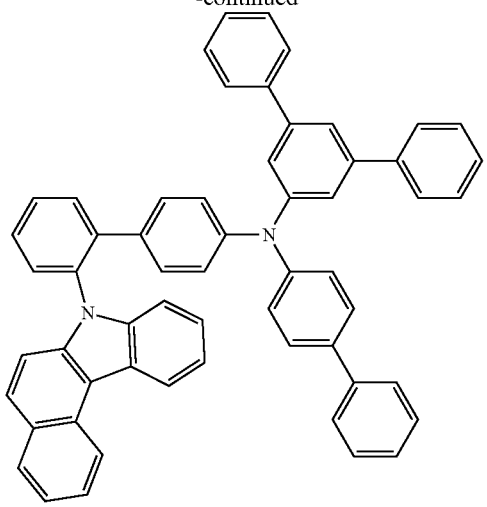
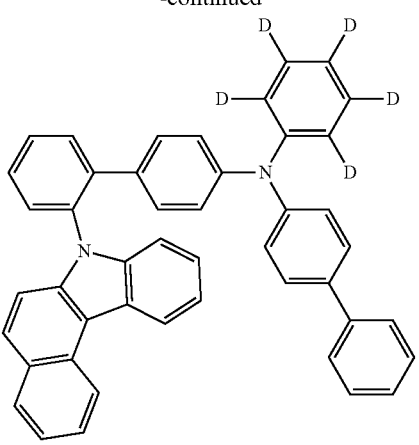
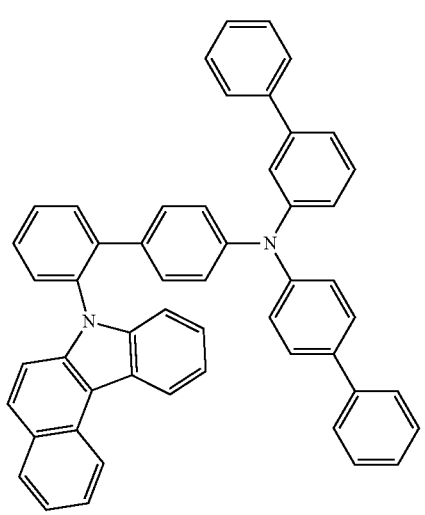
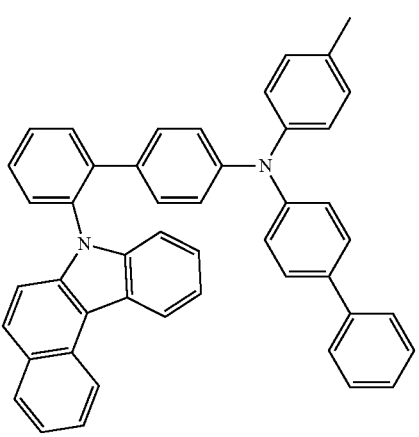
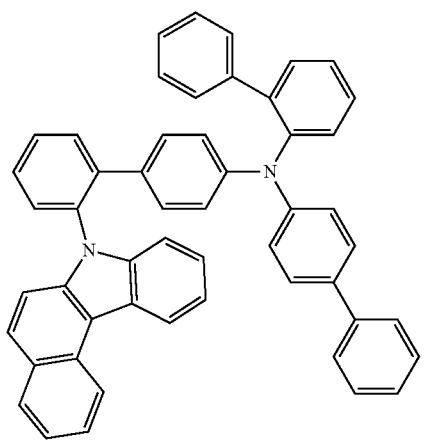
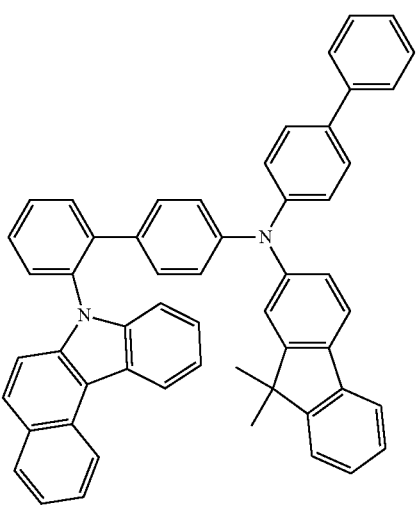

35
-continued
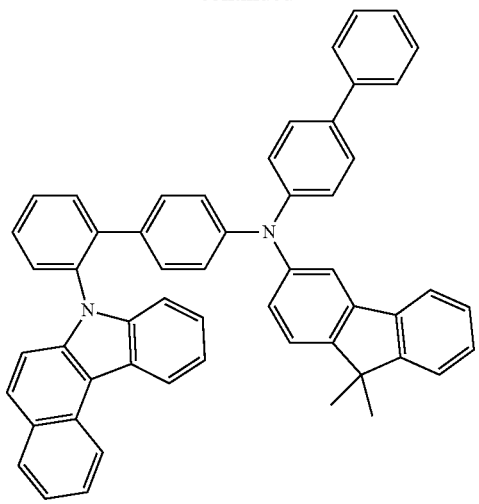
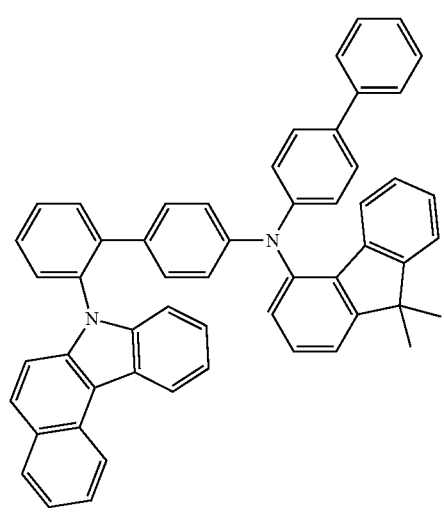
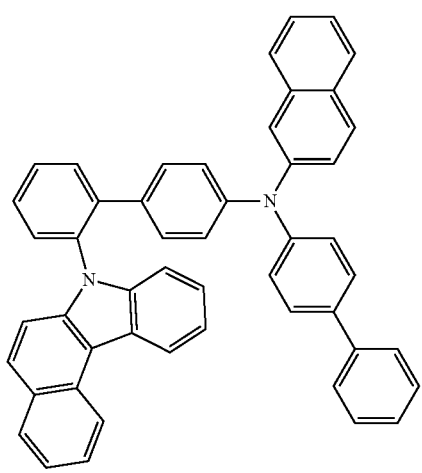
36
-continued
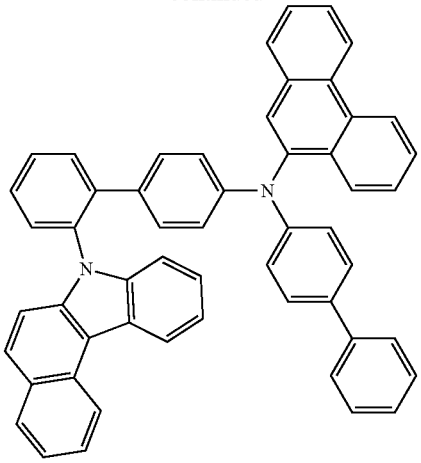
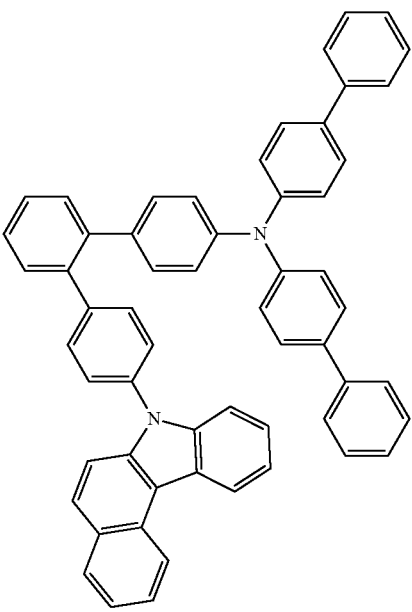
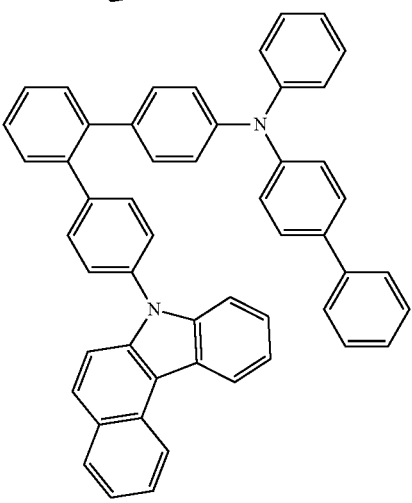

-continued
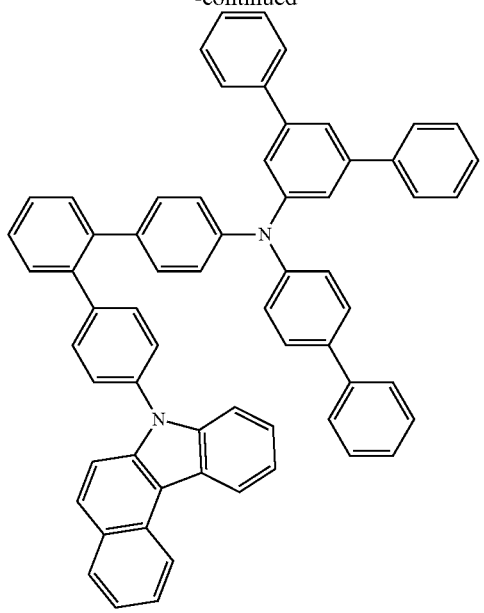
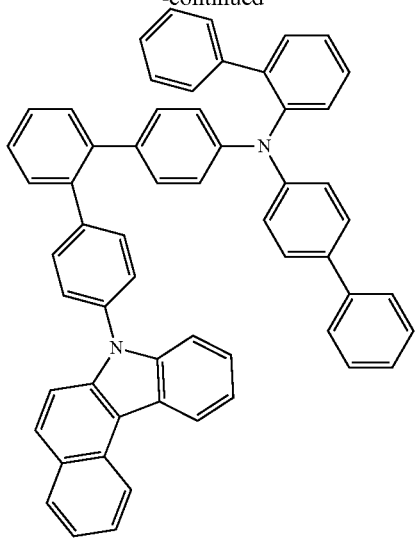
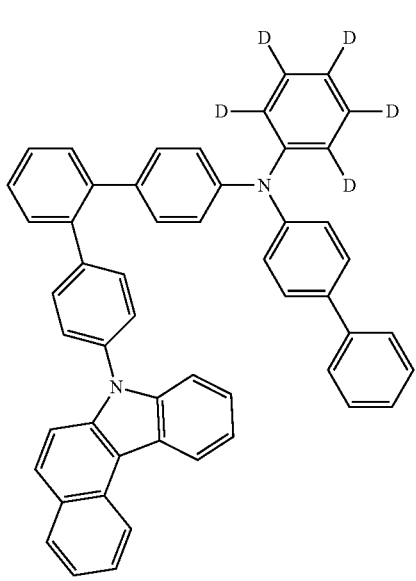
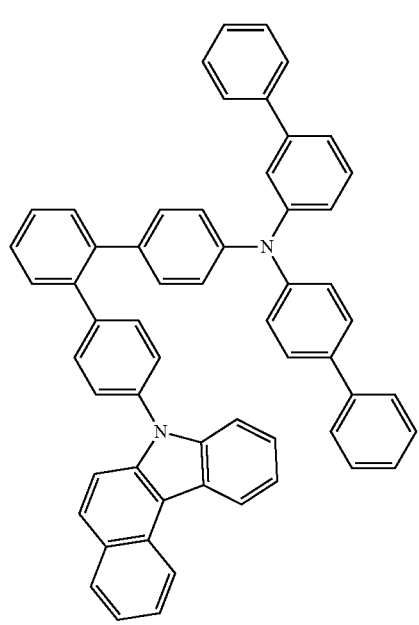
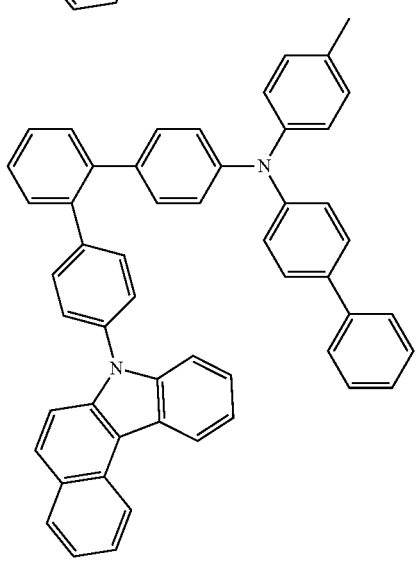

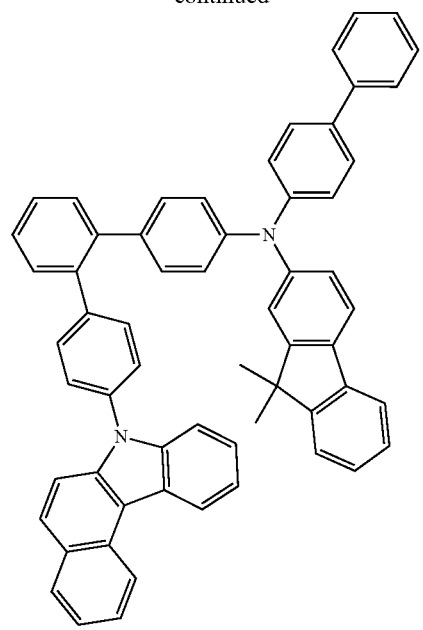
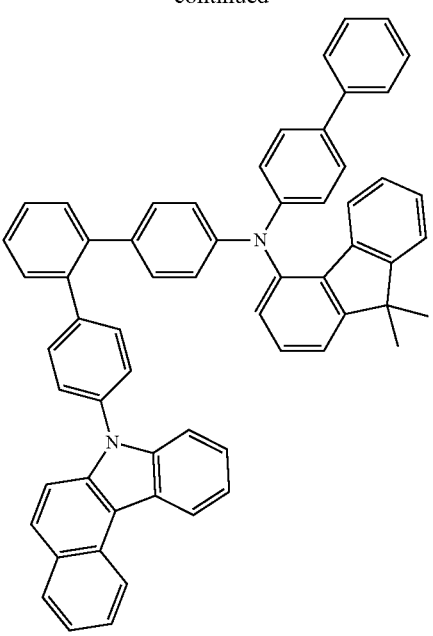
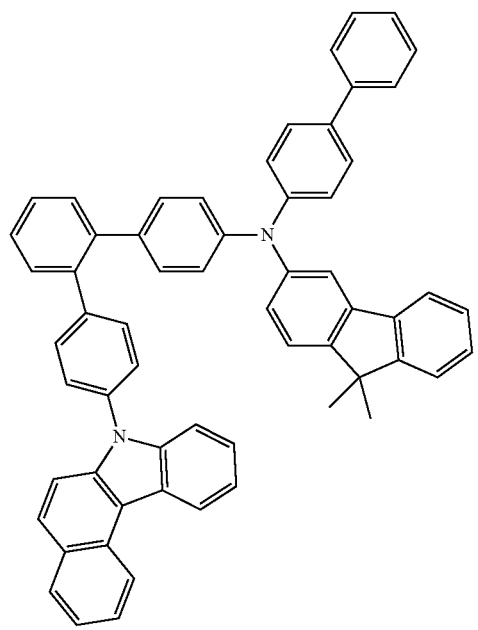
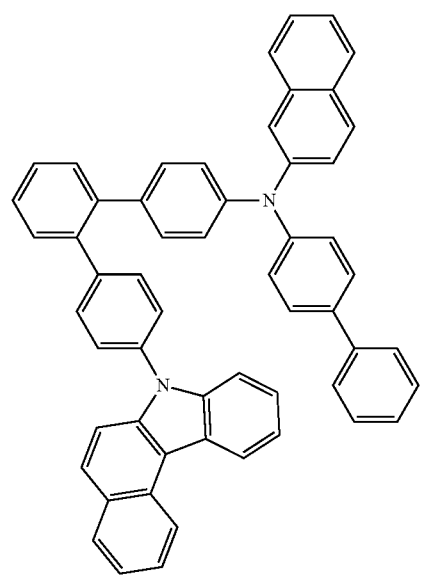

41
-continued
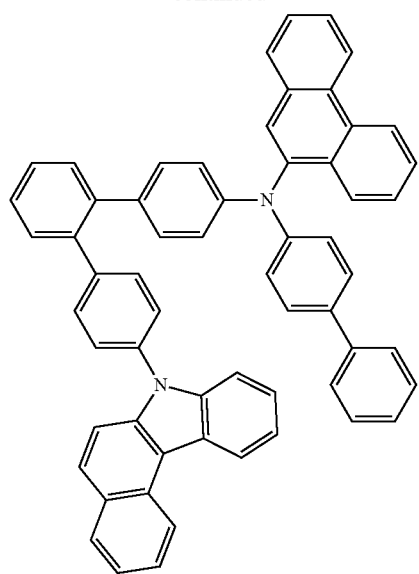
42
-continued
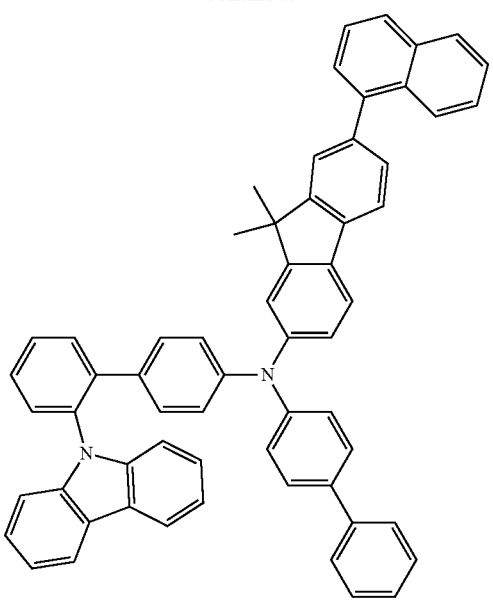
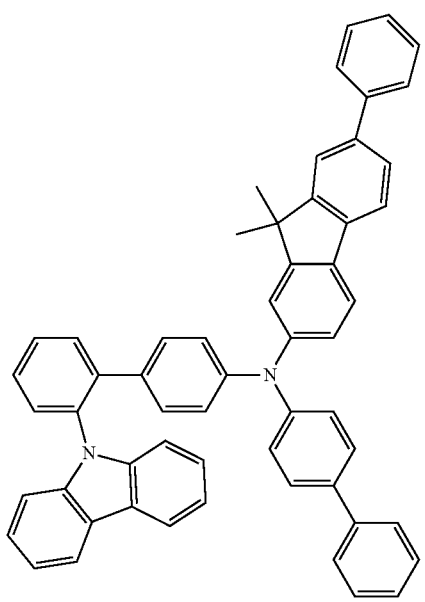
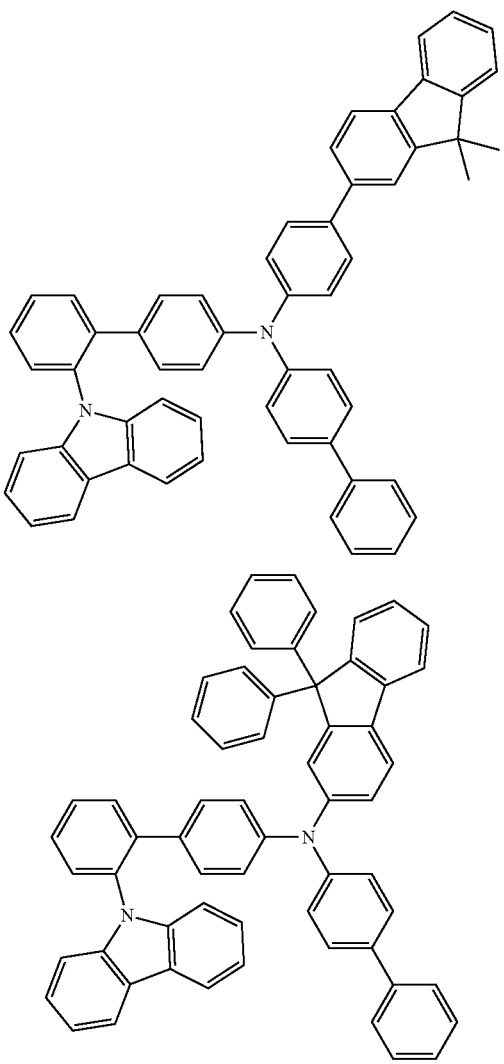

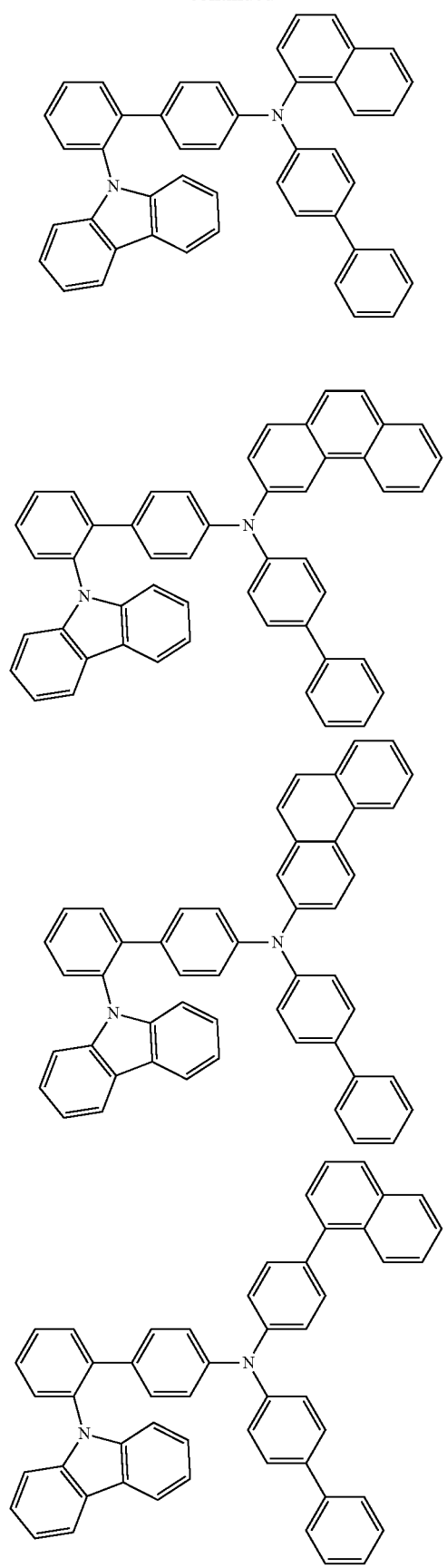
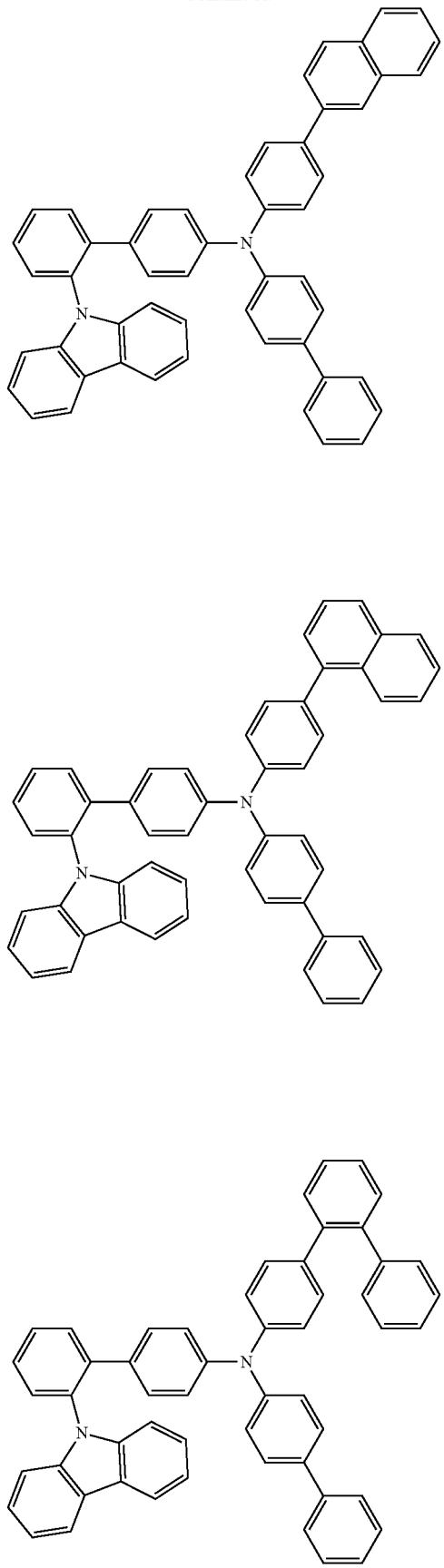

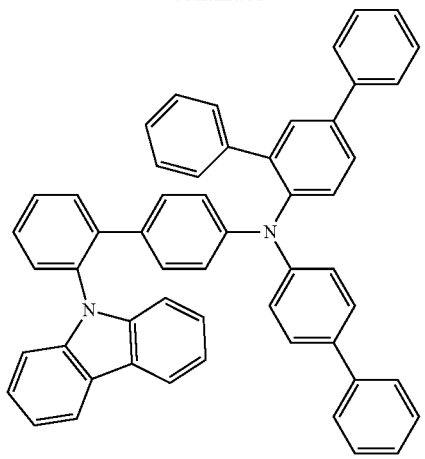
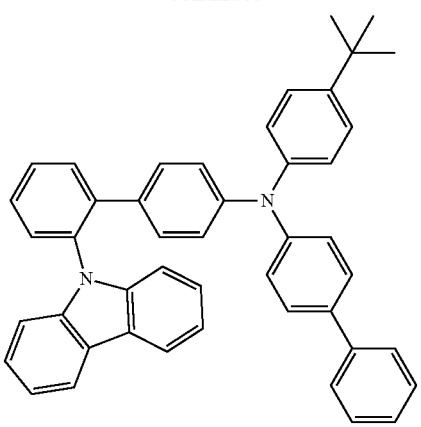
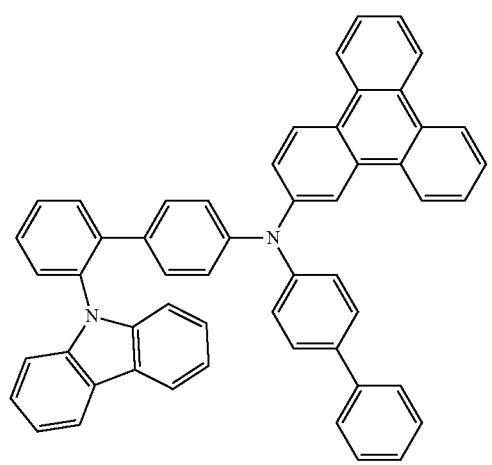
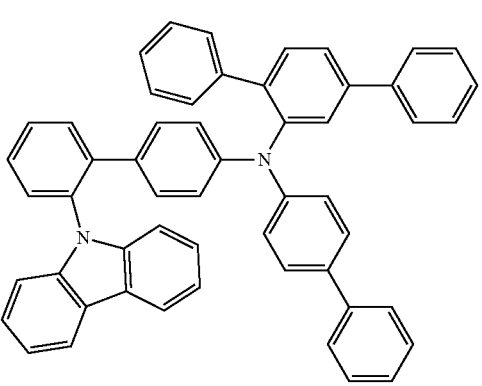
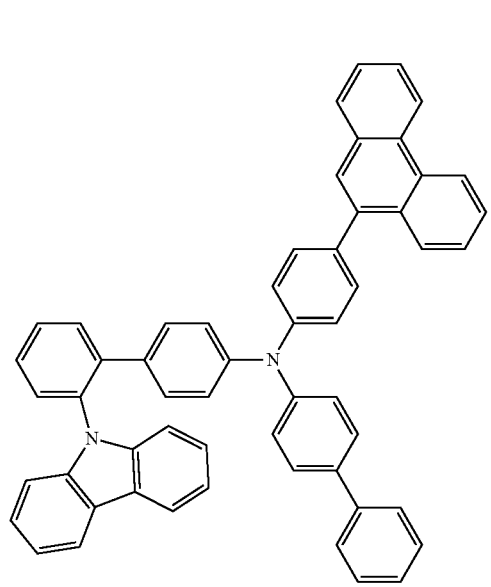
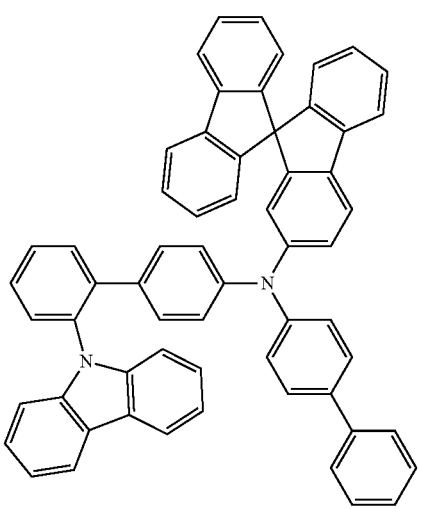

-continued

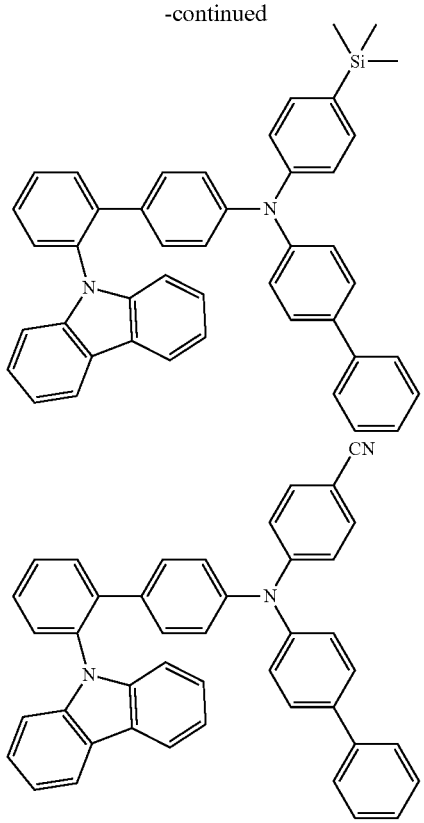

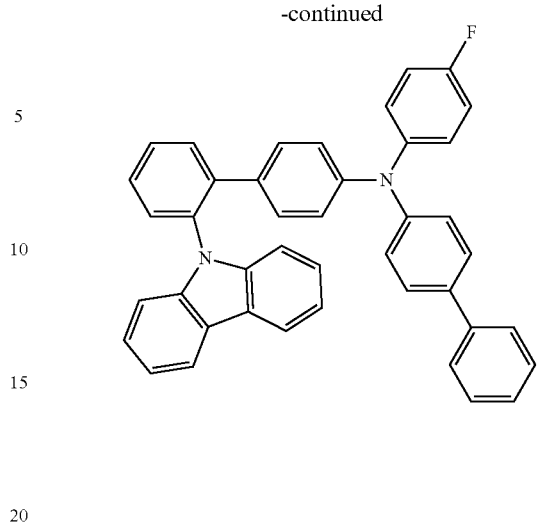

The compound according to an exemplary embodiment of the present specification may be prepared based on the Preparation Examples to be described below, and the core structure of the compound according to an exemplary embodiment of the present specification may be prepared through Reaction Formulae 1 to 3 as described above, but is not limited thereto.

[Reaction Formula 1]

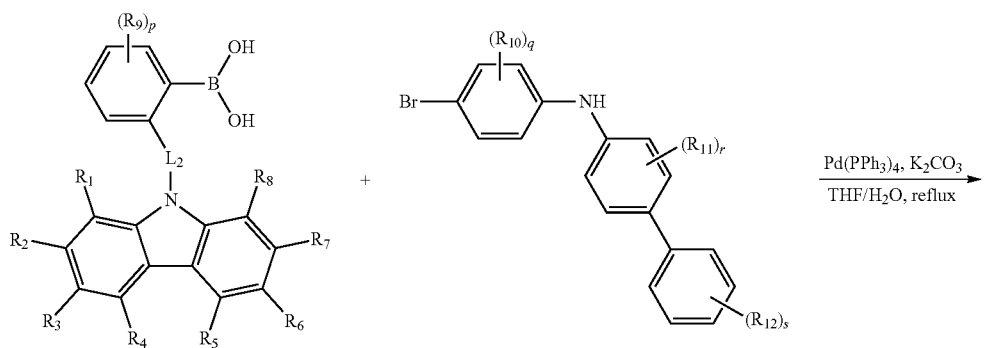

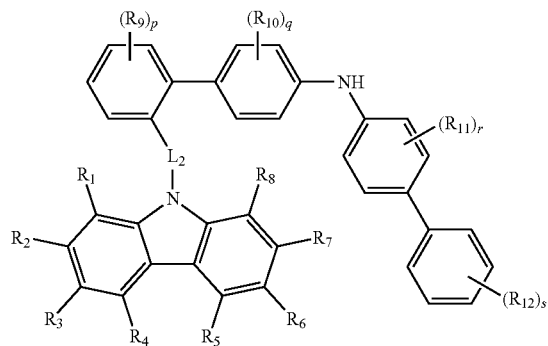

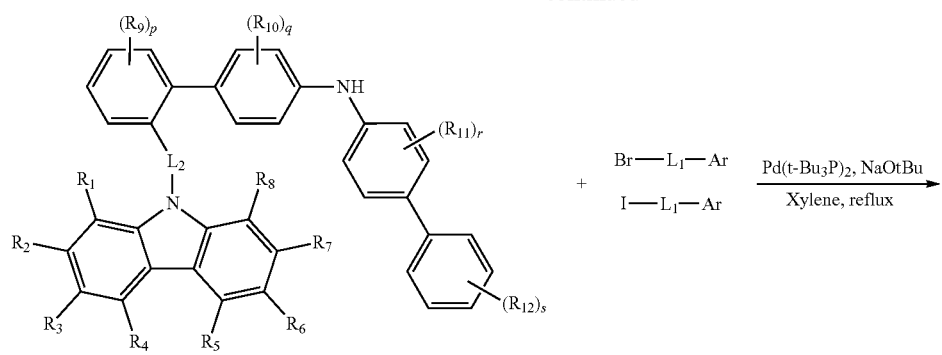
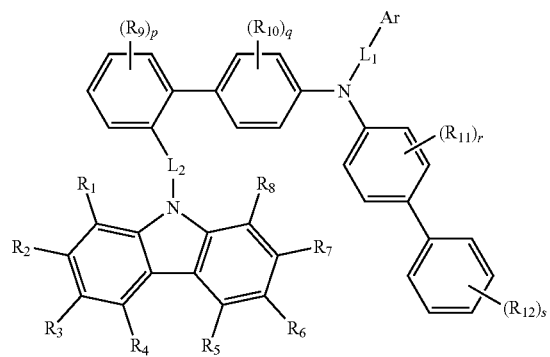
[Reaction Formula 2]
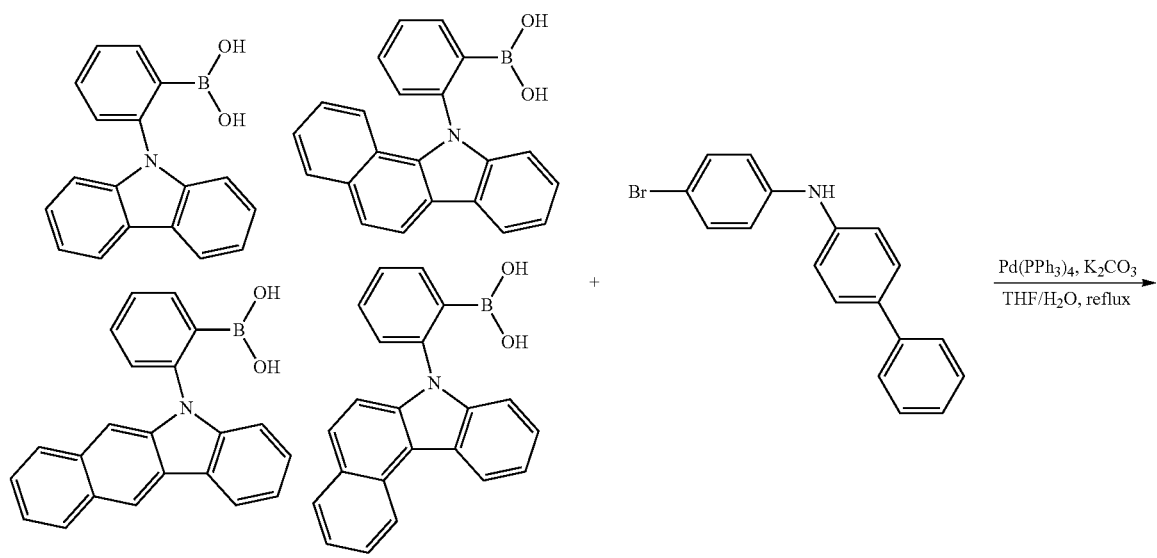

51
-continued
52
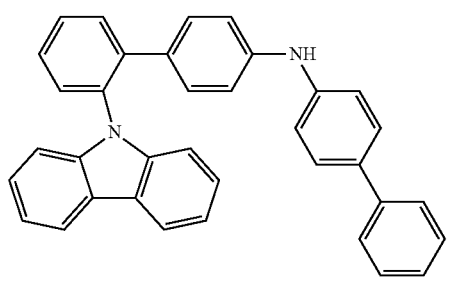
A
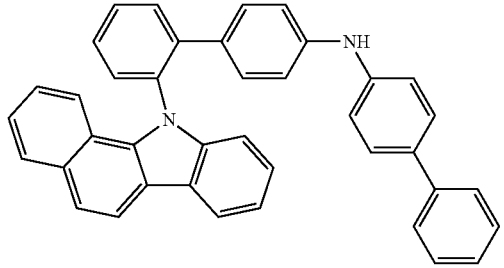
B
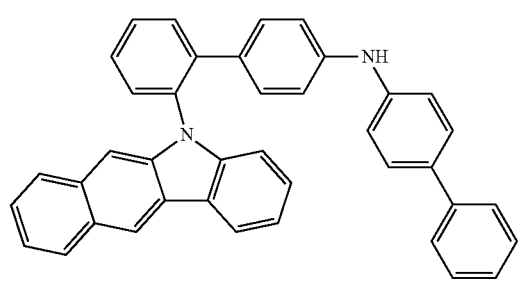
C
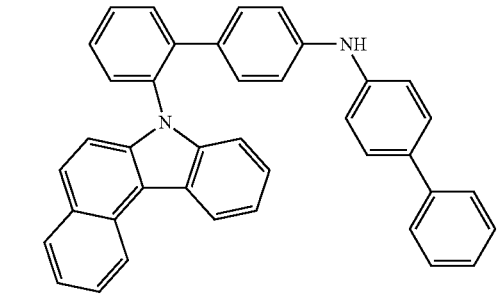
D
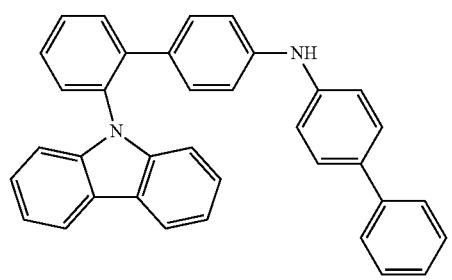
A
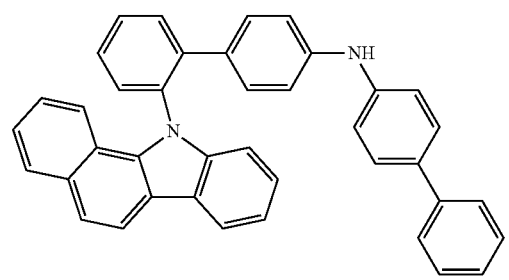
B
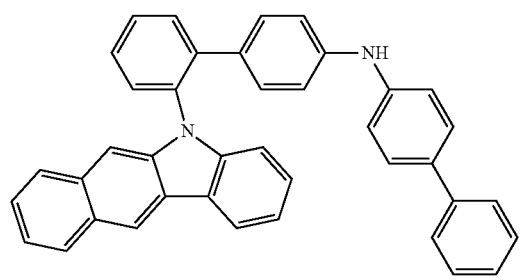
C
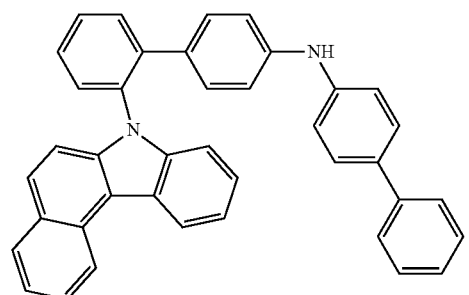
D
+
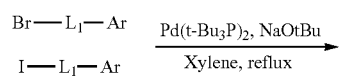

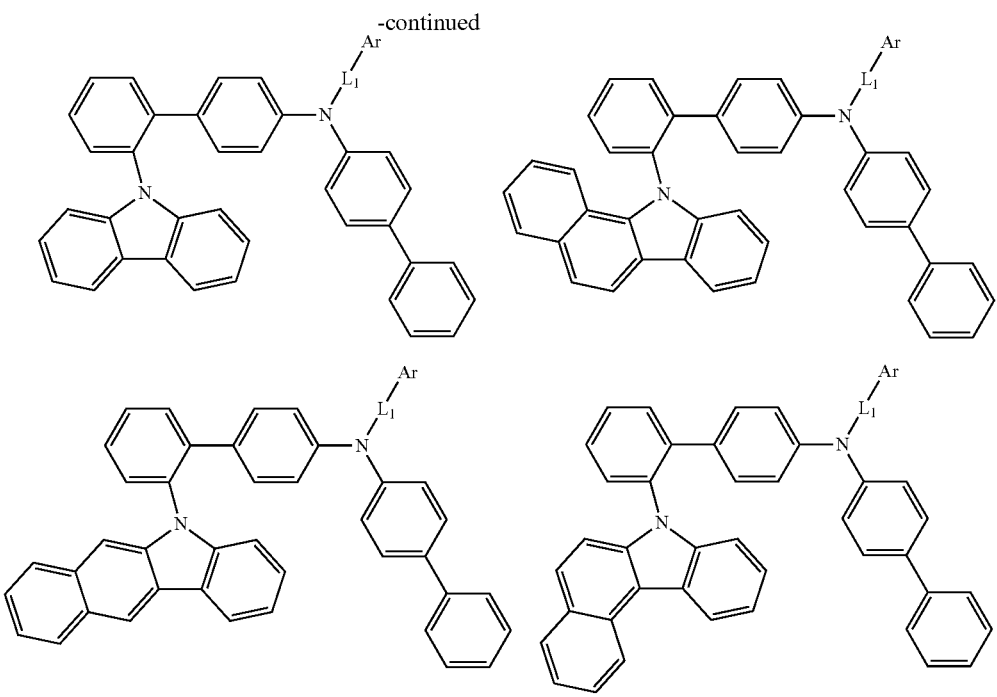
[Reaction Formula 3]
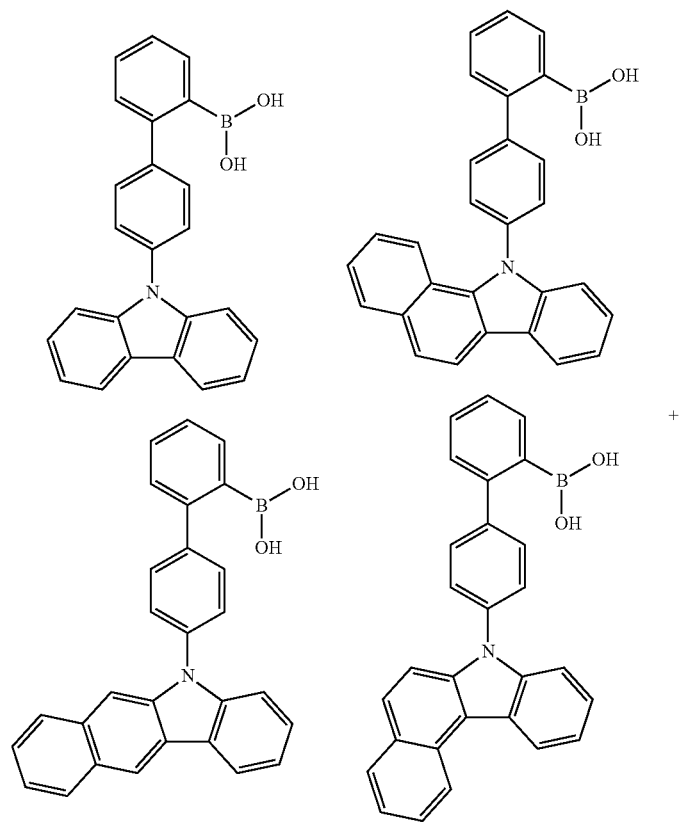

-continued
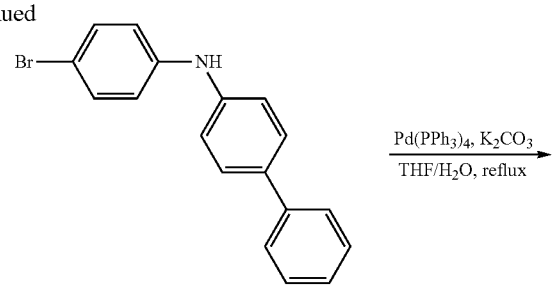
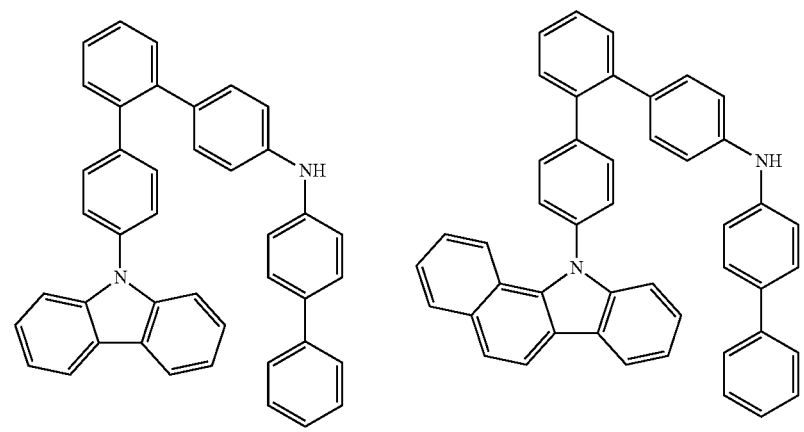
E
F
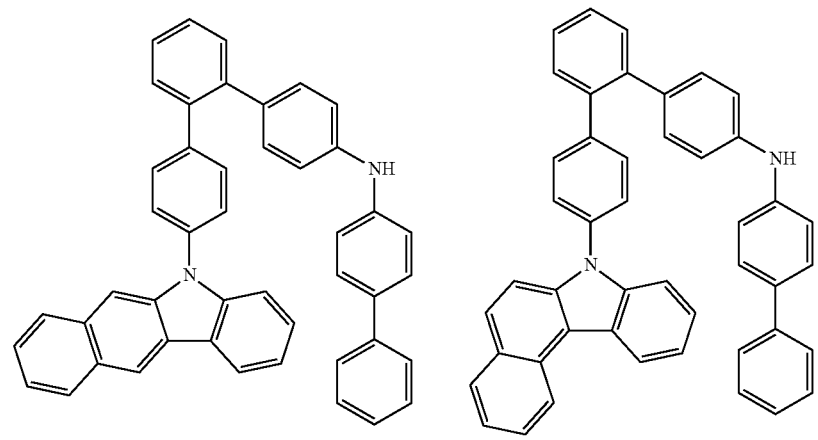
G
H

-continued
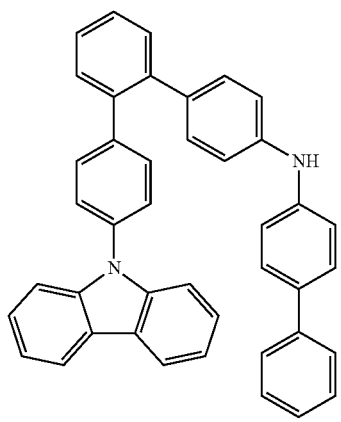
E
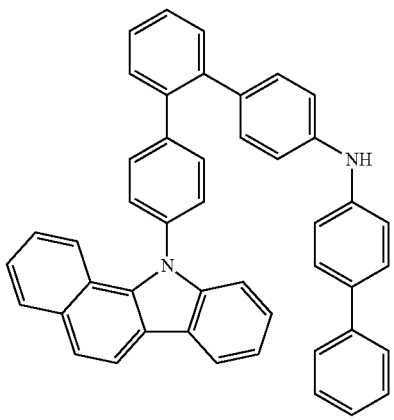
F
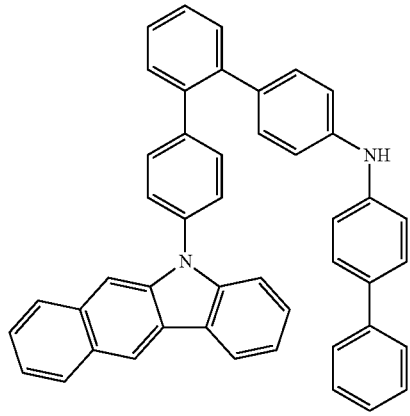
G
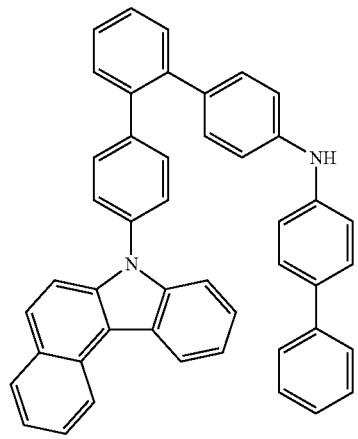
H
+
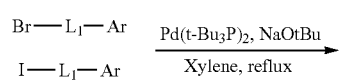

-continued

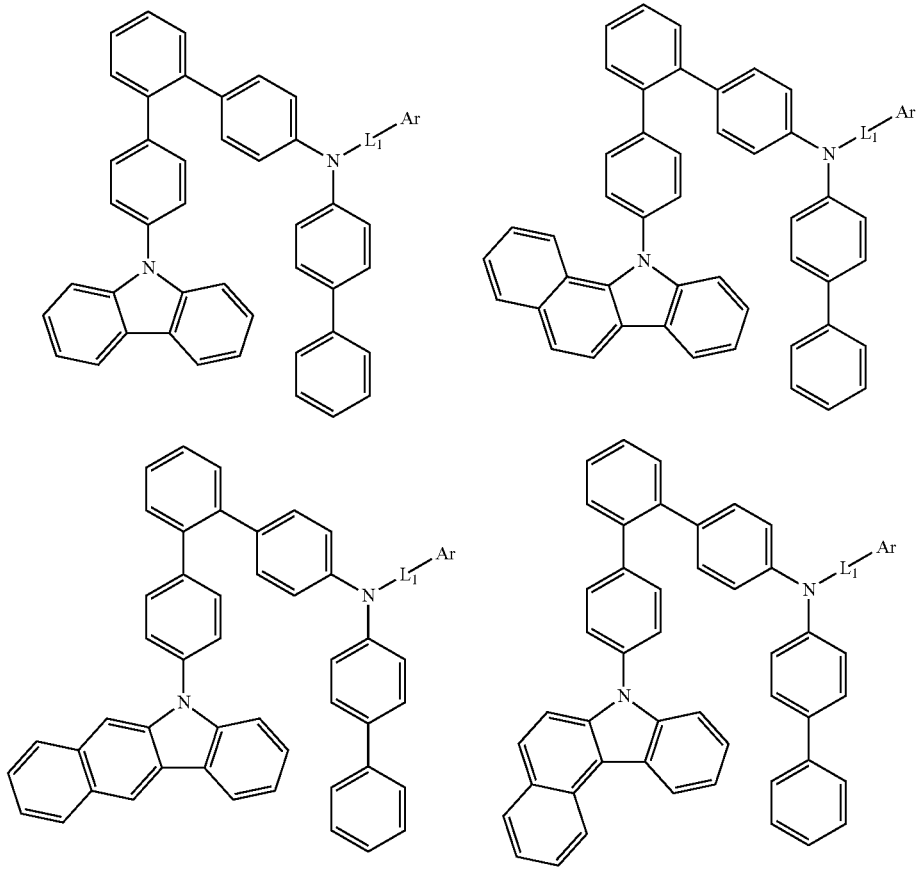

In Reaction Formulae 1 to 3, $L_1$ to $L_3$, $Ar_1$, $Ar_2$, $R_1$ to $R_{10}$, p, and q are the same as those defined in Chemical Formula 1.

Further, the present specification provides an organic electronic device including the above-described compound.

An exemplary embodiment of the present application provides an organic electronic device including: a first electrode; a second electrode provided to face the first electrode; and one or more organic material layers provided between the first electrode and the second electrode, in which one or more layers of the organic material layers include the compound.

When one member is disposed "on" another member in the present specification, this includes not only a case where the one member is brought into contact with another member, but also a case where still another member is present between the two members.

When one part "includes" one constituent element in the present specification, unless otherwise specifically described, this does not mean that another constituent element is excluded, but means that another constituent element may be further included.

The organic electronic device may be selected from the group consisting of an organic light emitting device, an organic solar cell, an organic photoconductor (OPC), and an organic transistor.

The organic material layer of the organic electronic device of the present specification may also be composed of a single-layered structure, but may be composed of a multi-layered structure in which two or more organic material layers are stacked. For example, the organic electronic device of the present specification may have a structure including a hole injection layer, a hole transport layer, a light emitting layer, an electron transport layer, an electron injection layer, and the like as organic material layers. However, the structure of the organic electronic device is not limited thereto, and may include a fewer number of organic layers.

In an exemplary embodiment of the present specification, the organic material layer includes a hole injection layer, a hole transport layer, or a layer which injects and transports holes simultaneously, and the hole injection layer, the hole transport layer, or the layer which injects and transports holes simultaneously includes the compound of Chemical Formula 1.

According to an exemplary embodiment of the present specification, the organic material layer includes an electron blocking layer, and the electron blocking layer includes the compound represented by Chemical Formula 1.

According to another exemplary embodiment, the organic electronic device may be an organic electronic device having a structure (normal type) in which a positive electrode, one or more organic material layers, and a negative electrode are sequentially stacked on a substrate.

According to still another exemplary embodiment, the organic electronic device may be an organic electronic device having a reverse-direction structure (inverted type) in which a negative electrode, one or more organic material layers, and a positive electrode are sequentially stacked on a substrate.

For example, the structure of the organic light emitting device of the present specification may have a structure as illustrated in FIGS. 1 and 2, but is not limited thereto.

FIG. 1 exemplifies the structure of an organic light emitting device 10 in which a first electrode 30, a light emitting layer 40, and a second electrode 50 are sequentially stacked on a substrate 20. FIG. 1 is an exemplified structure of the organic light emitting device according to an exemplary embodiment of the present specification, and may further include other organic material layers.

FIG. 2 exemplifies the structure of an organic light emitting device in which a first electrode 30, a hole injection layer 60, a hole transport layer 70, a light emitting layer 40, an electron transport layer 80, an electron injection layer 90, and a second electrode 50 are sequentially stacked on a substrate 20. FIG. 2 is an exemplified structure according to exemplary embodiments of the present specification, and may further include other organic material layers.

According to an exemplary embodiment of the present specification, the organic material layer includes a light emitting layer, and the light emitting layer includes a compound represented by the following Chemical Formula 1-A.

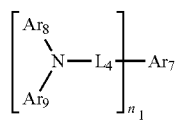

[Chemical Formula 1-A]

In Chemical Formula 1-A, n1 is an integer of 1 or more, $Ar_7$ is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, $L_4$ is a direct bond; a substituted or unsubstituted arylene group; or a substituted or unsubstituted heteroarylene group, $Ar_8$ and $Ar_9$ are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or may combine with each other to form a substituted or unsubstituted ring, and when $n_1$ is 2 or more, two or more structures in the parenthesis are the same as or different from each other.

According to an exemplary embodiment of the present specification, the organic material layer includes a light emitting layer, and the light emitting layer includes the compound represented by Chemical Formula 1-A as a dopant of the light emitting layer.

According to an exemplary embodiment of the present specification, $L_4$ is a direct bond.

According to an exemplary embodiment of the present specification, $n_1$ is 2.

In an exemplary embodiment of the present specification, $Ar_7$ is a divalent pyrene group which is unsubstituted or substituted with deuterium, a methyl group, an ethyl group, or a tert-butyl group.

According to an exemplary embodiment of the present specification, $Ar_8$ and $Ar_9$ are the same as or different from each other, and are each independently a substituted or unsubstituted aryl group having 6 to 30 carbon atoms.

According to an exemplary embodiment of the present specification, $Ar_8$ and $Ar_9$ are the same as or different from each other, and are each independently an aryl group which is unsubstituted or substituted with a germanium group substituted with an alkyl group.

According to an exemplary embodiment of the present specification, $Ar_8$ and $Ar_9$ are the same as or different from each other, and are each independently an aryl group which is unsubstituted or substituted with a trimethylgermanium group.

According to an exemplary embodiment of the present specification, $Ar_8$ and $Ar_9$ are the same as or different from each other, and are each independently a substituted or unsubstituted phenyl group.

According to an exemplary embodiment of the present specification, $Ar_8$ and $Ar_9$ are a phenyl group which is unsubstituted or substituted with a trimethylgermanium group.

According to an exemplary embodiment of the present specification, Chemical Formula 1-A is represented by the following compound.

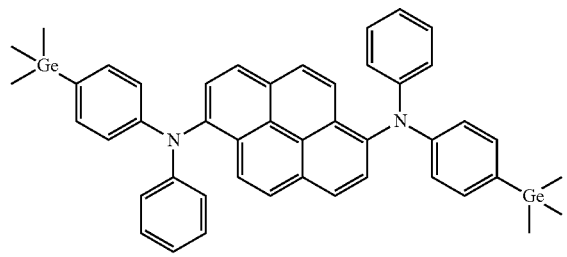

According to an exemplary embodiment of the present specification, the organic material layer includes a light emitting layer, and the light emitting layer includes a compound represented by the following Chemical Formula 2-A.

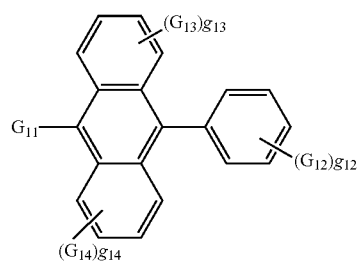

[Chemical Formula 2-A]

In Chemical Formula 2-A, $G_{11}$ is a 1-naphthyl group, a 2-naphthyl group, a 1-anthracenyl group, a 2-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

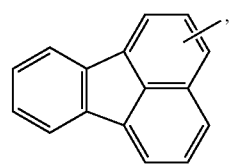

$G_{12}$ is a phenyl group, a 1-naphthyl group, a 2-naphthyl group, a 1-anthracenyl group, a 2-anthracenyl group, a 9-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthracenyl group, a 4'-methylbiphenylyl group, a 4''-t-butyl-p-terphenyl-4-yl group, or a 3-fluoranthenyl group, $G_{13}$ and $G_{14}$ are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, $g_{12}$ is an integer of 1 to 5, $g_{13}$ and $g_{14}$ are each an integer of 1 to 4, and when $g_{12}$ to $g_{14}$ are each 2 or more, two or more structures in the parenthesis are the same as or different from each other.

According to an exemplary embodiment of the present specification, the organic material layer includes a light emitting layer, and the light emitting layer includes the compound represented by Chemical Formula 2-A as a host of the light emitting layer.

According to an exemplary embodiment of the present specification, $G_{11}$ is a 1-naphthyl group.

According to an exemplary embodiment of the present specification, $G_{12}$ is a 2-naphthyl group.

According to an exemplary embodiment of the present specification, $G_{13}$ and $G_{14}$ are hydrogen.

According to an exemplary embodiment of the present specification, Chemical Formula 2-A is represented by the following compound.

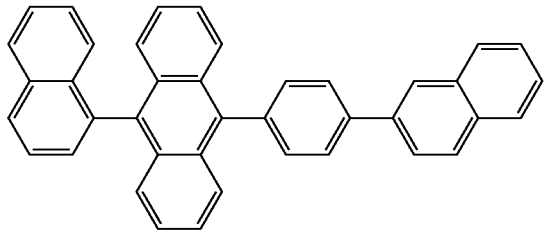 [SMILES: c1ccc2cc(-c3ccc(-c4c5ccccc5c(-c5cccc6ccccc56)c5ccccc45)cc3)ccc2c1]

The organic light emitting device of the present specification may be manufactured by the materials and methods known in the art, except that one or more layers of the organic material layers include the heterocyclic compound of the present specification, that is, the compound represented by Chemical Formula 1.

When the organic light emitting device includes a plurality of organic material layers, the organic material layers may be formed of the same material or different materials.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a first electrode, forming an organic material layer including a hole injection layer, a hole transport layer, a light emitting layer, and an electron transport layer thereon, and then depositing a material, which may be used as a second electrode, thereon, by using a physical vapor deposition (PVD) method such as sputtering or e-beam evaporation. In addition to the method as described above, an organic light emitting device may be made by sequentially depositing a negative electrode material, an organic material layer, and a first electrode material on a substrate. Further, the compound represented by Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

According to an exemplary embodiment of the present specification, the first electrode is a positive electrode, and the second electrode is a negative electrode.

According to another exemplary embodiment of the present specification, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or SnO$_2$:Sb; an electrically conductive polymer, such as poly(3-methylthiophene), poly[3,4-(ethylene-1,2-dioxy)thiophene](PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or LiO$_2$/Al and Mg/Ag, and the like, but are not limited thereto.

The hole injection layer is a layer which injects holes from an electrode, and a hole injection material is preferably a compound which has a capability of transporting holes, and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transport layer is a layer which receives holes from a hole injection layer and transports the holes to a light emitting layer, and a hole transport material is suitably a material which may receive holes from a positive electrode or a hole injection layer to transfer the holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The electron blocking layer is a layer which may improve the lifetime and efficiency of the device by preventing holes injected from a hole injection layer from passing through a light emitting layer and entering an electron injection layer, and may be formed at an appropriate portion between the light emitting layer and the electron injection layer using publicly-known materials, if necessary.

The light emitting material of the light emitting layer is a material which may receive holes and electrons from a hole transport layer and an electron transport layer, respectively, and combine the holes and the electrons to emit light in a visible ray region, and is preferably a material having good quantum efficiency to fluorescence or phosphorescence. Specific examples thereof include: an 8-hydroxy-quinoline aluminum complex ($Alq_3$); a carbazole-based compound; a dimerized styryl compound; BAlq; a 10-hydroxybenzoquinoline-metal compound; a benzoxazole, benzothiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a fused aromatic ring derivative, or a hetero ring-containing compound, and the like. Specifically, examples of the fused aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a fused aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer which receives electrons from an electron injection layer and transports the electrons to a light emitting layer, and an electron transport material is suitably a material which may receive electrons well from a negative electrode and transfer the electrons to a light emitting layer, and has a large mobility for electrons. Specific examples thereof include: an Al complex of 8-hydroxyquinoline; a complex including $Alq_3$; an organic radical compound; a hydroxyflavone-metal complex, and the like, but are not limited thereto. The electron transport layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris (2-methyl-8-hydroxyquinolinato) aluminum, tris(8-hydroxyquinolinato) gallium, bis(10-hydroxybenzo[h] quinolinato) beryllium, bis(10-hydroxybenzo[h] quinolinato) zinc, bis(2-methyl-8-quinolinato) chlorogallium, bis(2-methyl-8-quinolinato) (o-cresolato) gallium, bis(2-methyl-8-quinolinato)(1-naphtholato) aluminum, bis(2-methyl-8-quinolinato)(2-naphtholato) gallium, and the like, but are not limited thereto.

The hole blocking layer is a layer which blocks holes from reaching a negative electrode, and may be generally formed under the same conditions as those of the hole injection layer. Specific examples thereof include an oxadiazole derivative or a triazole derivative, a phenanthroline derivative, BCP, an aluminum complex, and the like, but are not limited thereto.

The organic light emitting device according to the present specification may be a top emission type, a bottom emission type, or a dual emission type according to the material to be used.

According to an exemplary embodiment of the present specification, the compound represented by Chemical Formula 1 may be included in an organic solar cell or an organic transistor in addition to the organic light emitting device.

Hereinafter, the present specification will be described in detail with reference to Examples in order to specifically explain the present specification. However, the Examples according to the present specification may be modified in various forms, and it is not interpreted that the scope of the present specification is limited to the Examples described below in detail. The Examples of the present specification are provided to more completely explain the present specification to a person with ordinary skill in the art.

EXAMPLES

<Preparation Example 1>—Synthesis of Compound 1-1

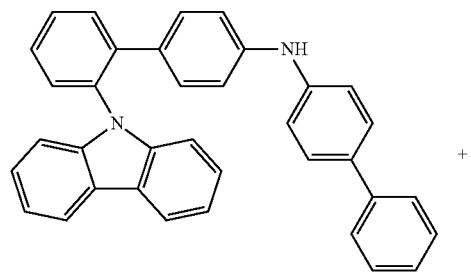

A
[Compound A]

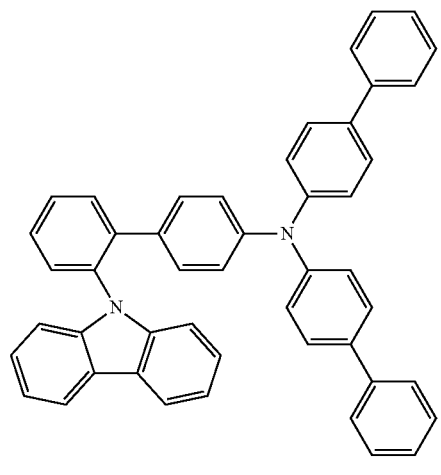

[Compound 1-1]

Under a nitrogen atmosphere, Compound A (10.0 g, 20.58 mmol) and 4-bromo-1,1'-biphenyl (5.25 g, 22.63 mmol) were completely dissolved in 180 ml of xylene in a 500 ml-round bottom flask, and then sodium-tert-butoxide (2.57 g, 26.75 mmol) was added thereto, bis(tri-tert-butylphosphine) palladium (0.11 g, 0.21 mmol) was put thereinto, and then the resulting mixture was heated and stirred for 3 hours. The temperature was lowered to normal temperature, the resulting mixture was filtered to remove the salt, and then xylene was concentrated under reduced pressure, and the residue was recrystallized with 250 ml of ethyl acetate to prepare Compound 1-1 (11.56 g, yield: 88%).

MS[M+H]$^+$=639

<Preparation Example 2>—Synthesis of Compound 1-2

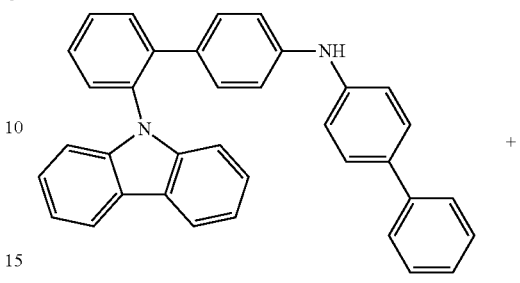

[Compound A]
A

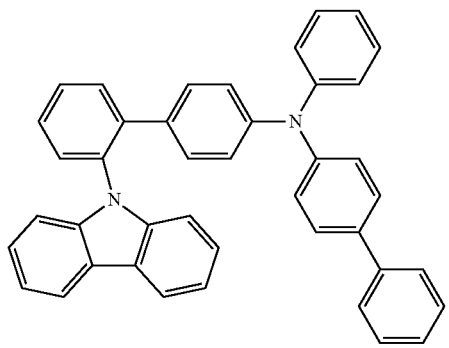

[Compound 1-2]

Under a nitrogen atmosphere, Compound A (10.0 g, 20.58 mmol) and bromobenzene (3.53 g, 22.63 mmol) were completely dissolved in 120 ml of xylene in a 500 ml-round bottom flask, and then sodium-tert-butoxide (2.57 g, 26.75 mmol) was added thereto, bis(tri-tert-butylphosphine) palladium (0.11 g, 0.21 mmol) was put thereinto, and then the resulting mixture was heated and stirred for 1 hour. The temperature was lowered to normal temperature, the resulting mixture was filtered to remove the salt, and then xylene was concentrated under reduced pressure, and the residue was recrystallized with 250 ml of ethyl acetate to prepare Compound 1-2 (9.16 g, yield: 79%).

MS[M+H]$^+$=563

<Preparation Example 3>—Synthesis of Compound 1-3

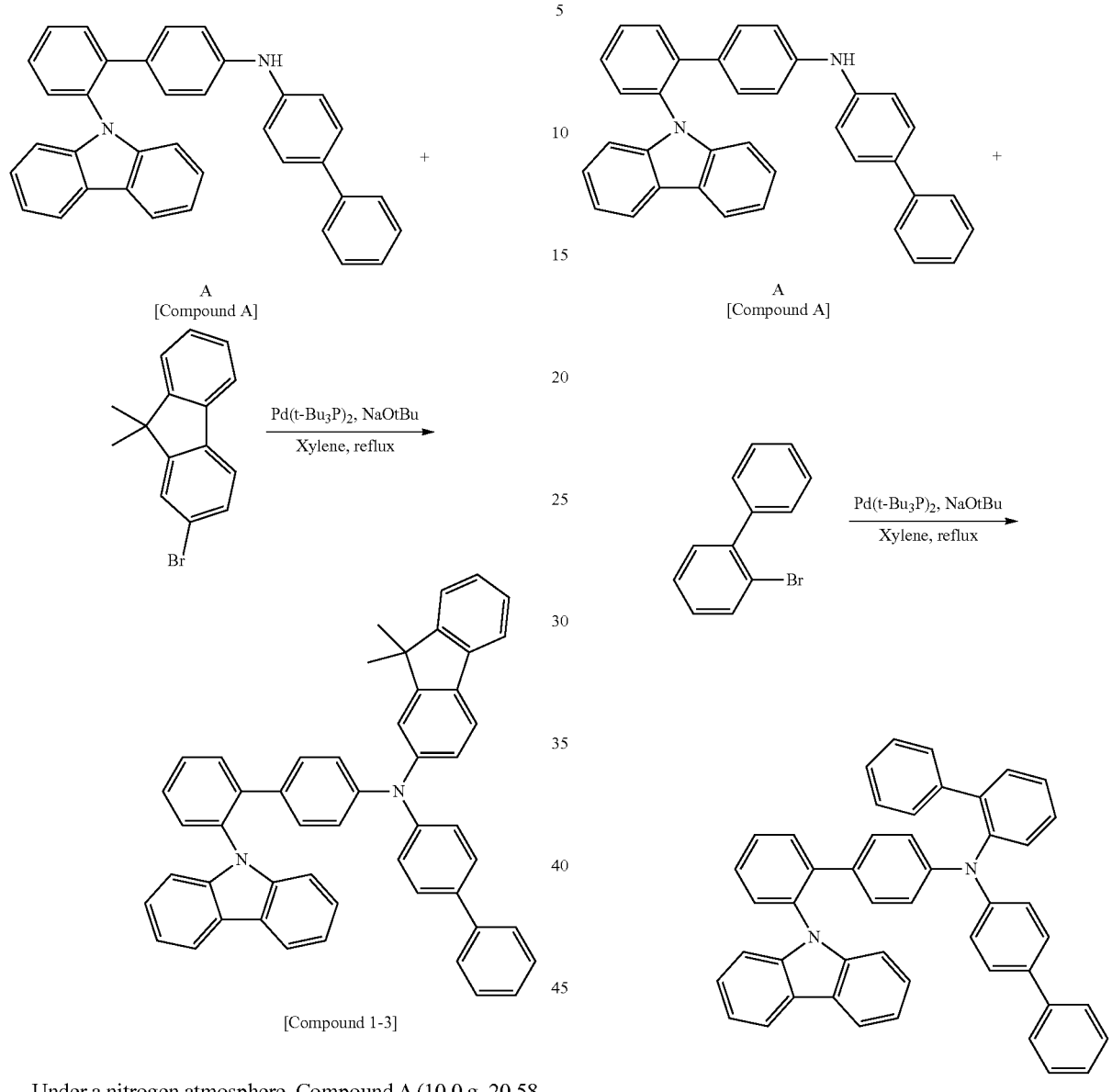

[Compound 1-3]

Under a nitrogen atmosphere, Compound A (10.0 g, 20.58 mmol) and 2-bromo-9,9-diphenyl-9H-fluorene (6.16 g, 22.63 mmol) were completely dissolved in 140 ml of xylene in a 500 ml-round bottom flask, and then sodium-tert-butoxide (2.57 g, 26.75 mmol) was added thereto, bis(tri-tert-butylphosphine) palladium (0.11 g, 0.21 mmol) was put thereinto, and then the resulting mixture was heated and stirred for 2 hours. The temperature was lowered to normal temperature, the resulting mixture was filtered to remove the salt, and then xylene was concentrated under reduced pressure, and the residue was recrystallized with 200 ml of ethyl acetate to prepare Compound 1-3 (10.33 g, yield: 74%).

MS[M+H]$^+$=679

<Preparation Example 4>—Synthesis of Compound 1-4

[Compound 1-4]

Under a nitrogen atmosphere, Compound A (10.0 g, 20.58 mmol) and 2-bromo-1,1'-biphenyl (5.25 g, 22.63 mmol) were completely dissolved in 180 ml of xylene in a 500 ml-round bottom flask, and then sodium-tert-butoxide (2.57 g, 26.75 mmol) was added thereto, bis(tri-tert-butylphosphine) palladium (0.11 g, 0.21 mmol) was put thereinto, and then the resulting mixture was heated and stirred for 3 hours. The temperature was lowered to normal temperature, the resulting mixture was filtered to remove the salt, and then xylene was concentrated under reduced pressure, and the residue was recrystallized with 320 ml of ethyl acetate to prepare Compound 1-4 (10.41 g, yield: 79%).

MS[M+H]$^+$=639

<Preparation Example 5>—Synthesis of Compound 1-5

<Preparation Example 6>—Synthesis of Compound 1-6

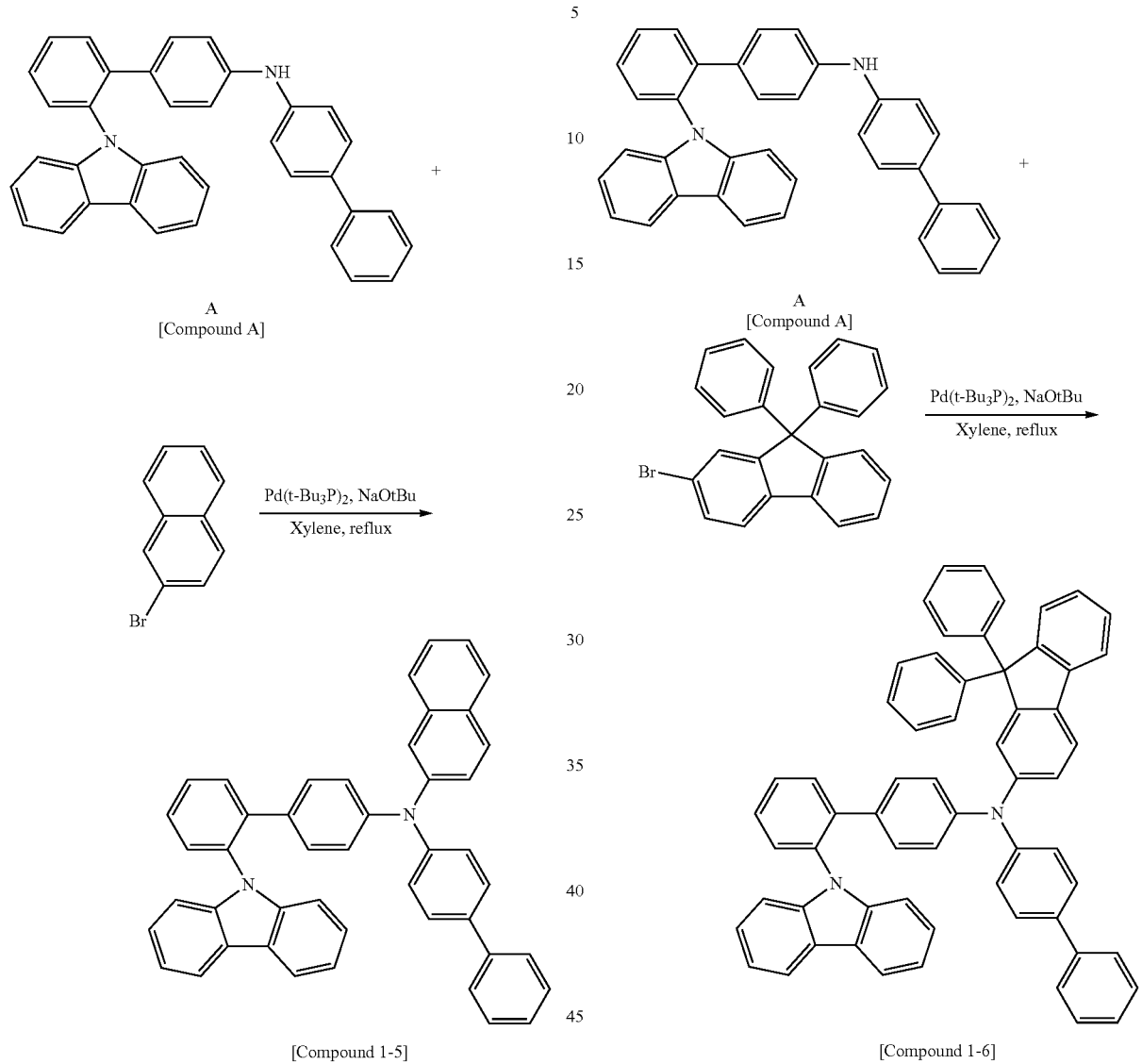

Under a nitrogen atmosphere, Compound A (10.0 g, 20.58 mmol) and 2-bromonaphthalene (4.66 g, 22.63 mmol) were completely dissolved in 120 ml of xylene in a 500 ml-round bottom flask, and then sodium-tert-butoxide (2.57 g, 26.75 mmol) was added thereto, bis(tri-tert-butylphosphine) palladium (0.11 g, 0.21 mmol) was put thereinto, and then the resulting mixture was heated and stirred for 2 hours. The temperature was lowered to normal temperature, the resulting mixture was filtered to remove the salt, and then xylene was concentrated under reduced pressure, and the residue was recrystallized with 200 ml of ethyl acetate to prepare Compound 1-5 (8.54 g, yield: 68%).

MS[M+H]$^+$=613

Under a nitrogen atmosphere, Compound A (10.0 g, 20.58 mmol) and 2-bromo-9,9-diphenyl-9H-fluorene (8.96 g, 22.63 mmol) were completely dissolved in 140 ml of xylene in a 500 ml-round bottom flask, and then sodium-tert-butoxide (2.57 g, 26.75 mmol) was added thereto, bis(tri-tert-butylphosphine) palladium (0.11 g, 0.21 mmol) was put thereinto, and then the resulting mixture was heated and stirred for 2 hours. The temperature was lowered to normal temperature, the resulting mixture was filtered to remove the salt, and then xylene was concentrated under reduced pressure, and the residue was recrystallized with 200 ml of ethyl acetate to prepare Compound 1-6 (13.76 g, yield: 83%).

MS[M+H]$^+$=803

<Preparation Example 7>—Synthesis of Compounds 1-7 to 1-12
[Compound 1-7]
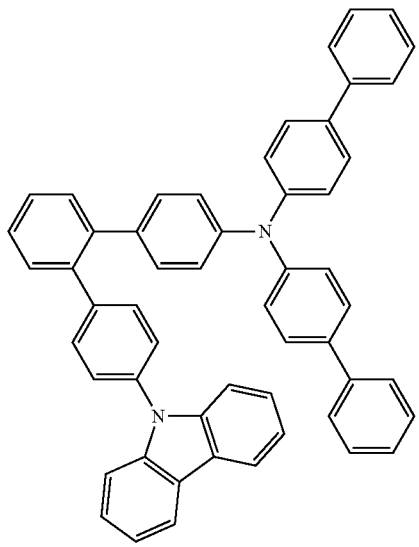
[Compound 1-8]
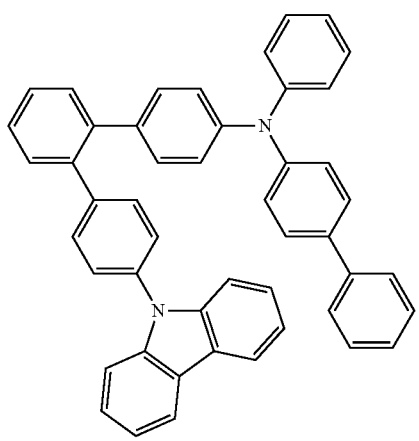
[Compound 1-9]
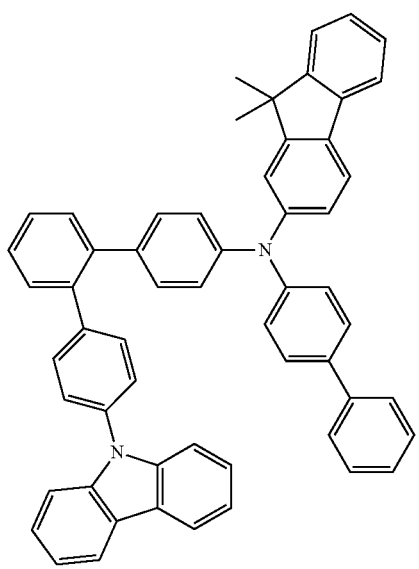
[Compound 1-10]
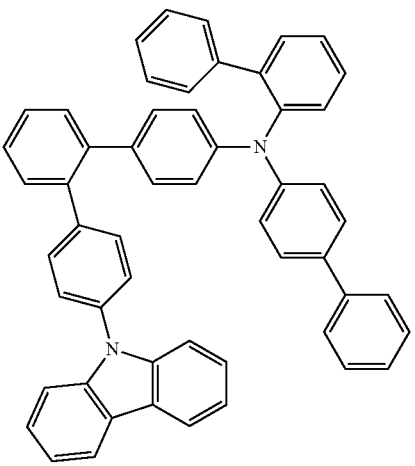
[Compound 1-11]
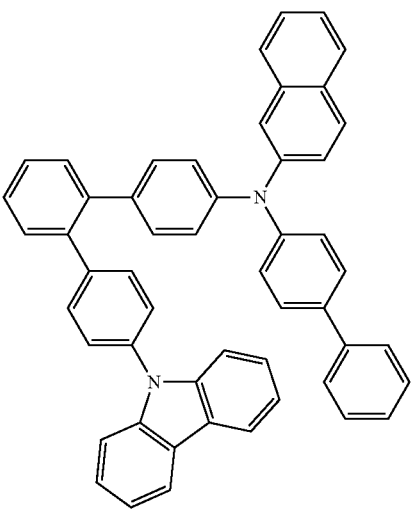
[Compound 1-12]
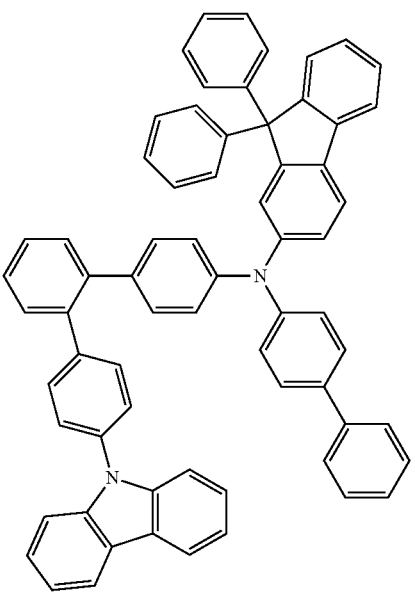

Compounds 1-7 to 1-12 were prepared by performing the same method as the methods of preparing Compounds 1-1 to 1-6, except that the following Compound E was used instead of Compound A in Preparation Examples 1 to 6.

[Compound E]

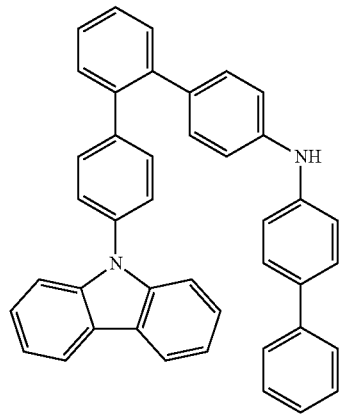

<Preparation Example 8>—Synthesis of Compound 1-13

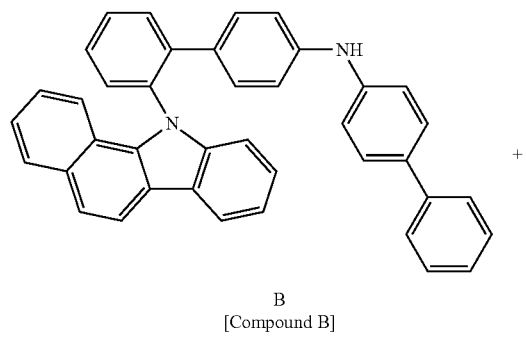

[Compound 1-13]

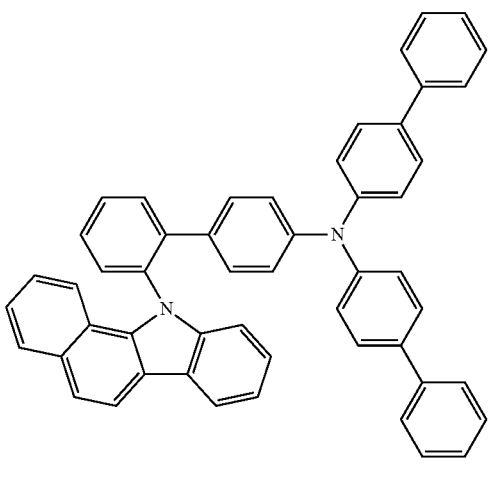

Under a nitrogen atmosphere, Compound B (10.0 g, 18.66 mmol) and 4-bromo-1,1'-biphenyl (4.76 g, 20.52 mmol) were completely dissolved in 180 ml of xylene in a 500 ml-round bottom flask, and then sodium-tert-butoxide (2.33 g, 24.26 mmol) was added thereto, bis(tri-tert-butylphosphine) palladium (0.09 g, 0.19 mmol) was put thereinto, and then the resulting mixture was heated and stirred for 5 hours. The temperature was lowered to normal temperature, the resulting mixture was filtered to remove the salt, and then xylene was concentrated under reduced pressure, and the residue was recrystallized with 320 ml of ethyl acetate to prepare Compound 1-13 (9.46 g, yield: 74%).

MS[M+H]$^+$=689

<Preparation Example 9>—Synthesis of Compound 1-14

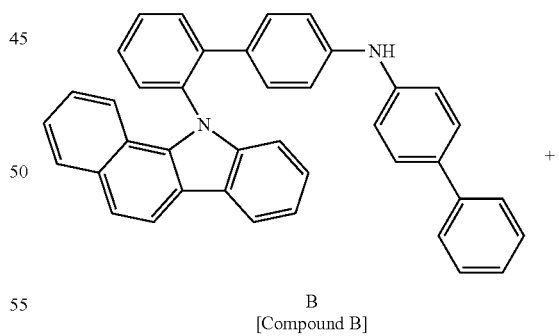

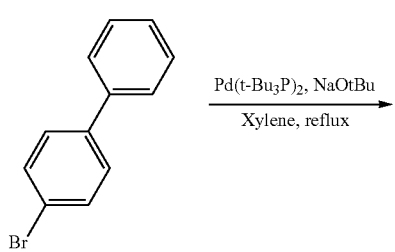

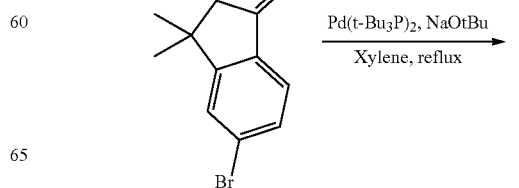

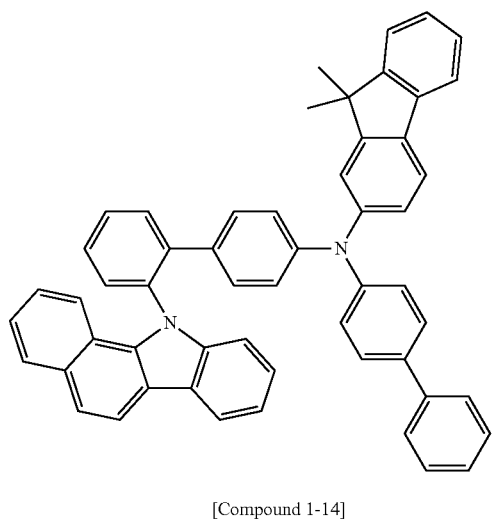

[Compound 1-14]

Under a nitrogen atmosphere, Compound B (10.0 g, 18.68 mmol) and 2-bromo-9,9-dimethyl-9H-fluorene (5.58 g, 20.52 mmol) were completely dissolved in 160 ml of xylene in a 500 ml-round bottom flask, and then sodium-tert-butoxide (2.33 g, 24.26 mmol) was added thereto, bis(tri-tert-butylphosphine) palladium (0.09 g, 0.19 mmol) was put thereinto, and then the resulting mixture was heated and stirred for 2 hours. The temperature was lowered to normal temperature, the resulting mixture was filtered to remove the salt, and then xylene was concentrated under reduced pressure, and the residue was recrystallized with 200 ml of ethyl acetate to prepare Compound 1-14 (9.88 g, yield: 70%).

MS[M+H]$^+$=729

<Preparation Example 10>—Synthesis of Compound 1-15

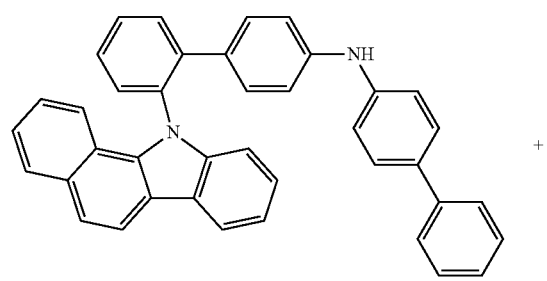

[Compound B]

B

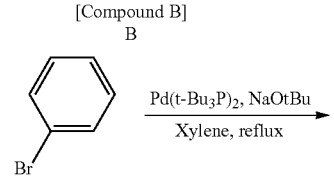

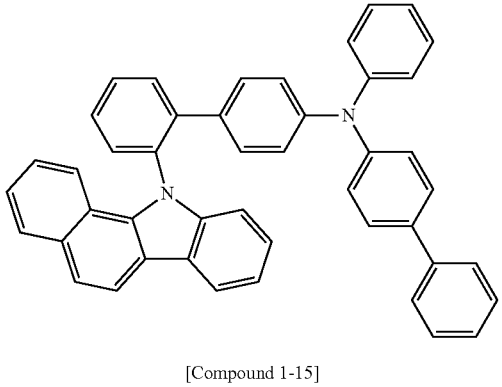

[Compound 1-15]

Under a nitrogen atmosphere, Compound B (10.0 g, 18.66 mmol) and bromobenzene (3.53 g, 3.21 mmol) were completely dissolved in 120 ml of xylene in a 500 ml-round bottom flask, and then sodium-tert-butoxide (2.33 g, 24.26 mmol) was added thereto, bis(tri-tert-butylphosphine) palladium (0.09 g, 0.19 mmol) was put thereinto, and then the resulting mixture was heated and stirred for 1 hour. The temperature was lowered to normal temperature, the resulting mixture was filtered to remove the salt, and then xylene was concentrated under reduced pressure, and the residue was recrystallized with 250 ml of ethyl acetate to prepare Compound 1-15 (8.76 g, yield: 75%).

MS[M+H]$^+$=613

<Preparation Example 11>—Synthesis of Compound 1-16

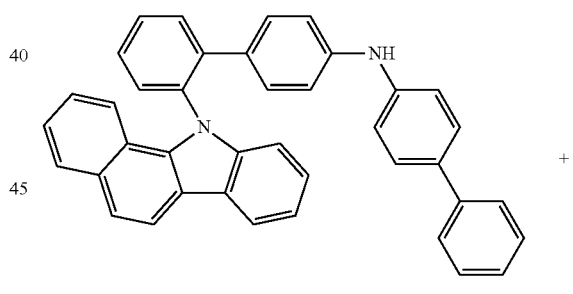

B
[Compound B]

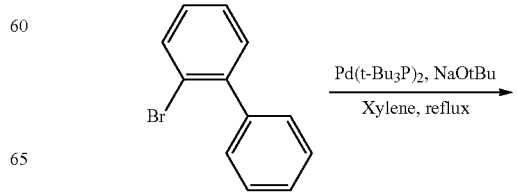

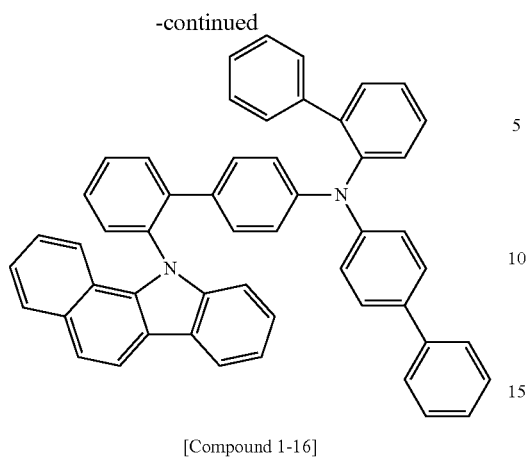

[Compound 1-16]

Under a nitrogen atmosphere, Compound B (10.0 g, 18.68 mmol) and 2-bromo-1,1'-biphenyl (5.25 g, 22.63 mmol) were completely dissolved in 180 ml of xylene in a 500 ml-round bottom flask, and then sodium-tert-butoxide (2.33 g, 24.26 mmol) was added thereto, bis(tri-tert-butylphosphine) palladium (0.09 g, 0.19 mmol) was put thereinto, and then the resulting mixture was heated and stirred for 3 hours. The temperature was lowered to normal temperature, the resulting mixture was filtered to remove the salt, and then xylene was concentrated under reduced pressure, and the residue was recrystallized with 320 ml of ethyl acetate to prepare Compound 1-16 (9.54 g, yield: 78%).

MS[M+H]$^+$=689

<Preparation Example 12>—Synthesis of Compound 1-17

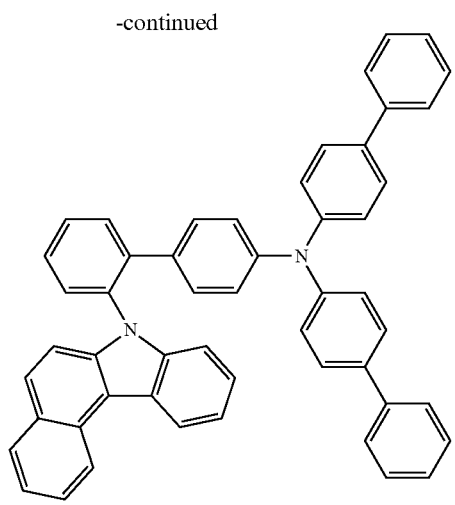

[Compound 1-17]

Under a nitrogen atmosphere, Compound D (10.0 g, 18.66 mmol) and 4-bromo-1,1'-biphenyl (4.76 g, 20.52 mmol) were completely dissolved in 180 ml of xylene in a 500 ml-round bottom flask, and then sodium-tert-butoxide (2.33 g, 24.26 mmol) was added thereto, bis(tri-tert-butylphosphine) palladium (0.09 g, 0.19 mmol) was put thereinto, and then the resulting mixture was heated and stirred for 5 hours. The temperature was lowered to normal temperature, the resulting mixture was filtered to remove the salt, and then xylene was concentrated under reduced pressure, and the residue was recrystallized with 320 ml of ethyl acetate to prepare Compound 1-17 (9.46 g, yield: 74%).

MS[M+H]$^+$=689

<Preparation Example 13>—Synthesis of Compound 1-18

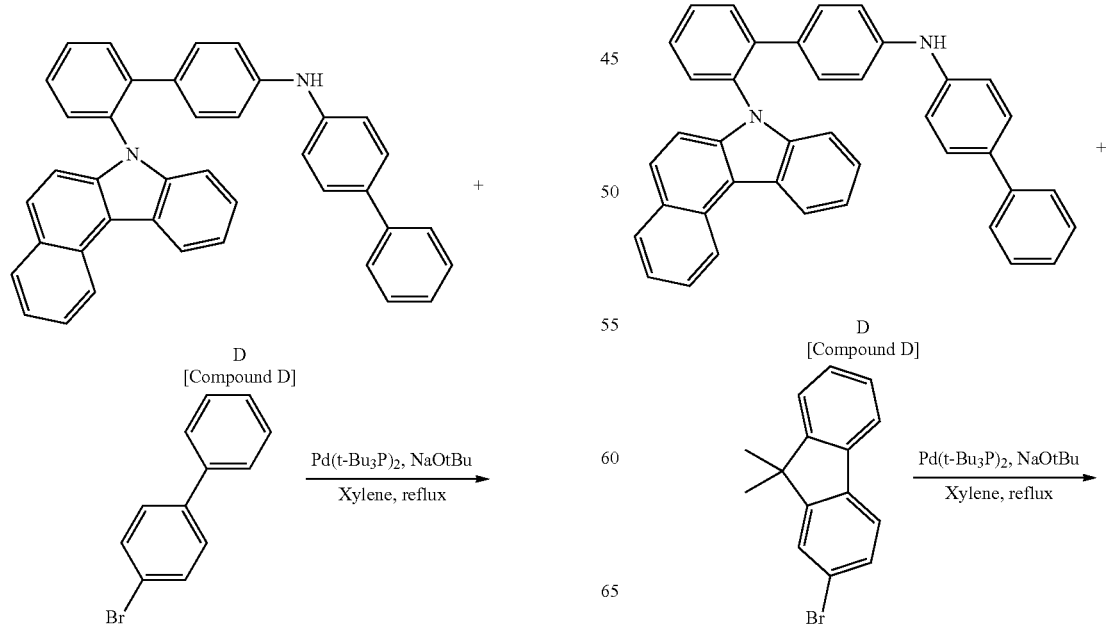

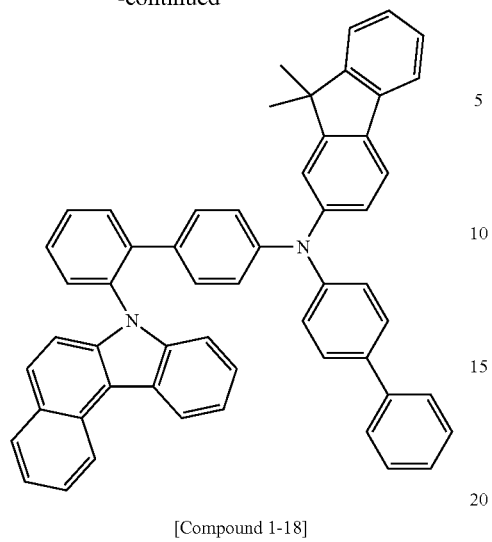

[Compound 1-18]

Under a nitrogen atmosphere, Compound D (10.0 g, 18.68 mmol) and 2-bromo-9,9-dimethyl-9H-fluorene (5.58 g, 20.52 mmol) were completely dissolved in 160 ml of xylene in a 500 ml-round bottom flask, and then sodium-tert-butoxide (2.33 g, 24.26 mmol) was added thereto, bis(tri-tert-butylphosphine) palladium (0.09 g, 0.19 mmol) was put thereinto, and then the resulting mixture was heated and stirred for 2 hours. The temperature was lowered to normal temperature, the resulting mixture was filtered to remove the salt, and then xylene was concentrated under reduced pressure, and the residue was recrystallized with 200 ml of ethyl acetate to prepare Compound 1-18 (8.91 g, yield: 63%).

MS[M+H]$^+$=729

<Preparation Example 14>—Synthesis of Compound 1-19

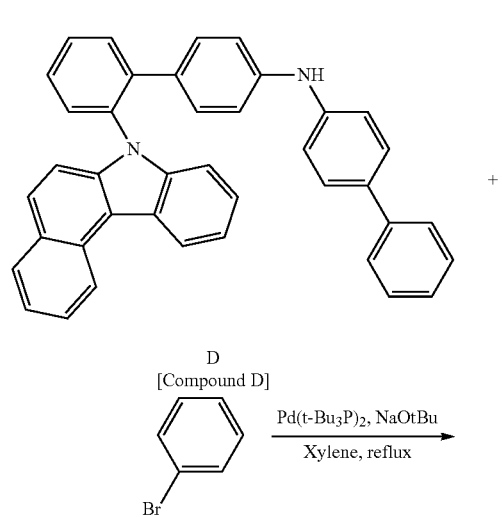

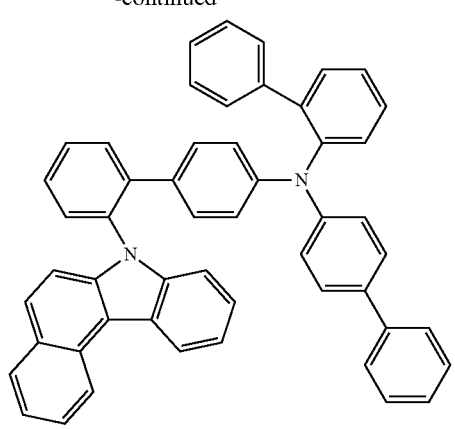

[Compound 1-19]

Under a nitrogen atmosphere, Compound D (10.0 g, 18.66 mmol) and bromobenzene (3.53 g, 3.21 mmol) were completely dissolved in 120 ml of xylene in a 500 ml-round bottom flask, and then sodium-tert-butoxide (2.33 g, 24.26 mmol) was added thereto, bis(tri-tert-butylphosphine) palladium (0.09 g, 0.19 mmol) was put thereinto, and then the resulting mixture was heated and stirred for 1 hour. The temperature was lowered to normal temperature, the resulting mixture was filtered to remove the salt, and then xylene was concentrated under reduced pressure, and the residue was recrystallized with 200 ml of ethyl acetate to prepare Compound 1-19 (7.89 g, yield: 68%).

MS[M+H]=613

<Preparation Example 15>—Synthesis of Compound 1-20

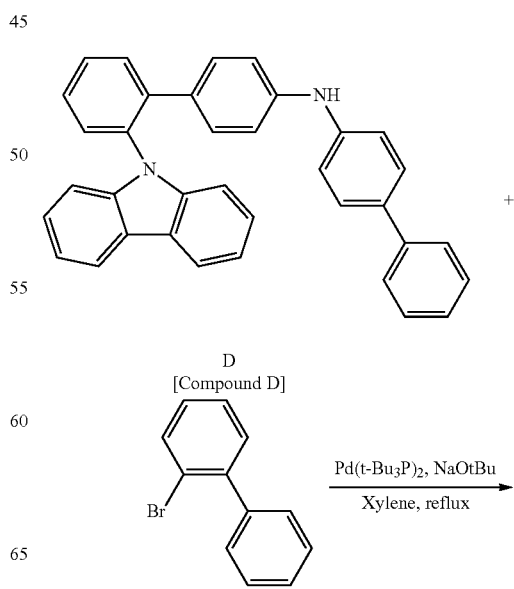

[Compound 1-20]

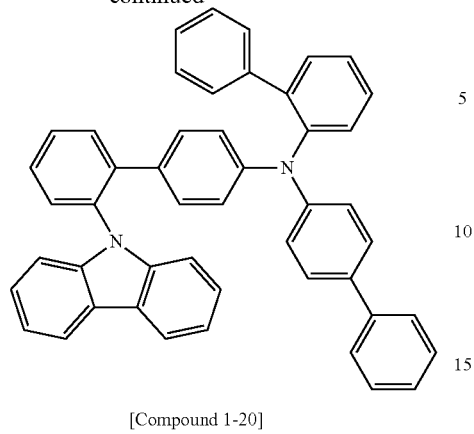

[Compound 1-22]

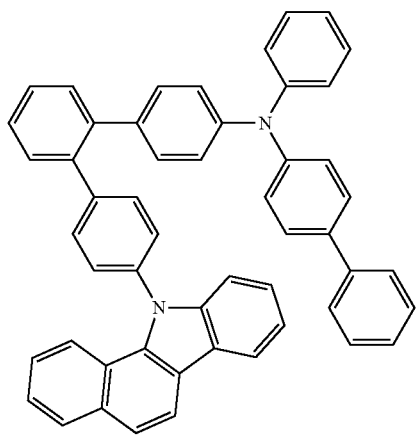

Under a nitrogen atmosphere, Compound D (10.0 g, 18.68 mmol) and 2-bromo-1,1'-biphenyl (5.25 g, 22.63 mmol) were completely dissolved in 180 ml of xylene in a 500 ml-round bottom flask, and then sodium-tert-butoxide (2.33 g, 24.26 mmol) was added thereto, bis(tri-tert-butylphosphine) palladium (0.09 g, 0.19 mmol) was put thereinto, and then the resulting mixture was heated and stirred for 3 hours. The temperature was lowered to normal temperature, the resulting mixture was filtered to remove the salt, and then xylene was concentrated under reduced pressure, and the residue was recrystallized with 320 ml of ethyl acetate to prepare Compound 1-20 (8.69 g, yield: 71%).

MS[M+H]$^+$=689

<Preparation Example 16>—Synthesis of Compounds 1-21 to 1-26

[Compound 1-23]

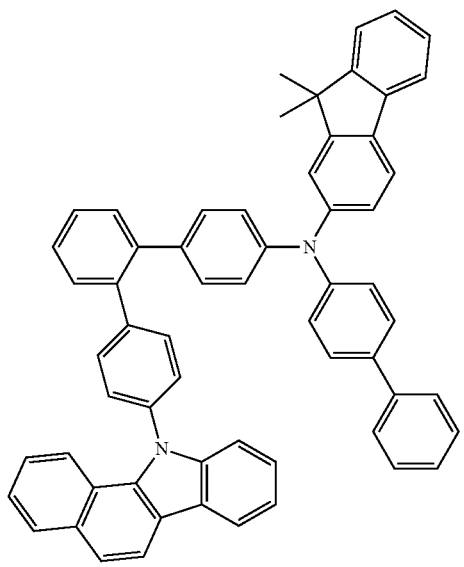

[Compound 1-21]

[Compound 1-24]

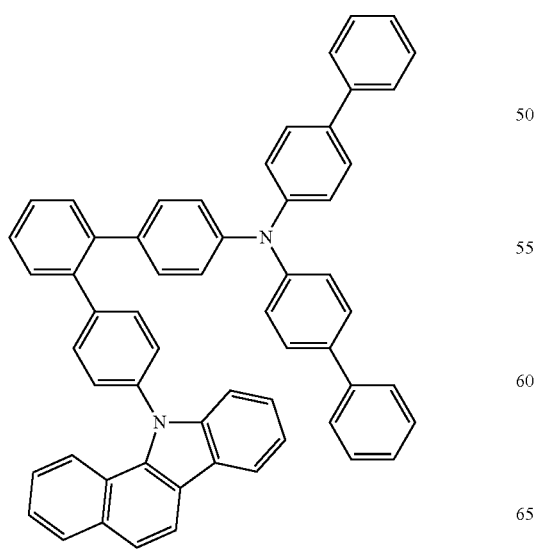

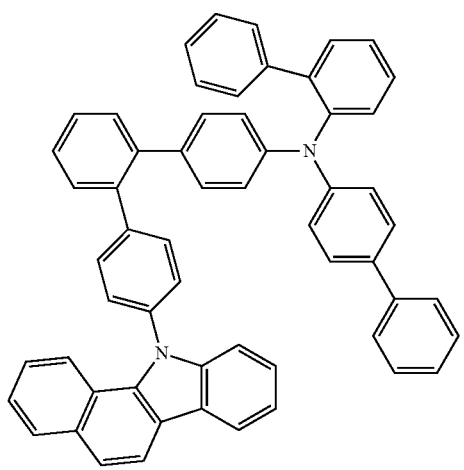

[Compound 1-25]
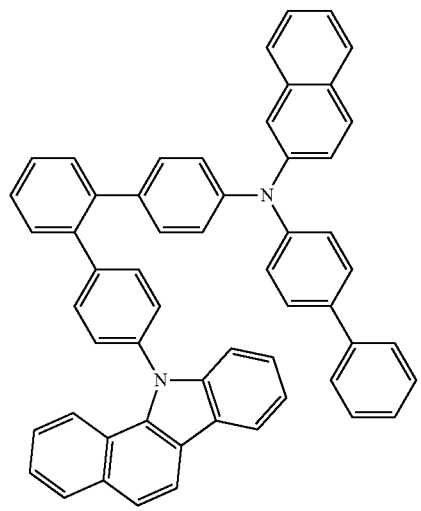
[Compound F]
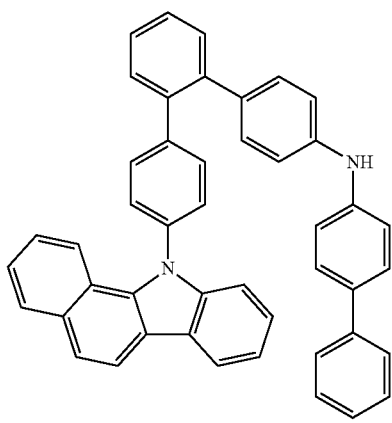
[Compound 1-26]
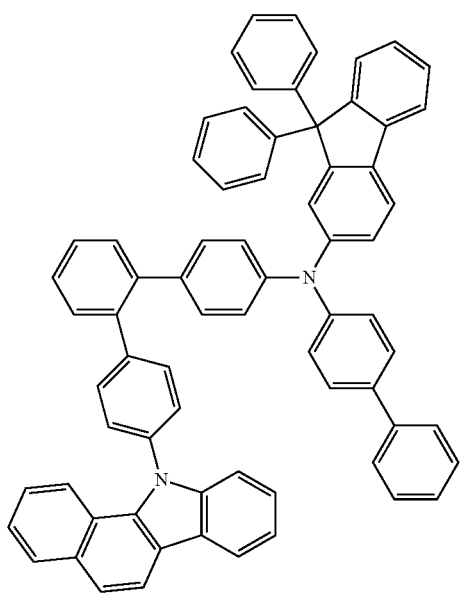
Compounds 1-21 to 1-26 were prepared by performing the same method as the methods of preparing Compounds 1-7 to 1-12, except that the following Compound F was used instead of Compound E in Preparation Example 7.
<Preparation Example 17>—Synthesis of Compounds 1-27 to 1-32
[Compound 1-27]
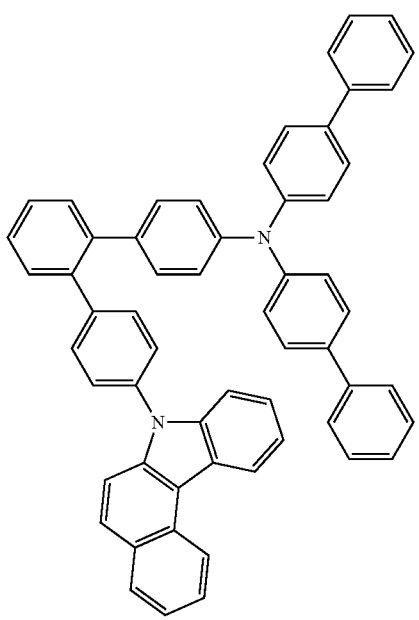

[Compound 1-28]
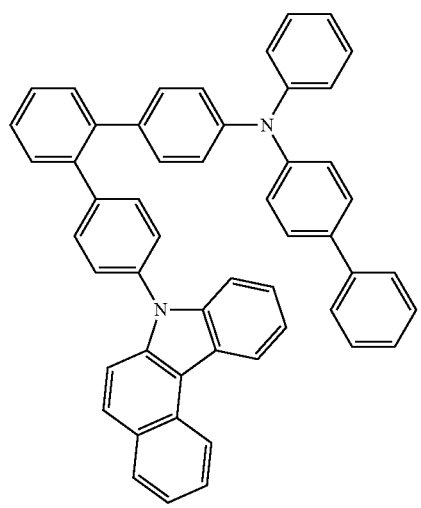
[Compound 1-30]
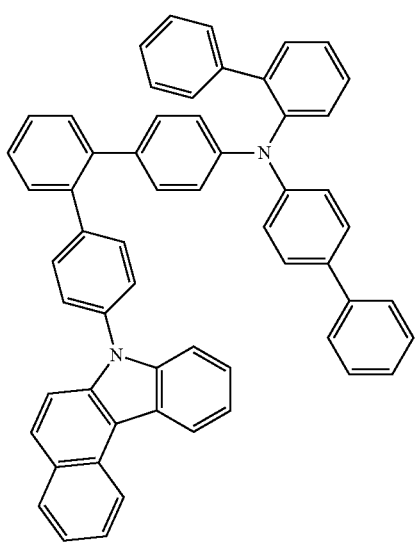
[Compound 1-29]
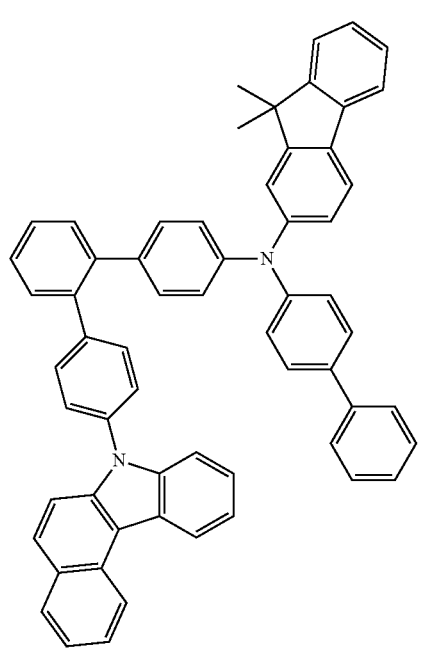
[Compound 1-31]
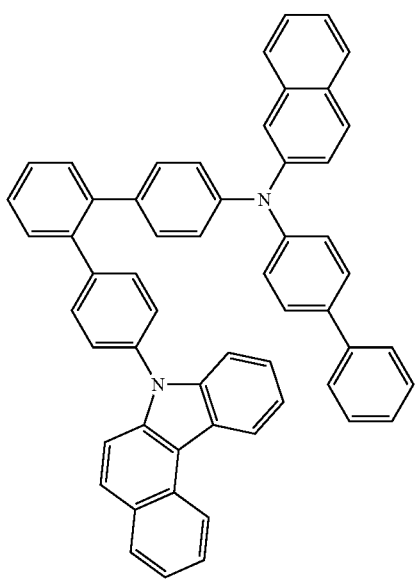

-continued

[Compound 1-32]

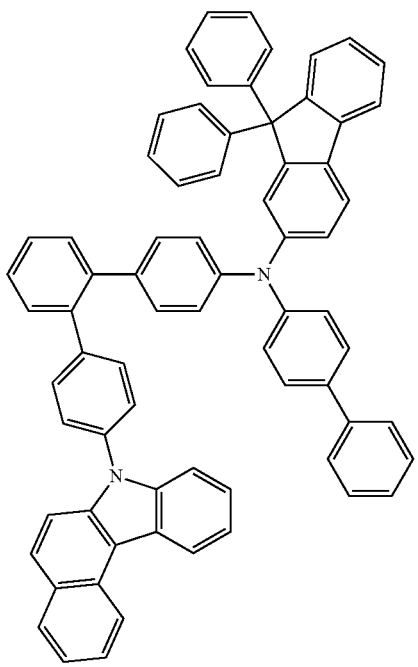

Compounds 1-27 to 1-32 were prepared by performing the same method as the methods of preparing Compounds 1-7 to 1-12, except that the following Compound H was used instead of Compound E in Preparation Example 7.

[Compound H]

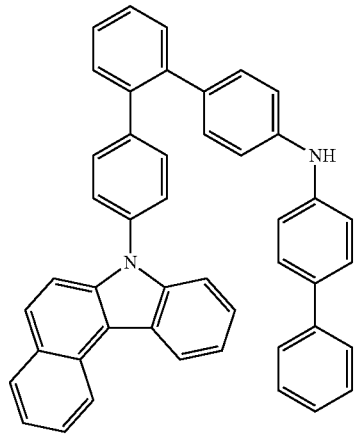

H

Experimental Example 1

Experimental Example 1-1

A glass substrate thinly coated with indium tin oxide (ITO) to have a thickness of 1,000 Å was put into distilled water in which a detergent was dissolved, and ultrasonically washed. In this case, a product manufactured by Fischer Co., was used as the detergent, and distilled water twice filtered using a filter manufactured by Millipore Co., was used as the distilled water. After the ITO was washed for 30 minutes, ultrasonic washing was conducted twice repeatedly using distilled water for 10 minutes. After the washing using distilled water was completed, ultrasonic washing was conducted using isopropyl alcohol, acetone, and methanol solvents, and drying was conducted, and then the substrate was transferred to a plasma cleaner. In addition, the substrate was cleaned using oxygen plasma for 5 minutes, and then transferred to a vacuum evaporator.

Hexanitrile hexaazatriphenylene (HAT) of the following Chemical Formula was thermally vacuum deposited to have a thickness of 500 Å on the transparent ITO electrode, which was thus prepared, thereby forming a hole injection layer.

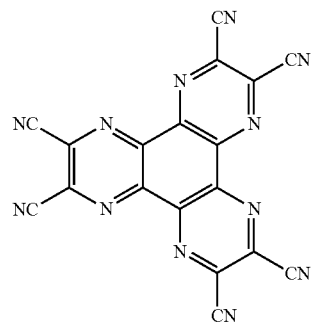

[HAT]

The following compound 4-4'-bis[N-(1-naphthyl)-N-phenylamino]biphenyl (NPB) (300 Å), which is a material for transporting holes, was vacuum deposited on the hole injection layer, thereby forming a hole transport layer.

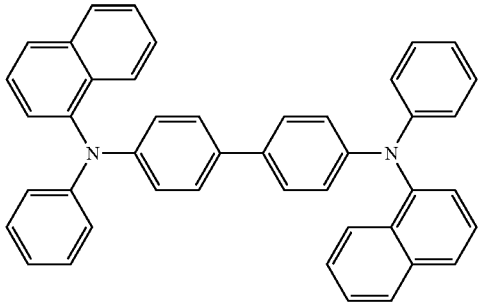

[NPB]

Subsequently, the following Compound 1-1 was vacuum deposited to have a film thickness of 100 Å on the hole transport layer, thereby forming an electron blocking layer.

[Compound 1-1]

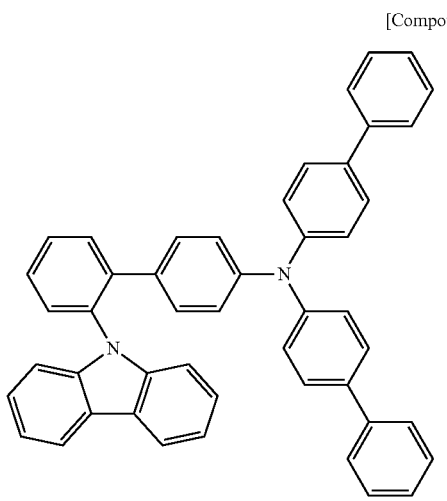

Subsequently, the following BH and BD were vacuum deposited at a weight ratio of 25:1 to have a film thickness of 300 Å on the electron blocking layer, thereby forming a light emitting layer.

[BH]

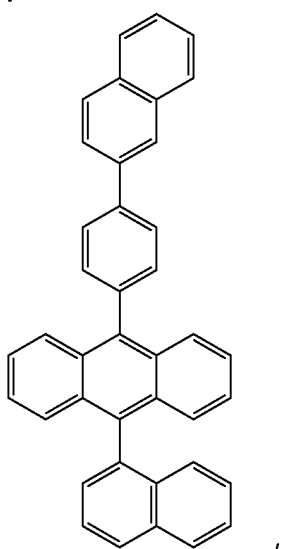

[BD]

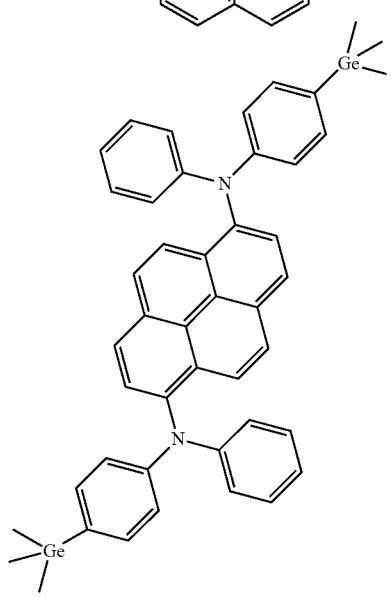

[ET1]

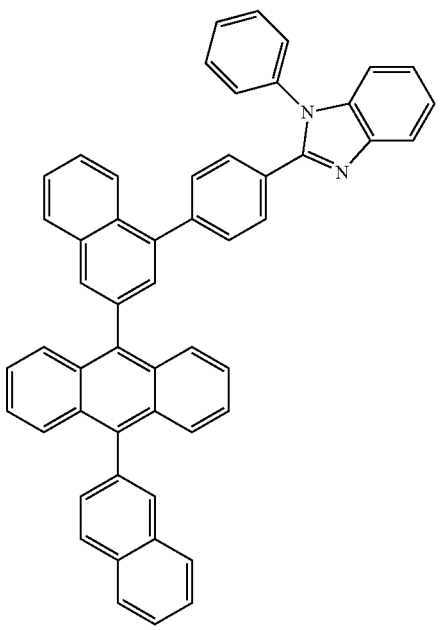

[LiQ]

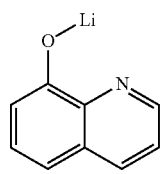

Compound ET1 and Compound LiQ (lithium quinolate) were vacuum deposited at a weight ratio of 1:1 on the light emitting layer, thereby forming an electron injection and transport layer having a thickness of 300 Å. Lithium fluoride (LiF) and aluminum were sequentially deposited to have a thickness of 12 Å and 2,000 Å, respectively, on the electron injection and transport layer, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^7$ to $5 \times 10^6$ torr, thereby manufacturing an organic light emitting device.

Experimental Example 1-2

An organic light emitting device was manufactured in the same manner as in Experimental Example 1-1, except that Compound 1-2 was used instead of Compound 1-1 in Experimental Example 1-1.

Experimental Example 1-3

An organic light emitting device was manufactured in the same manner as in Experimental Example 1-1, except that Compound 1-3 was used instead of Compound 1-1 in Experimental Example 1-1.

Experimental Example 1-4

An organic light emitting device was manufactured in the same manner as in Experimental Example 1-1, except that Compound 1-4 was used instead of Compound 1-1 in Experimental Example 1-1.

Experimental Example 1-5

An organic light emitting device was manufactured in the same manner as in Experimental Example 1-1, except that Compound 1-5 was used instead of Compound 1-1 in Experimental Example 1-1.

Experimental Example 1-6

An organic light emitting device was manufactured in the same manner as in Experimental Example 1-1, except that Compound 1-6 was used instead of Compound 1-1 in Experimental Example 1-1.

Experimental Example 1-7

An organic light emitting device was manufactured in the same manner as in Experimental Example 1-1, except that Compound 1-11 was used instead of Compound 1-1 in Experimental Example 1-1.

Experimental Example 1-8

An organic light emitting device was manufactured in the same manner as in Experimental Example 1-1, except that Compound 1-12 was used instead of Compound 1-1 in Experimental Example 1-1.

Experimental Example 1-9

An organic light emitting device was manufactured in the same manner as in Experimental Example 1-1, except that Compound 1-14 was used instead of Compound 1-1 in Experimental Example 1-1.

Experimental Example 1-10

An organic light emitting device was manufactured in the same manner as in Experimental Example 1-1, except that Compound 1-15 was used instead of Compound 1-1 in Experimental Example 1-1.

Experimental Example 1-11

An organic light emitting device was manufactured in the same manner as in Experimental Example 1-1, except that Compound 1-19 was used instead of Compound 1-1 in Experimental Example 1-1.

Experimental Example 1-12

An organic light emitting device was manufactured in the same manner as in Experimental Example 1-1, except that Compound 1-20 was used instead of Compound 1-1 in Experimental Example 1-1.

Experimental Example 1-13

An organic light emitting device was manufactured in the same manner as in Experimental Example 1-1, except that Compound 1-21 was used instead of Compound 1-1 in Experimental Example 1-1.

Experimental Example 1-14

An organic light emitting device was manufactured in the same manner as in Experimental Example 1-1, except that Compound 1-24 was used instead of Compound 1-1 in Experimental Example 1-1.

Experimental Example 1-15

An organic light emitting device was manufactured in the same manner as in Experimental Example 1-1, except that Compound 1-28 was used instead of Compound 1-1 in Experimental Example 1-1.

Experimental Example 1-16

An organic light emitting device was manufactured in the same manner as in Experimental Example 1-1, except that Compound 1-29 was used instead of Compound 1-1 in Experimental Example 1-1.

Comparative Example 1-1

An organic light emitting device was manufactured in the same manner as in Experimental Example 1-1, except that the following EB 1 was used instead of Compound 1-1 in Experimental Example 1-1.

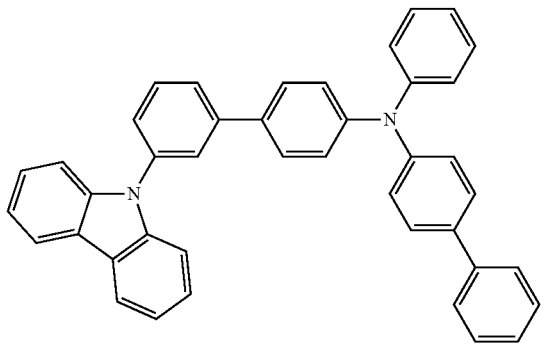

[EB 1]

Comparative Example 1-2

An organic light emitting device was manufactured in the same manner as in Experimental Example 1-1, except that the following EB 2 was used instead of Compound 1-1 in Experimental Example 1-1.

[EB 2]

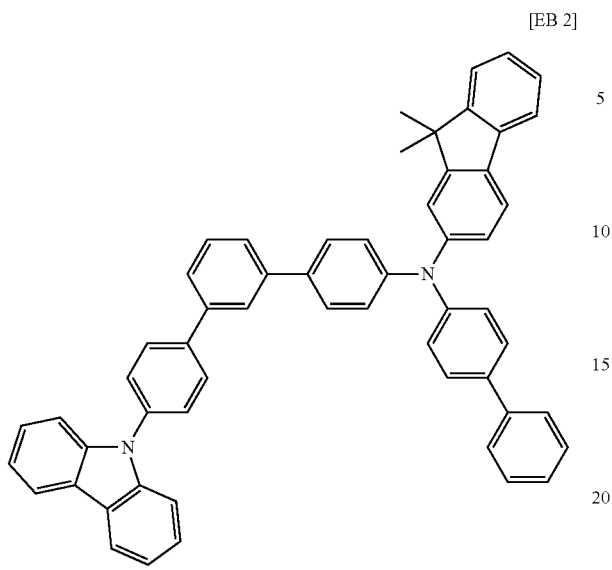

Comparative Example 1-3

An organic light emitting device was manufactured in the same manner as in Experimental Example 1-1, except that the following EB 3 was used instead of Compound 1-1 in Experimental Example 1-1.

[EB 3]

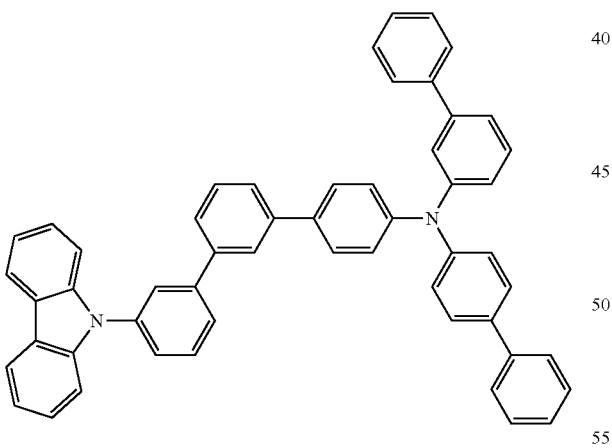

Comparative Example 1-4

An organic light emitting device was manufactured in the same manner as in Experimental Example 1-1, except that the following EB 4 was used instead of Compound 1-1 in Experimental Example 1-1.

[EB 4]

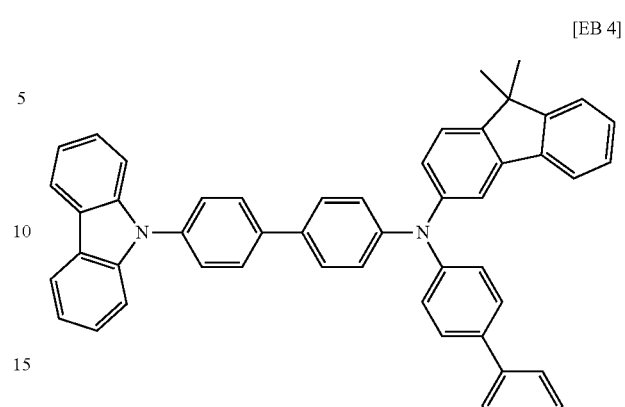

Comparative Example 1-5

An organic light emitting device was manufactured in the same manner as in Experimental Example 1-1, except that the following EB 5 was used instead of Compound 1-1 in Experimental Example 1-1.

[EB 5]

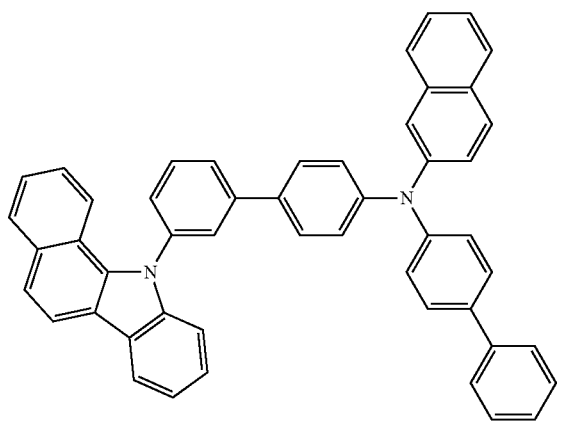

When current was applied to the organic light emitting devices manufactured in Experimental Examples 1-1 to 1-16 and Comparative Examples 1-1 to 1-5, the results of the following Table 1 were obtained.

TABLE 1

| Classification | Compound (Electron blocking layer) | Voltage (V@10 mA/cm$^2$) | Efficiency (cd/A@10 mA/cm$^2$) | Color coordinate (x, y) |
|---|---|---|---|---|
| Experimental Example 1-1 | Compound 1-1 | 3.62 | 5.75 | (0.137, 0.126) |
| Experimental Example 1-2 | Compound 1-2 | 3.52 | 5.88 | (0.137, 0.126) |
| Experimental Example 1-3 | Compound 1-3 | 3.57 | 5.81 | (0.137, 0.127) |
| Experimental Example 1-4 | Compound 1-4 | 3.58 | 5.82 | (0.137, 0.126) |
| Experimental Example 1-5 | Compound 1-5 | 3.61 | 5.73 | (0.137, 0.125) |
| Experimental Example 1-6 | Compound 1-6 | 3.54 | 5.87 | (0.137, 0.126) |
| Experimental Example 1-7 | Compound 1-11 | 3.63 | 5.68 | (0.137, 0.126) |
| Experimental Example 1-8 | Compound 1-12 | 3.64 | 5.51 | (0.137, 0.126) |
| Experimental Example 1-9 | Compound 1-14 | 3.73 | 5.68 | (0.138, 0.126) |
| Experimental Example 1-10 | Compound 1-15 | 3.78 | 5.52 | (0.137, 0.126) |
| Experimental Example 1-11 | Compound 1-19 | 3.65 | 5.67 | (0.137, 0.126) |
| Experimental Example 1-12 | Compound 1-20 | 3.73 | 5.65 | (0.137, 0.126) |
| Experimental Example 1-13 | Compound 1-21 | 3.71 | 5.48 | (0.138, 0.126) |
| Experimental Example 1-14 | Compound 1-24 | 3.82 | 5.41 | (0.137, 0.126) |
| Experimental Example 1-15 | Compound 1-28 | 3.88 | 5.42 | (0.136, 0.127) |
| Experimental Example 1-16 | Compound 1-29 | 3.87 | 5.43 | (0.135, 0.127) |
| Comparative Example 1-1 | EB 1 | 4.24 | 4.93 | (0.138, 0.127) |
| Comparative Example 1-2 | EB 2 | 4.33 | 4.81 | (0.139, 0.125) |
| Comparative Example 1-3 | EB 3 | 4.40 | 4.61 | (0.139, 0.126) |
| Comparative Example 1-4 | EB 4 | 4.52 | 4.46 | (0.139, 0.125) |
| Comparative Example 1-5 | EB 5 | 4.68 | 4.32 | (0.139, 0.125) |

As observed in Table 1, it can be seen that when the compounds in Experimental Examples 1-1 to 1-16 were used as an electron blocking layer in an organic light emitting device, the compounds exhibited lower voltage and higher efficiency characteristics than the materials in Comparative Examples 1-1 to 1-5.

Specifically, when Experimental Examples 1-1 to 1-6 and Comparative Examples 1-1 and 1-4 were compared with each other, it can be confirmed that the case where a carbazole is directly substituted at the ortho position in a benzene ring had an effect of a 10 to 15% lower driving voltage and a 20% higher light efficiency than the case where the carbazole is substituted at the meta and para positions in the benzene ring.

Further, when Experimental Examples 1-7 and 1-8 and Comparative Examples 1-2 and 1-3 were compared with each other, the case where the carbazole is directly substituted at the ortho position exhibited a lower driving voltage and a higher efficiency than the case where the carbazole is substituted at the meta and para positions, even when there is a linking group (linker) between the benzene ring and the carbazole structure. It can be seen that this tendency was shown even in Experimental Examples 1-9 to 1-12 and Comparative Example 1-5 where a benzocarbazole in which a benzene ring is fused is substituted.

Therefore, it could be confirmed that the compound derivatives of the Chemical Formulae according to the present specification have excellent electron blocking capability, and thus exhibit low voltage and high efficiency characteristics, and may be applied to an organic light emitting device.

Experimental Example 2

Experimental Example 2-1

An experiment was performed in the same manner as in Experimental Example 1-1, except that in Experimental Example 1, the following compound TCTA was used as an electron blocking layer, and Compound 1-1 was used instead of NPB as a hole transport layer.

[TCTA]

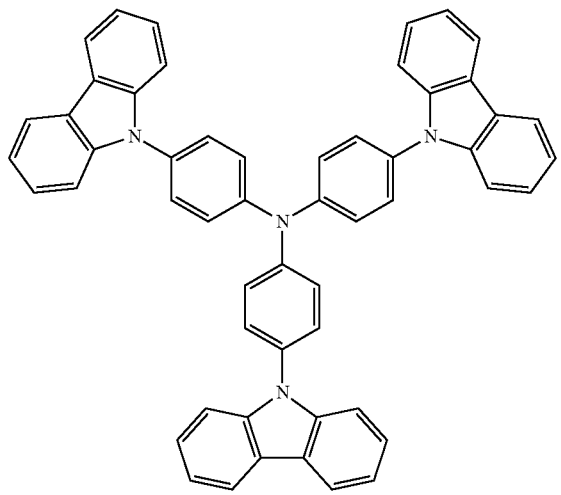

Experimental Example 2-2

An experiment was performed in the same manner as in Experimental Example 1-1, except that in Experimental Example 1, Compound TCTA was used as an electron blocking layer, and Compound 1-2 was used instead of NPB as a hole transport layer.

Experimental Example 2-3

An experiment was performed in the same manner as in Experimental Example 1-1, except that in Experimental Example 1, Compound TCTA was used as an electron blocking layer, and Compound 1-3 was used instead of NPB as a hole transport layer.

Experimental Example 2-4

An experiment was performed in the same manner as in Experimental Example 1-1, except that in Experimental Example 1, Compound TCTA was used as an electron blocking layer, and Compound 1-4 was used instead of NPB as a hole transport layer.

Experimental Example 2-5

An experiment was performed in the same manner as in Experimental Example 1-1, except that in Experimental Example 1, Compound TCTA was used as an electron blocking layer, and Compound 1-5 was used instead of NPB as a hole transport layer.

Experimental Example 2-6

An experiment was performed in the same manner as in Experimental Example 1-1, except that in Experimental Example 1, Compound TCTA was used as an electron blocking layer, and Compound 1-6 was used instead of NPB as a hole transport layer.

Experimental Example 2-7

An experiment was performed in the same manner as in Experimental Example 1-1, except that in Experimental Example 1, Compound TCTA was used as an electron blocking layer, and Compound 1-9 was used instead of NPB as a hole transport layer.

Experimental Example 2-8

An experiment was performed in the same manner as in Experimental Example 1-1, except that in Experimental Example 1, Compound TCTA was used as an electron blocking layer, and Compound 1-10 was used instead of NPB as a hole transport layer.

Experimental Example 2-9

An experiment was performed in the same manner as in Experimental Example 1-1, except that in Experimental Example 1, Compound TCTA was used as an electron blocking layer, and Compound 1-13 was used instead of NPB as a hole transport layer.

Experimental Example 2-10

An experiment was performed in the same manner as in Experimental Example 1-1, except that in Experimental Example 1, Compound TCTA was used as an electron blocking layer, and Compound 1-16 was used instead of NPB as a hole transport layer.

Experimental Example 2-11

An experiment was performed in the same manner as in Experimental Example 1-1, except that in Experimental Example 1, Compound TCTA was used as an electron blocking layer, and Compound 1-17 was used instead of NPB as a hole transport layer.

Experimental Example 2-12

An experiment was performed in the same manner as in Experimental Example 1-1, except that in Experimental Example 1, Compound TCTA was used as an electron blocking layer, and Compound 1-18 was used instead of NPB as a hole transport layer.

Experimental Example 2-13

An experiment was performed in the same manner as in Experimental Example 1-1, except that in Experimental Example 1, Compound TCTA was used as an electron blocking layer, and Compound 1-22 was used instead of NPB as a hole transport layer.

Experimental Example 2-14

An experiment was performed in the same manner as in Experimental Example 1-1, except that in Experimental Example 1, Compound TCTA was used as an electron blocking layer, and Compound 1-23 was used instead of NPB as a hole transport layer.

Experimental Example 2-15

An experiment was performed in the same manner as in Experimental Example 1-1, except that in Experimental Example 1, Compound TCTA was used as an electron blocking layer, and Compound 1-31 was used instead of NPB as a hole transport layer.

Experimental Example 2-16

An experiment was performed in the same manner as in Experimental Example 1-1, except that in Experimental Example 1, Compound TCTA was used as an electron blocking layer, and Compound 1-32 was used instead of NPB as a hole transport layer.

Comparative Example 2-1

An experiment was performed in the same manner as in Experimental Example 1-1, except that in Experimental Example 1, TCTA was used as an electron blocking layer, and the following HT 1 was used as a hole transport layer.

[HT 1]

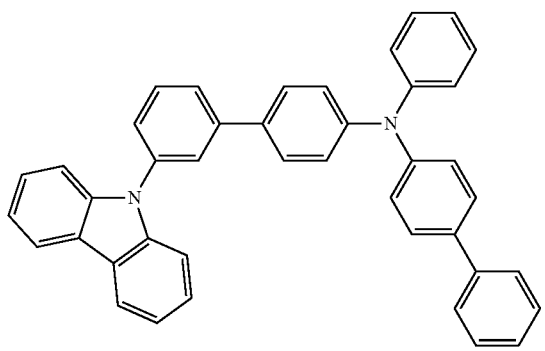

Comparative Example 2-2

An experiment was performed in the same manner as in Experimental Example 1-1, except that in Experimental Example 1, TCTA was used as an electron blocking layer, and the following HT 2 was used as a hole transport layer.

[HT 2]

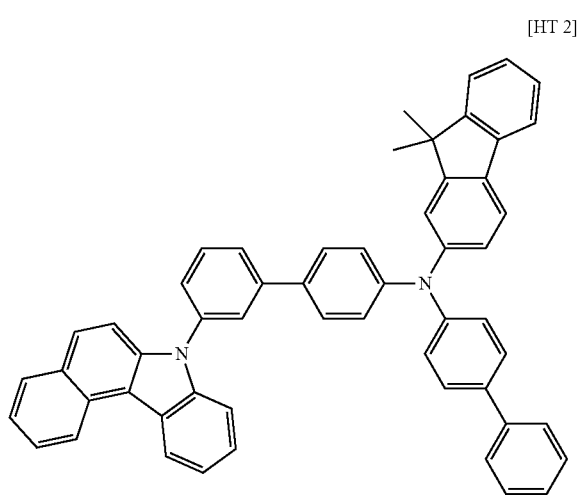 [SMILES: CC1(C)c2ccccc2-c2ccc(N(c3ccc(-c4ccccc4)cc3)c3ccc(-c4cccc(-n5c6ccccc6c6c7ccccc7ccc65)c4)cc3)cc21]

Comparative Example 2-3

An experiment was performed in the same manner as in Experimental Example 1-1, except that in Experimental Example 1, TCTA was used as an electron blocking layer, and the following HT 3 was used as a hole transport layer.

[HT 3]

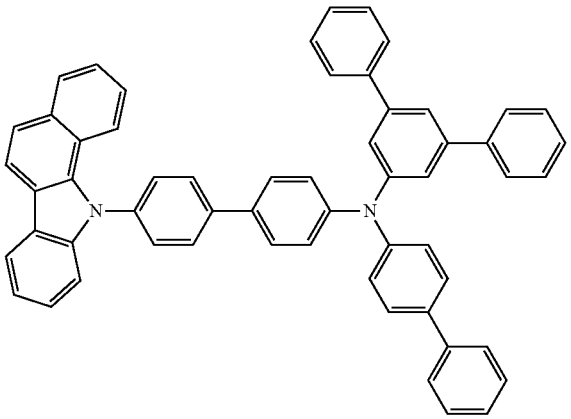

Comparative Example 2-4

An experiment was performed in the same manner as in Experimental Example 1-1, except that in Experimental Example 1, TCTA was used as an electron blocking layer, and the following HT 4 was used as a hole transport layer.

[HT 4]

When current was applied to the organic light emitting devices manufactured in Experimental Examples 2-1 to 2-16 and Comparative Examples 2-1 to 2-4, the results of the following Table 2 were obtained.

TABLE 2

| Classification | Compound (Hole transport layer) | Voltage (V@10 mA/cm$^2$) | Efficiency (cd/A@10 mA/cm$^2$) | Color coordinate (x, y) |
|---|---|---|---|---|
| Experimental Example 2-1 | Compound 1-1 | 4.15 | 5.55 | (0.139, 0.122) |
| Experimental Example 2-2 | Compound 1-2 | 4.02 | 5.68 | (0.138, 0.126) |
| Experimental Example 2-3 | Compound 1-3 | 3.87 | 6.05 | (0.138, 0.127) |
| Experimental Example 2-4 | Compound 1-4 | 3.88 | 6.04 | (0.137, 0.125) |
| Experimental Example 2-5 | Compound 1-5 | 3.89 | 6.02 | (0.136, 0.125) |
| Experimental Example 2-6 | Compound 1-6 | 3.84 | 5.93 | (0.136, 0.127) |
| Experimental Example 2-7 | Compound 1-9 | 3.83 | 6.00 | (0.136, 0.125) |
| Experimental Example 2-8 | Compound 1-10 | 3.84 | 5.90 | (0.137, 0.125) |
| Experimental Example 2-9 | Compound 1-13 | 3.93 | 5.81 | (0.138, 0.125) |
| Experimental Example 2-10 | Compound 1-16 | 3.98 | 5.72 | (0.136, 0.125) |
| Experimental Example 2-11 | Compound 1-17 | 3.93 | 5.85 | (0.137, 0.125) |
| Experimental Example 2-12 | Compound 1-18 | 3.95 | 5.75 | (0.136, 0.125) |
| Experimental Example 2-13 | Compound 1-22 | 4.02 | 5.88 | (0.138, 0.126) |
| Experimental Example 2-14 | Compound 1-23 | 3.97 | 5.81 | (0.137, 0.125) |
| Experimental Example 2-15 | Compound 1-31 | 4.00 | 5.72 | (0.136, 0.127) |
| Experimental Example 2-16 | Compound 1-32 | 4.01 | 5.82 | (0.135, 0.127) |
| Comparative Example 2-1 | HT 1 | 4.60 | 4.87 | (0.138, 0.127) |
| Comparative Example 2-2 | HT 2 | 4.61 | 4.79 | (0.139, 0.125) |
| Comparative Example 2-3 | HT 3 | 4.79 | 4.68 | (0.139, 0.126) |
| Comparative Example 2-4 | HT 4 | 4.86 | 4.55 | (0.139, 0.127) |

As observed in Table 2, it can be seen that when the compounds in Experimental Examples 2-1 to 2-16 are used as a hole transport layer in an organic light emitting device, the compounds exhibited lower voltage and higher efficiency characteristics than those in Comparative Examples 2-1 to 2-4.

Specifically, when Experimental Examples 2-1 to 2-6 and Comparative Examples 2-1 and 2-4 were compared with each other, it could be confirmed that the case where a carbazole is directly substituted at the ortho position in a benzene ring had an effect of a 8 to 10% lower driving voltage and a 20 to 25% higher light efficiency than the case where the carbazole is substituted at the meta and para positions in the benzene ring.

Further, when Experimental Examples 2-7 and 2-8 and Comparative Example 2-4 were compared with each other, the case where the carbazole is directly substituted at the ortho position exhibited a lower driving voltage and a higher efficiency than those when the carbazole is substituted at the meta position, even when there is a linking group (linker) between the benzene ring and the carbazole structure. It can be seen that this tendency was shown even in Experimental Examples 2-9 to 2-12 and Comparative Examples 2-2 and 2-3 where a benzocarbazole in which a benzene ring is fused is substituted.

Therefore, it can be confirmed that the compound derivatives of the Chemical Formulae according to the present specification also have excellent hole transporting capability, and thus exhibit low voltage and high efficiency characteristics, and may be applied to an organic light emitting device.

Although the preferred exemplary embodiments (an electron blocking layer and a hole transport layer) of the present invention have been described above, the present invention is not limited thereto, and various modifications can be made and carried out within the scope of the claims and the detailed description of the invention, and also fall within the scope of the invention.

EXPLANATION OF REFERENCE NUMERALS AND SYMBOLS

10, 11: Organic light emitting device
20: Substrate
30: First electrode
40: Light emitting layer
50: Second electrode
60: Hole injection layer
70: Hole transport layer
80: Electron transport layer
90: Electron injection layer

The invention claimed is:
1. A compound represented by the following Chemical Formula 1:

[Chemical Formula 1]

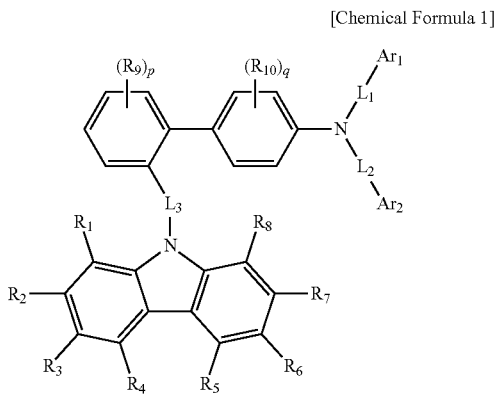

in Chemical Formula 1,
$L_1$ to $L_3$ are the same as or different from each other, and are each independently a direct bond; or a substituted or unsubstituted arylene group,
$Ar_1$ and $Ar_2$ are the same as or different from each other, and are each independently hydrogen; deuterium; a halogen group; a cyano group; a nitro group; a substituted or unsubstituted silyl group; a substituted or unsubstituted alkyl group; a substituted or unsubstituted cycloalkyl group; or a substituted or unsubstituted aryl group,
$R_1$ to $R_8$ are the same as or different from each other, and are each independently hydrogen; deuterium; a halogen group; a cyano group; a substituted or unsubstituted alkyl group; or a substituted or unsubstituted aryl group, or optionally combine with an adjacent group to form a substituted or unsubstituted ring,
$R_9$ and $R_{10}$ are the same as or different from each other, and are each independently hydrogen; deuterium; a halogen group; a cyano group; a substituted or unsubstituted alkyl group; or a substituted or unsubstituted aryl group,
p and q are an integer of 1 to 4,
when p is 2 or more, a plurality of $R_9$'s is the same as or different from each other, and
when q is 2 or more, a plurality of $R_{10}$'s is the same as or different from each other.

2. The compound of claim 1, wherein $L_1$ to $L_3$ are the same as or different from each other, or and are each independently a direct bond, a substituted or unsubstituted phenylene group, a substituted or unsubstituted biphenylene group, a substituted or unsubstituted terphenylene group, a substituted or unsubstituted naphthylene group, a substituted or unsubstituted anthracenylene group, a substituted or unsubstituted phenanthrylene group, a substituted or unsubstituted triphenylene group, or a substituted or unsubstituted fluorenylene group.

3. The compound of claim 1, wherein $Ar_1$ and $Ar_2$ are the same as or different from each other, and are each independently a substituted or unsubstituted phenyl group, a substituted or unsubstituted biphenyl group, a substituted or unsubstituted terphenyl group, a substituted or unsubstituted naphthyl group, a substituted or unsubstituted anthracenyl group, a substituted or unsubstituted phenanthryl group, a substituted or unsubstituted triphenyl group, or a substituted or unsubstituted fluorenyl group.

4. The compound of claim 1, wherein $R_1$ and $R_2$, $R_2$ and $R_3$, or $R_3$ and $R_4$ combine with each other to form a substituted or unsubstituted aromatic hydrocarbon ring.

5. The compound of claim 1, wherein Chemical Formula 1 is represented by any one of the following Chemical Formulae 2 to 4:

[Chemical Formula 2]

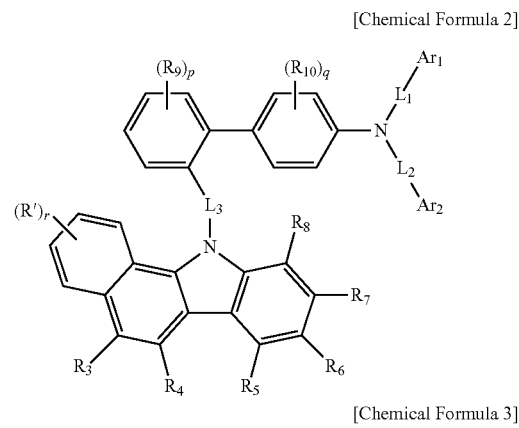

[Chemical Formula 3]

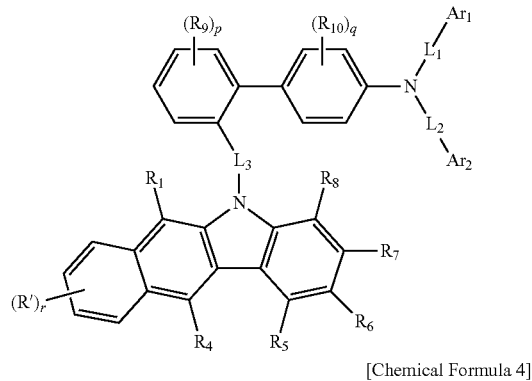

[Chemical Formula 4]

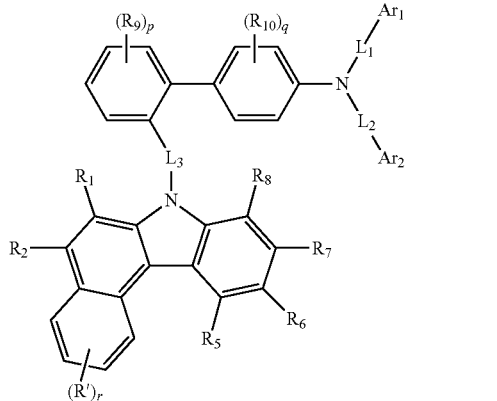

in Chemical Formulae 2 to 4,
$L_1$ to $L_3$, $Ar_1$, $Ar_2$, $R_1$ to $R_{10}$, p, and q are the same as those defined in Chemical Formula 1,
R' is hydrogen; deuterium; a halogen group; a cyano group; a substituted or unsubstituted alkyl group; or a substituted or unsubstituted aryl group,
r is an integer of 1 to 4, and
when r is 2 or more, a plurality of R's is the same as or different from each other.

6. The compound of claim 1, wherein $R_9$ and $R_{10}$ are hydrogen.
7. The compound of claim 1, wherein the compound represented by Chemical Formula 1 is any one selected from the following compounds:
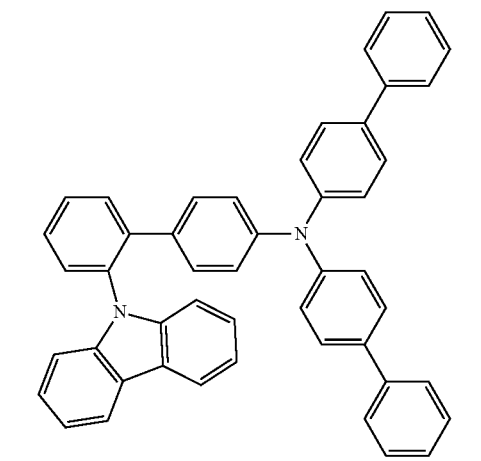
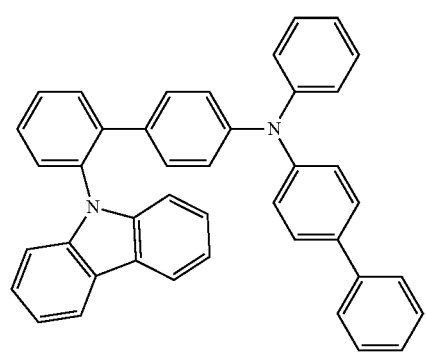
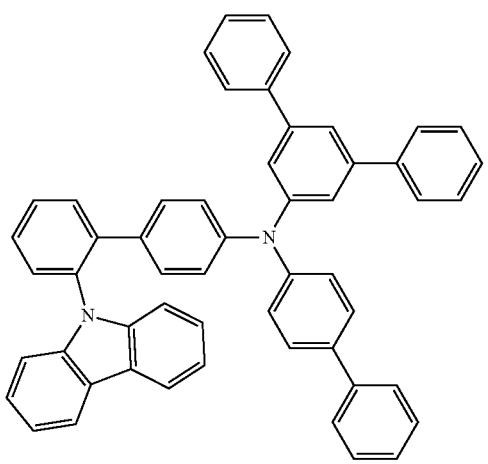
-continued
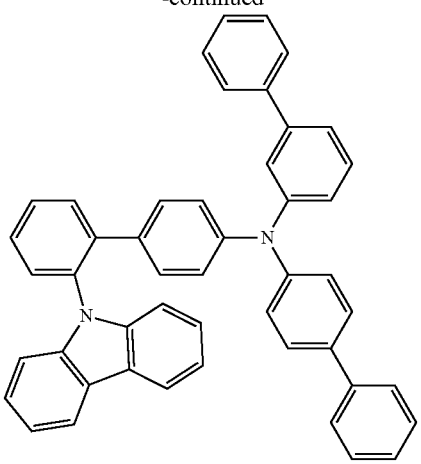
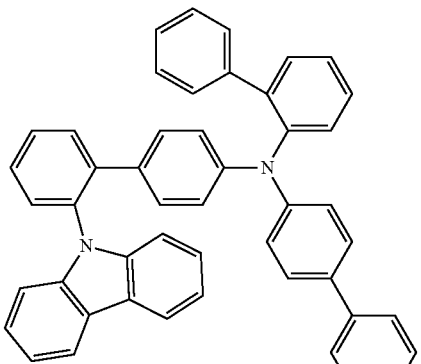
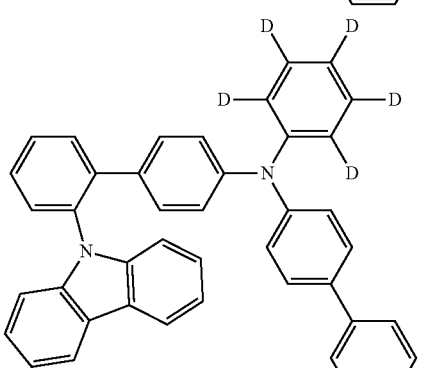
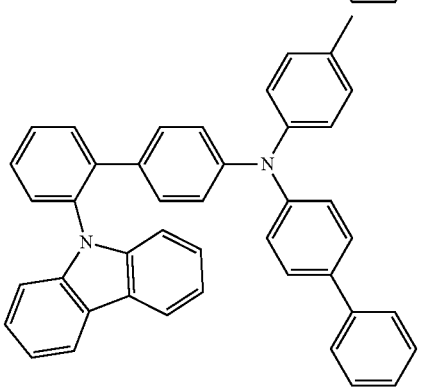

109
-continued
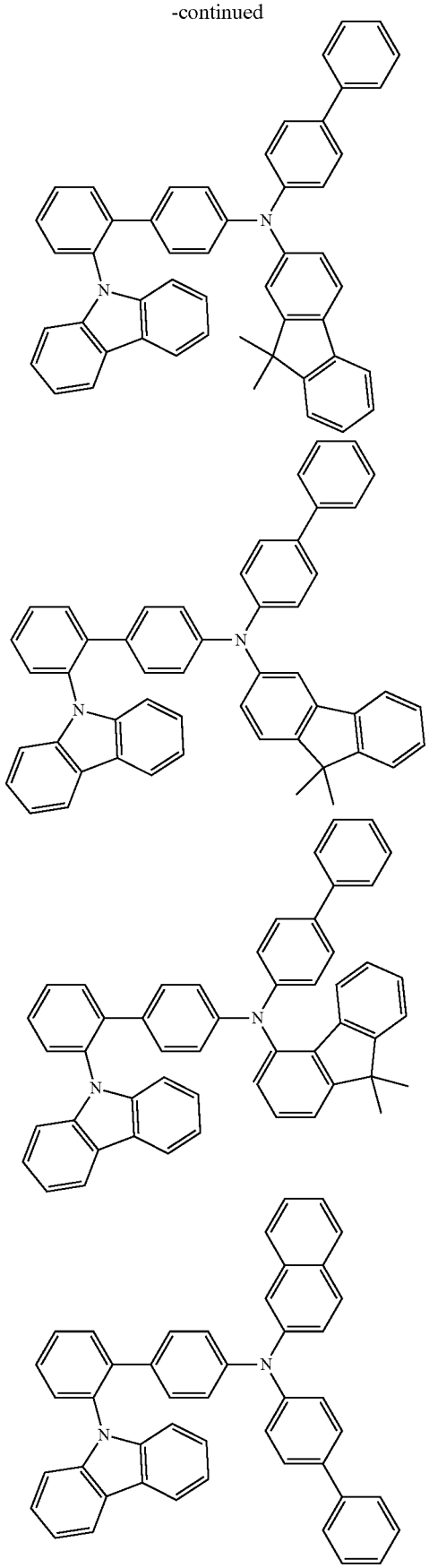
110
-continued
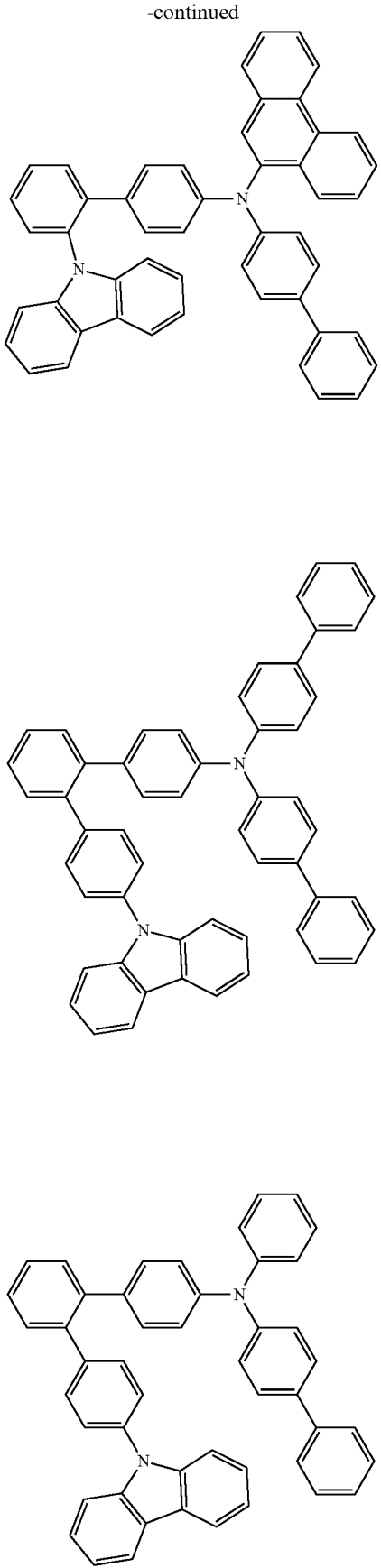

111
-continued
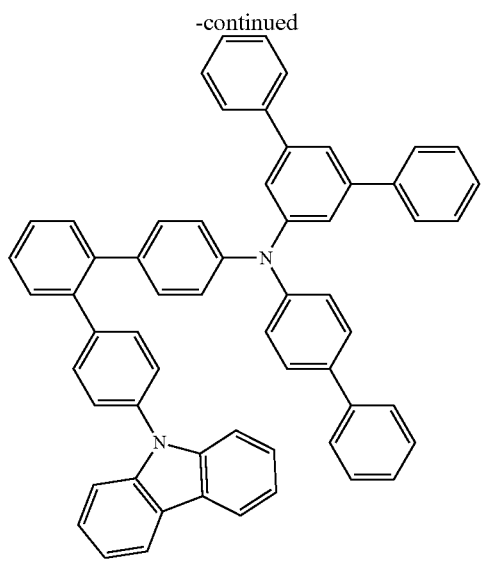
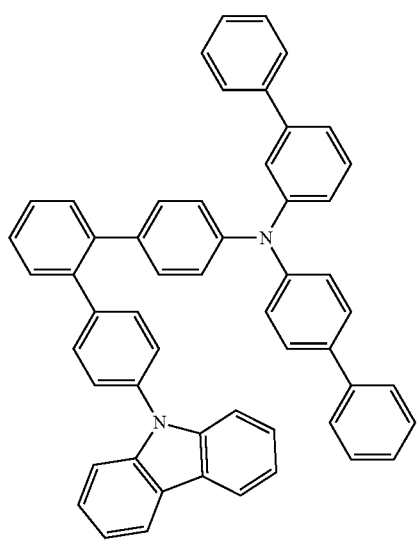
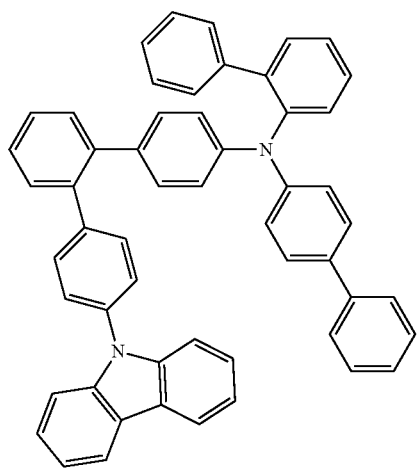
112
-continued
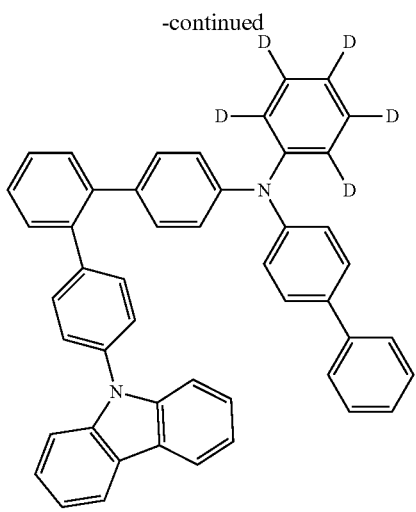
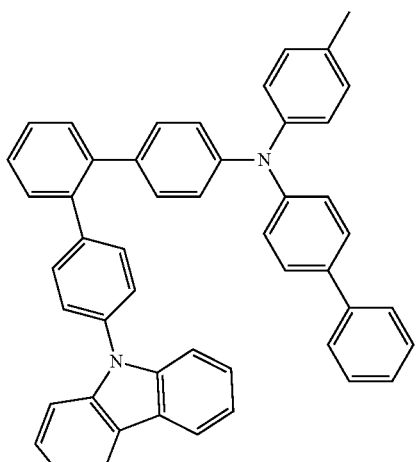
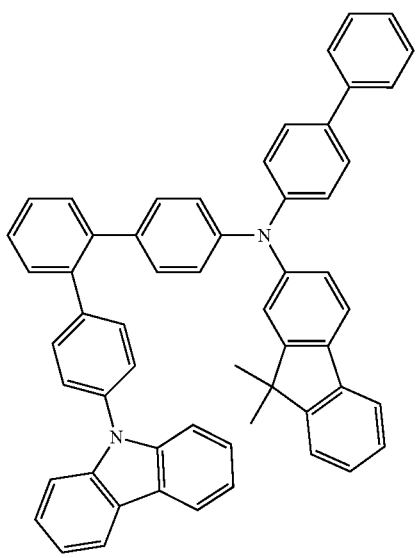

113
-continued
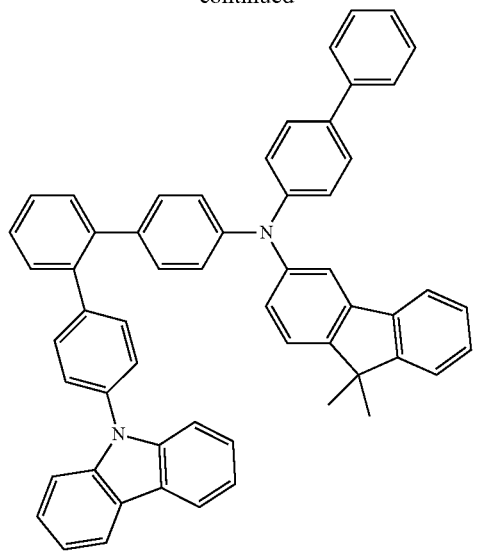
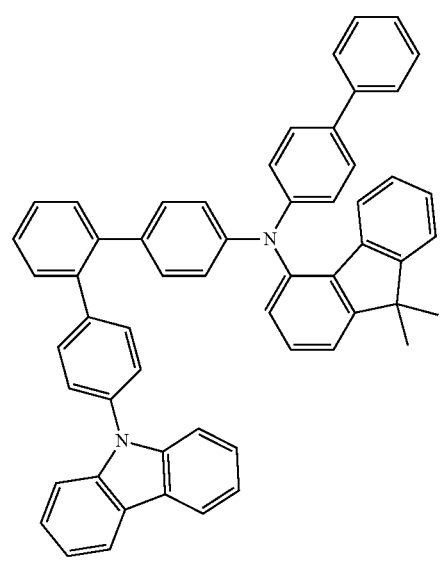
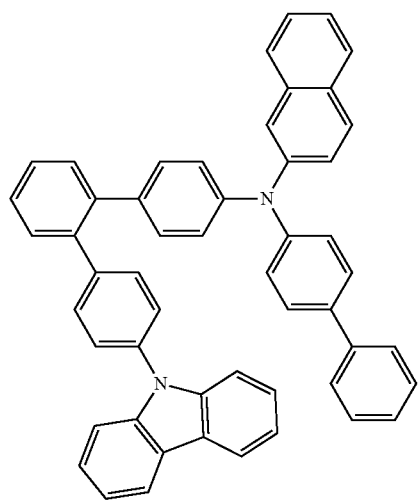
114
-continued
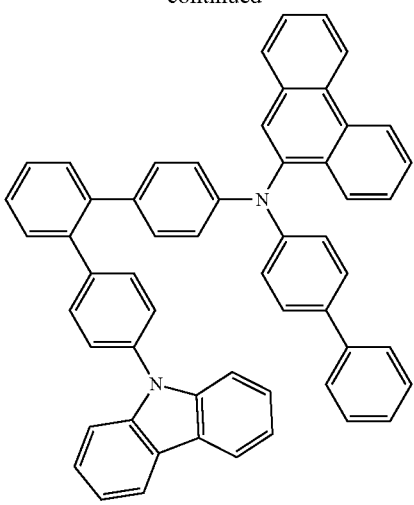
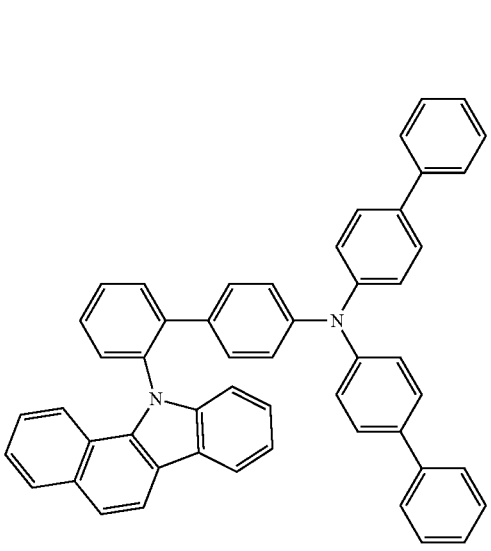
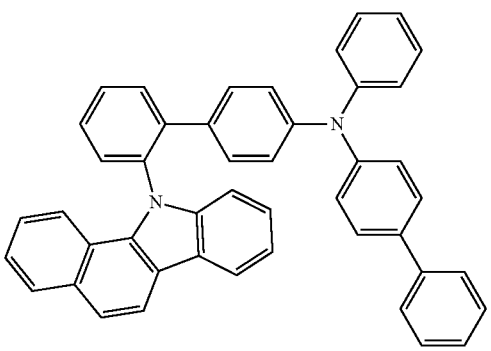

115
-continued
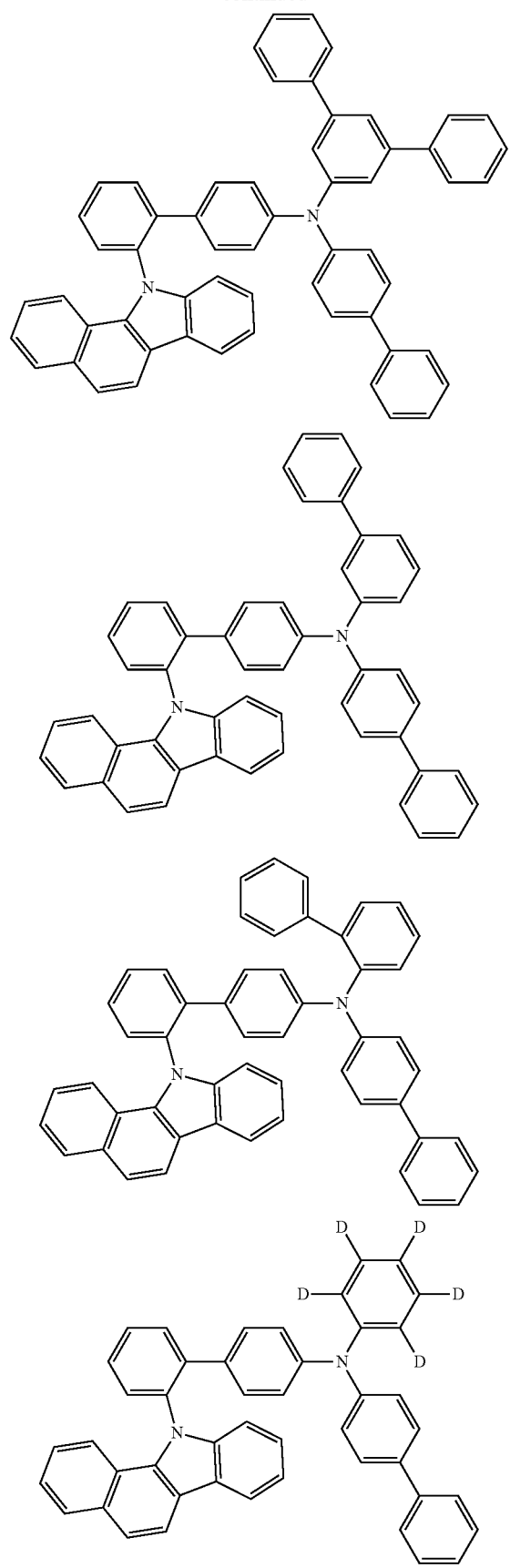
116
-continued
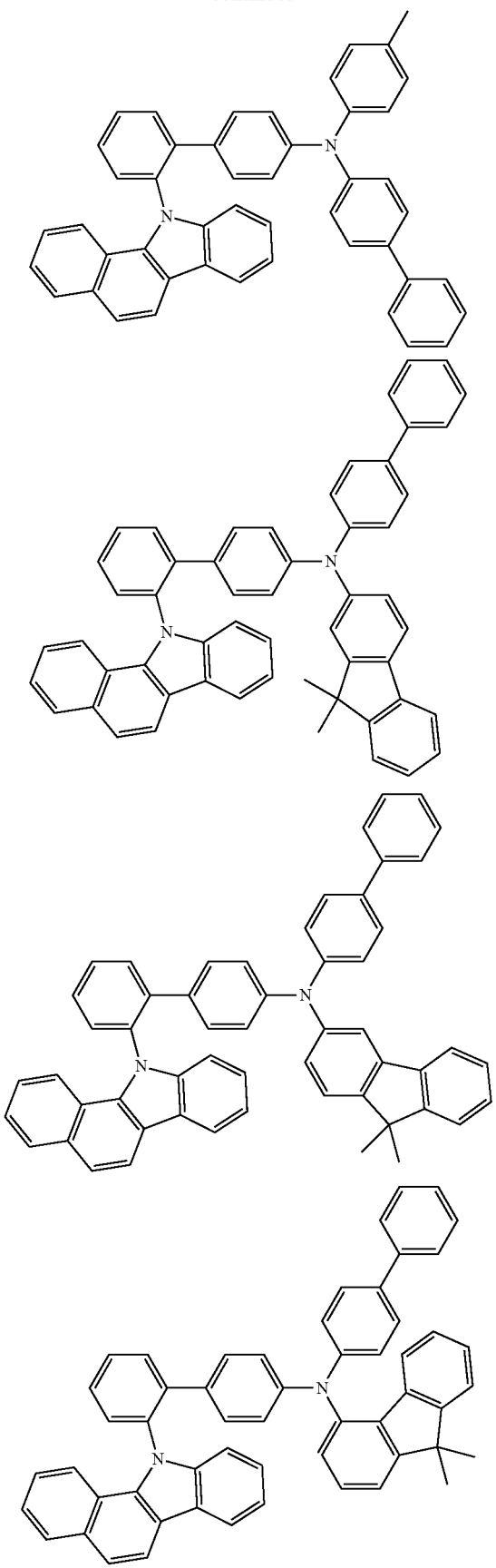

117
-continued
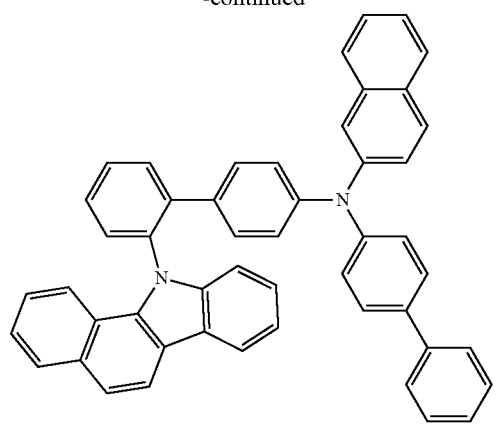
118
-continued
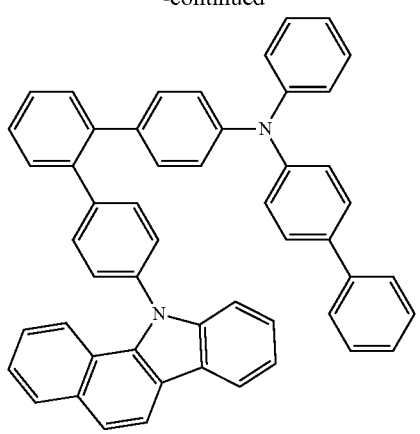
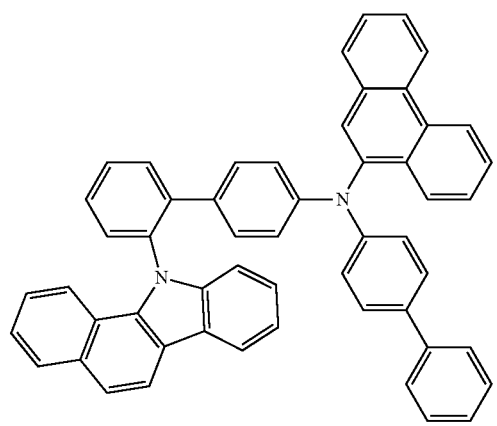
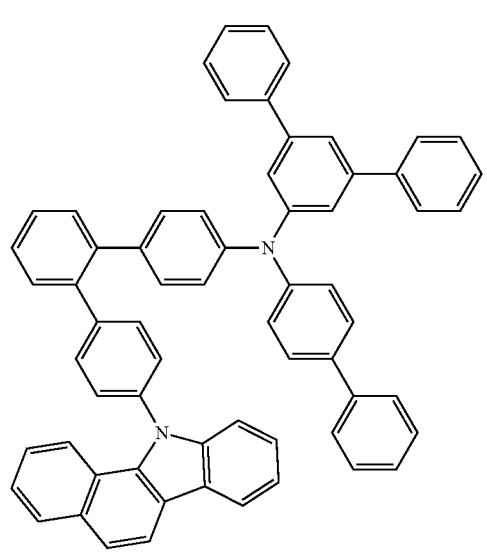
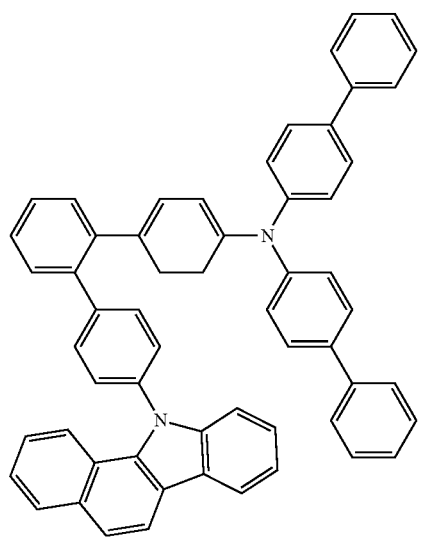
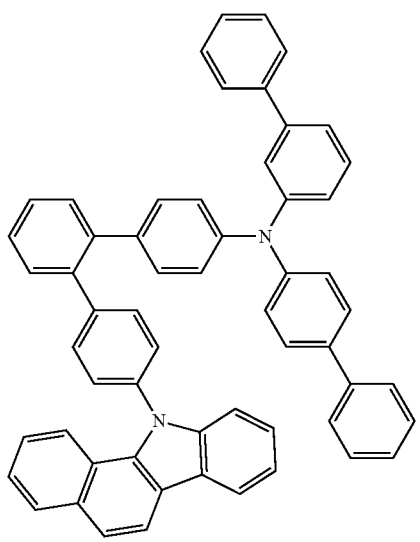

119
-continued
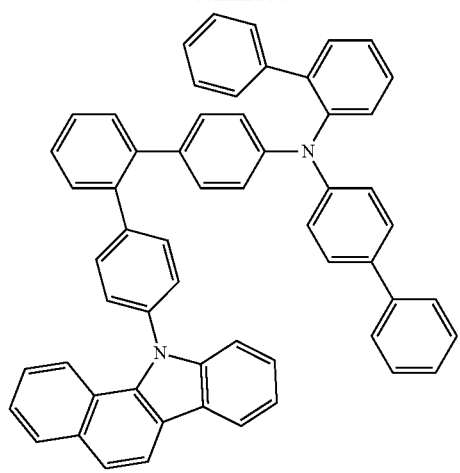
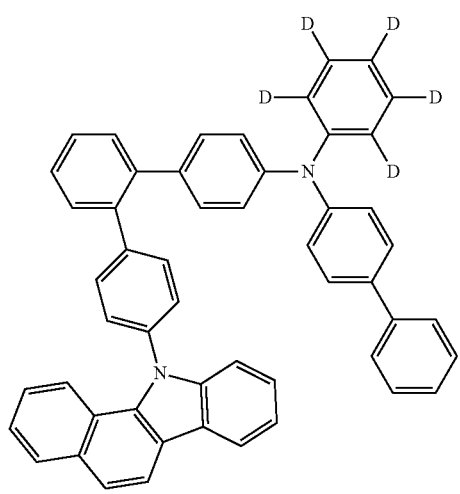
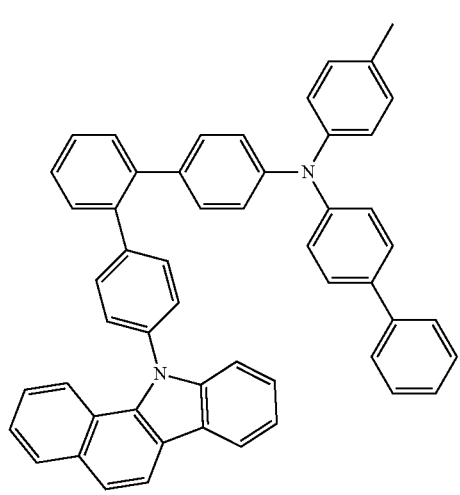
120
-continued
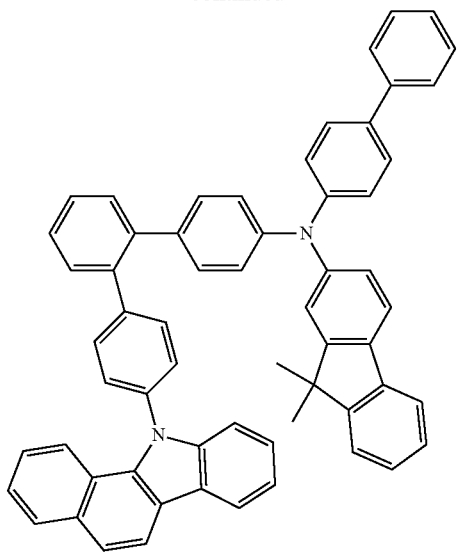
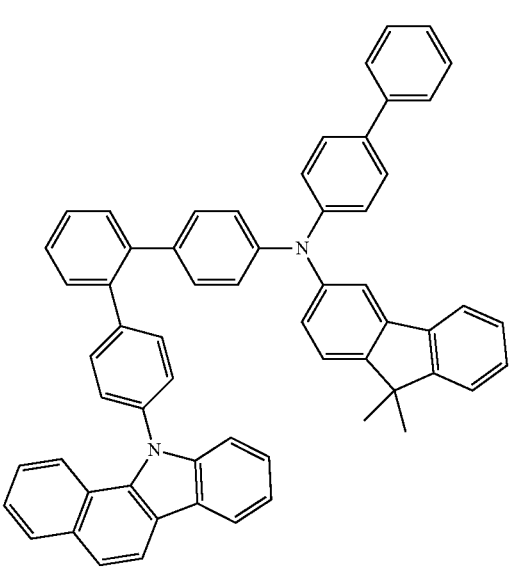
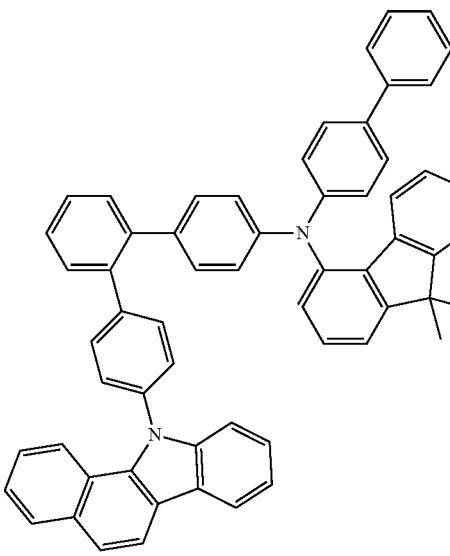

121
-continued
122
-continued
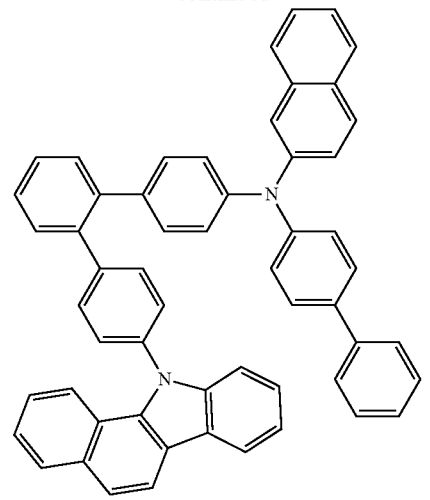
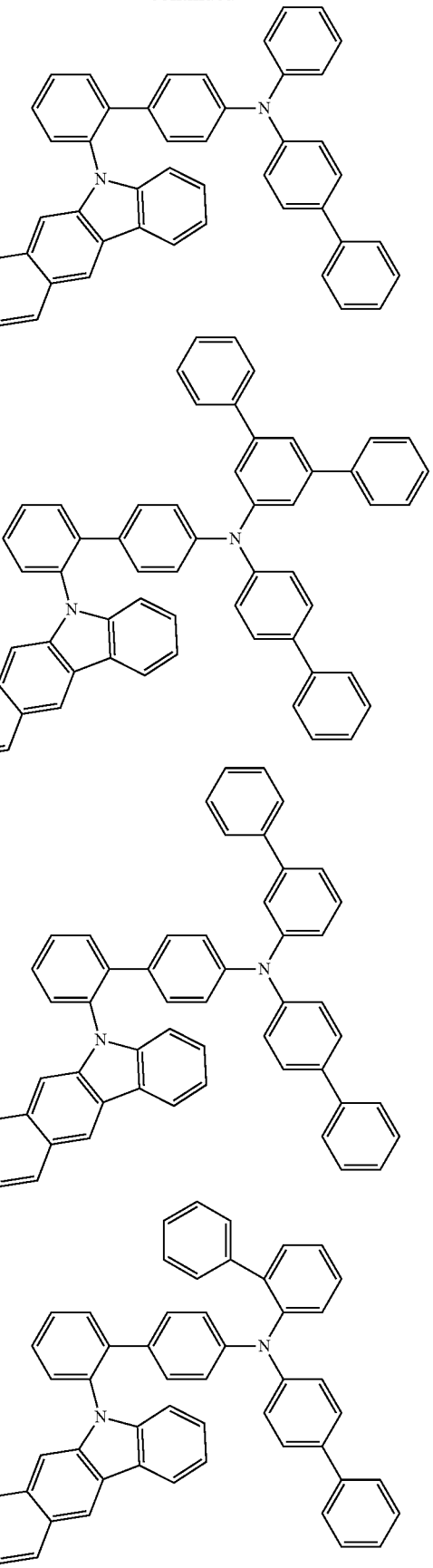

123
-continued
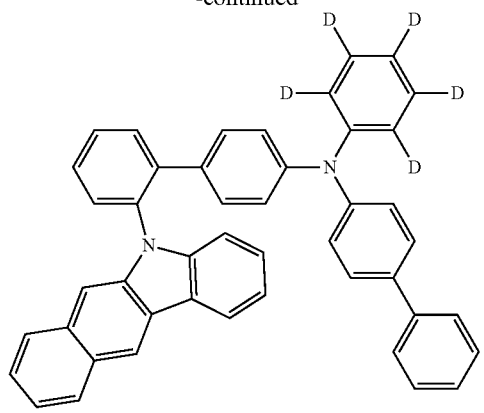
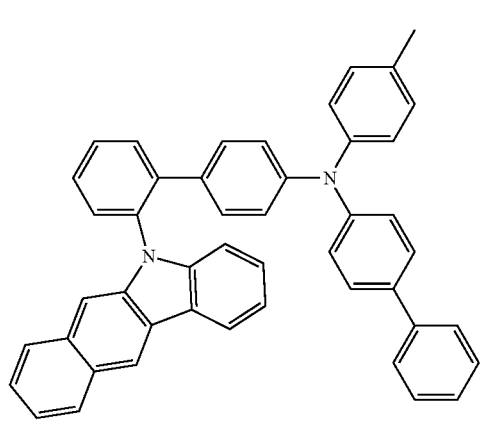
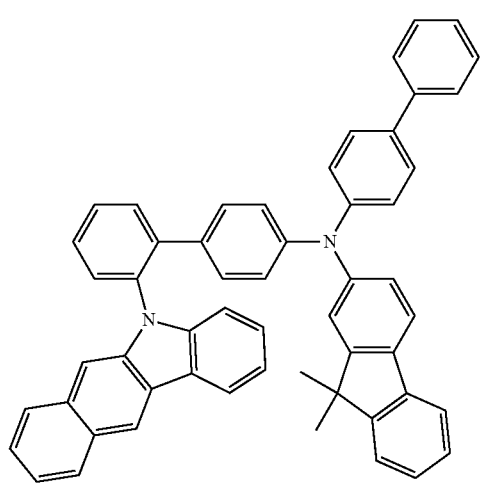
124
-continued
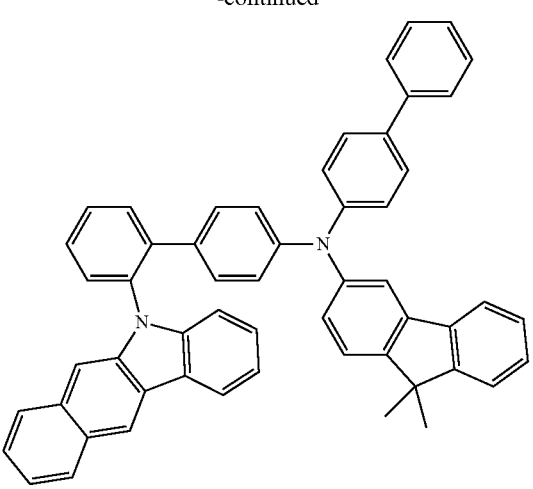
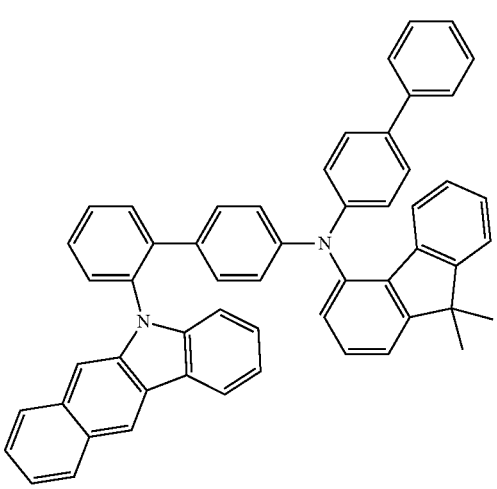
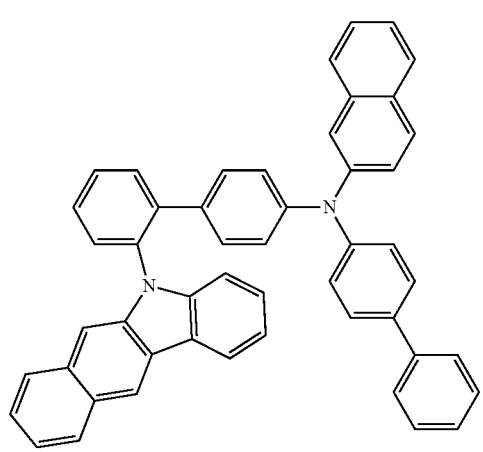

125
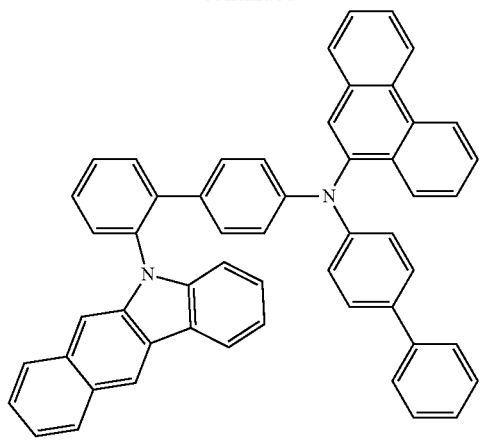
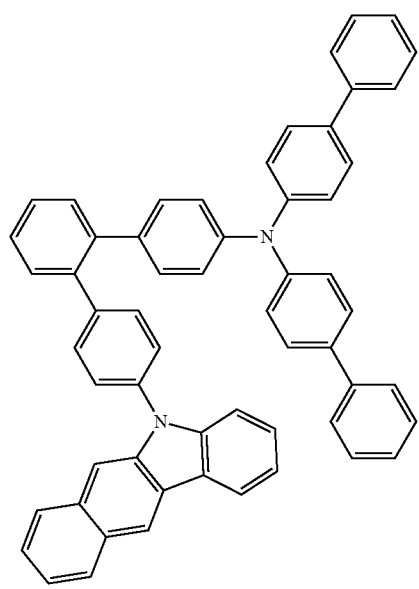
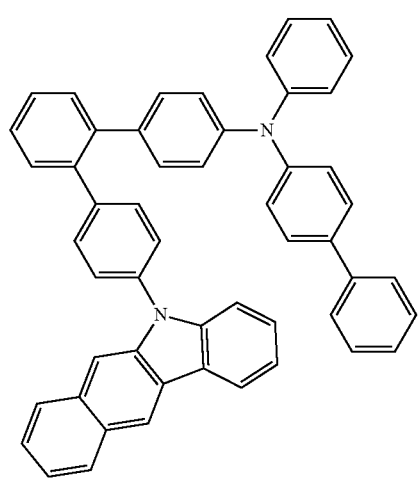
126
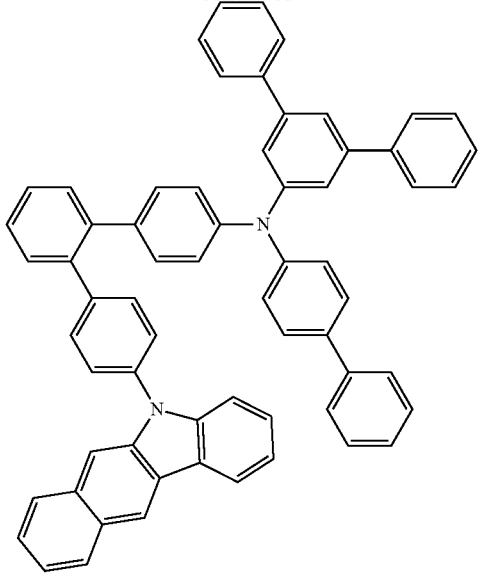
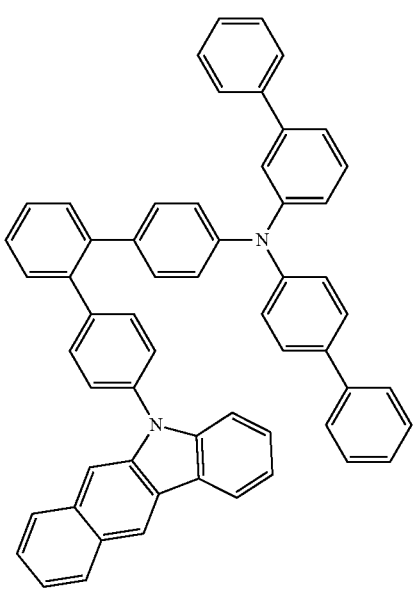
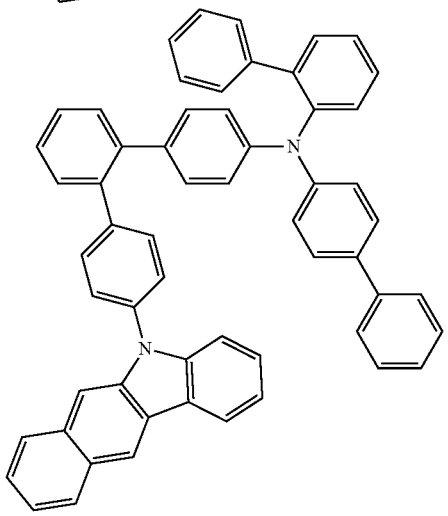

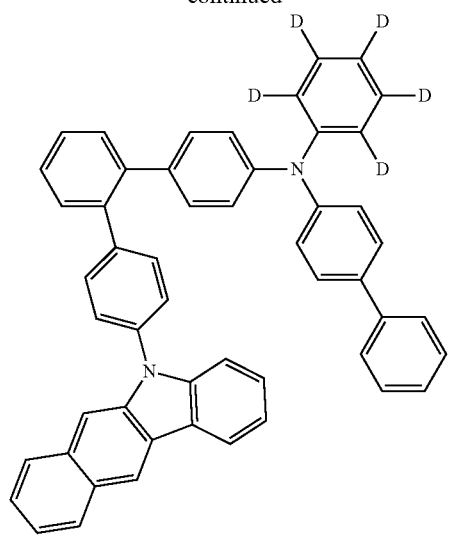
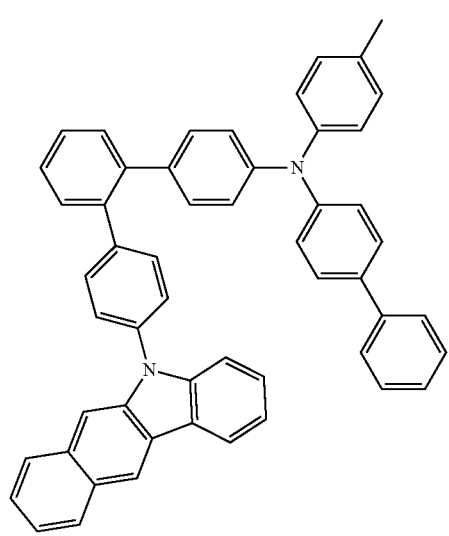
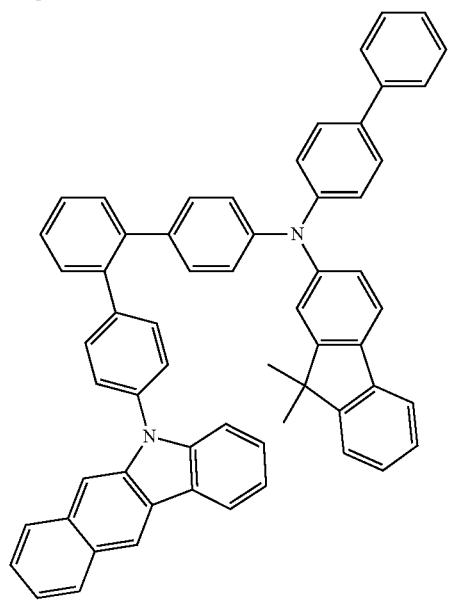
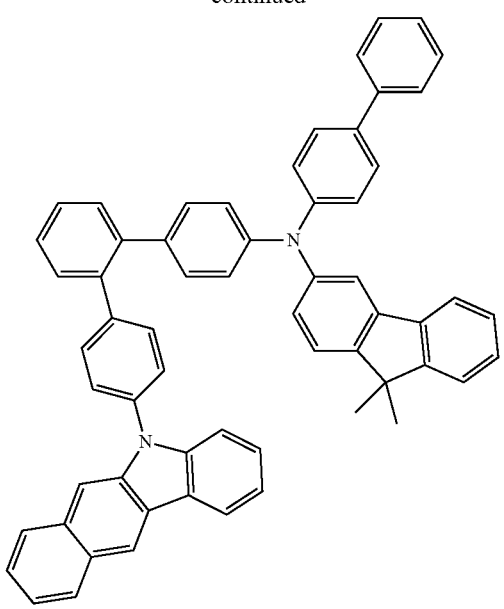
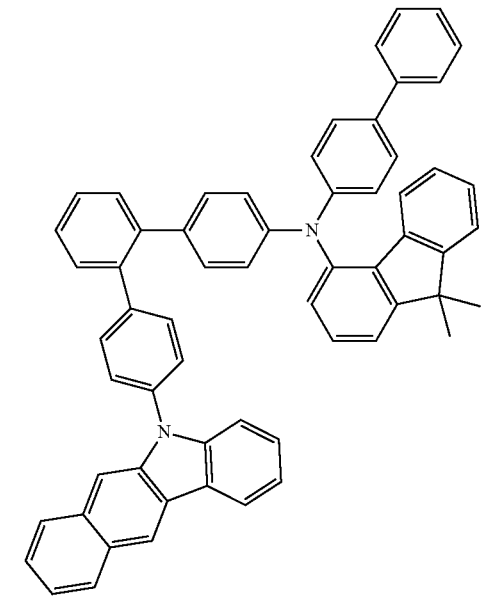

129
-continued
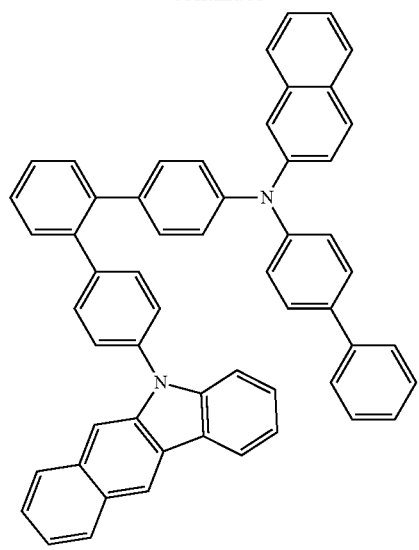
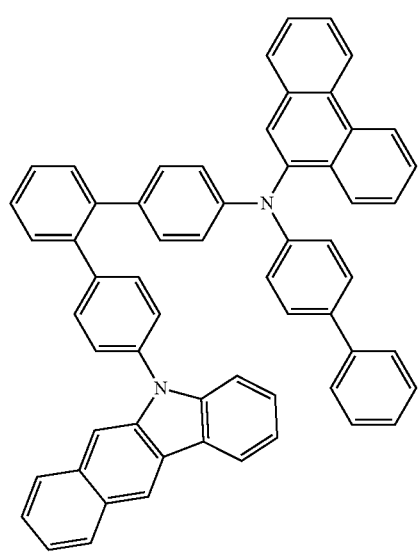
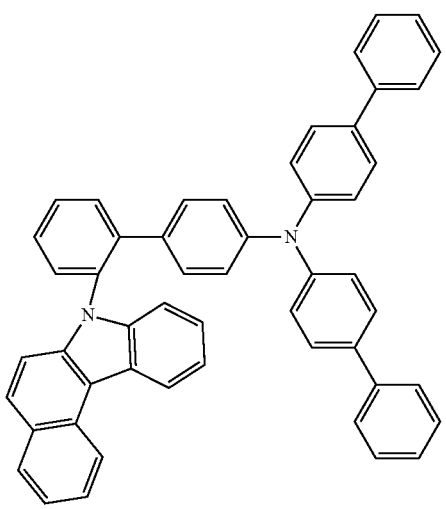
130
-continued
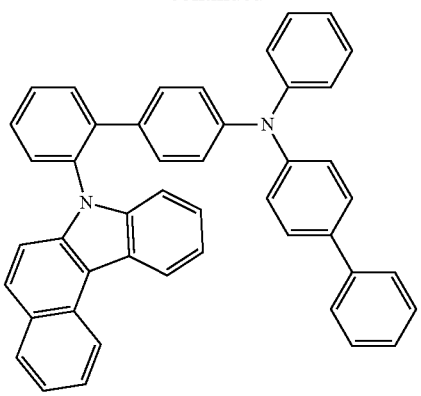
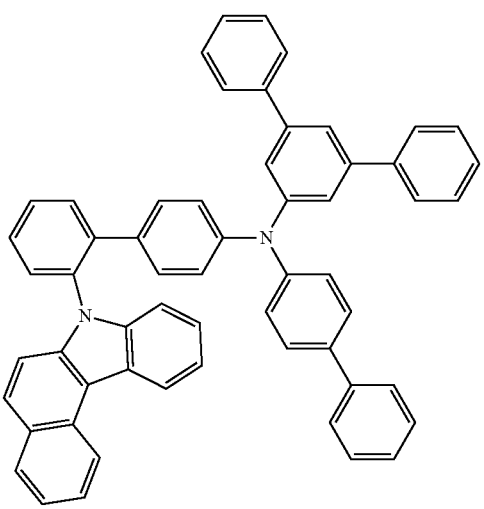
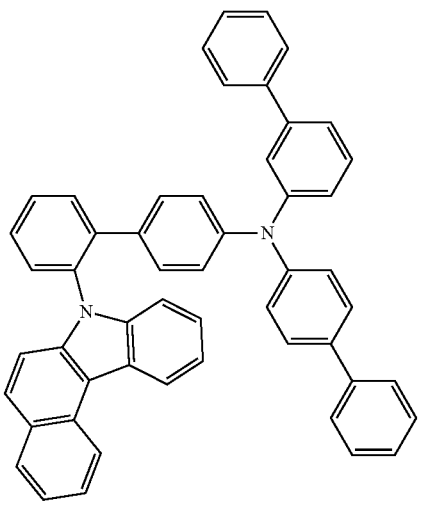

131
-continued
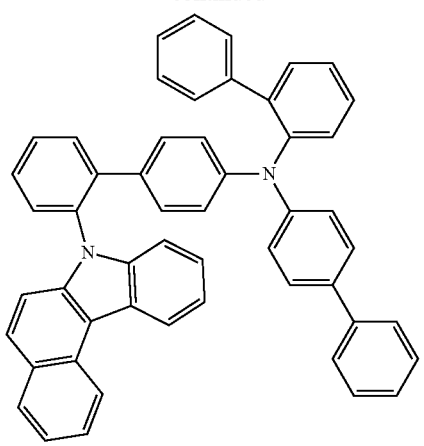
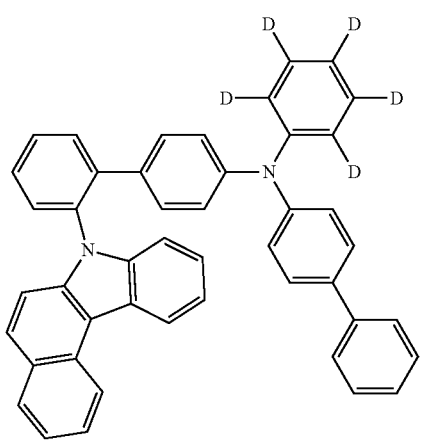
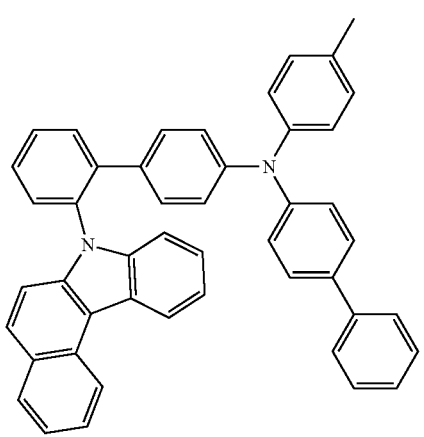
132
-continued
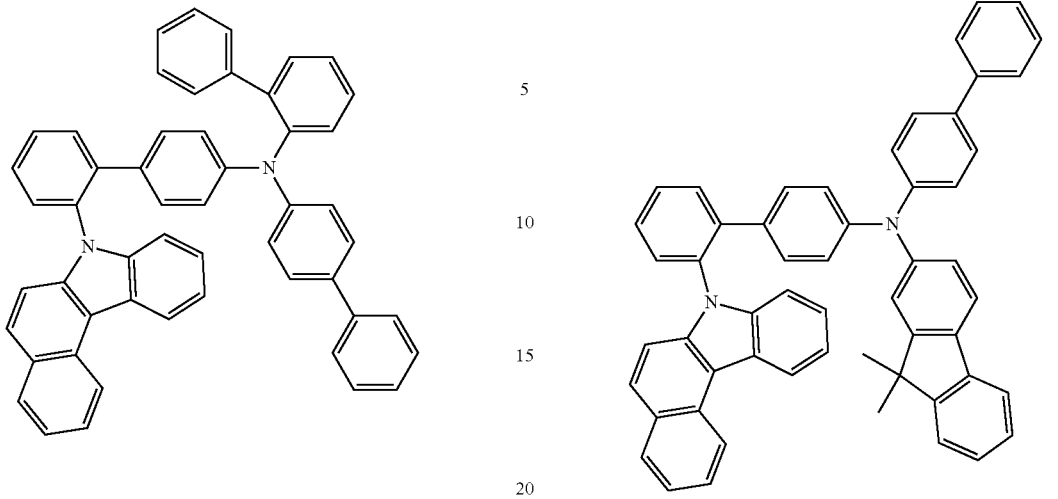
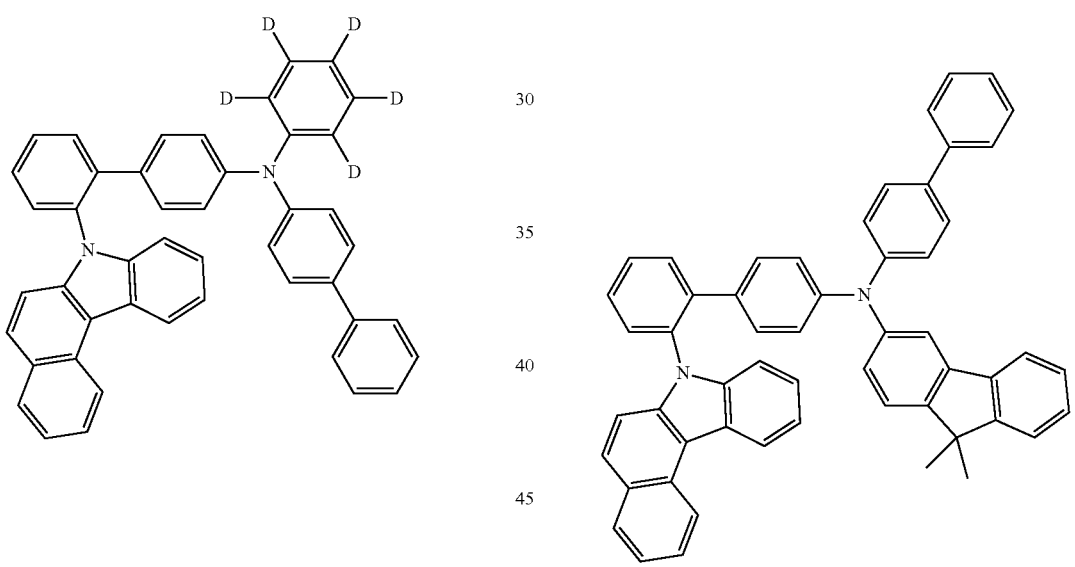
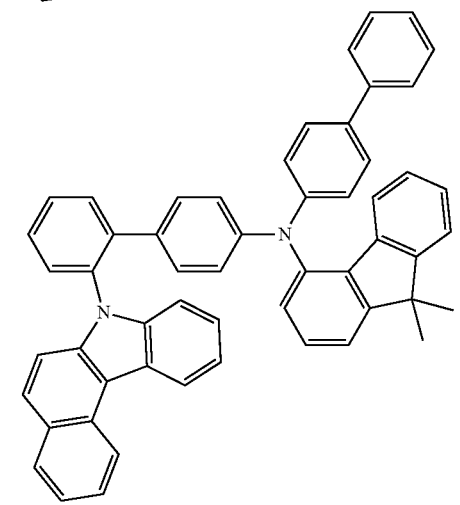

133
-continued
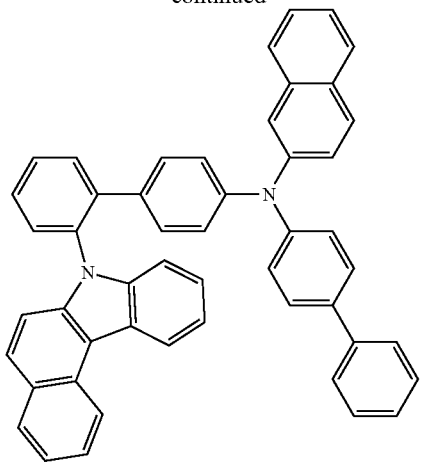
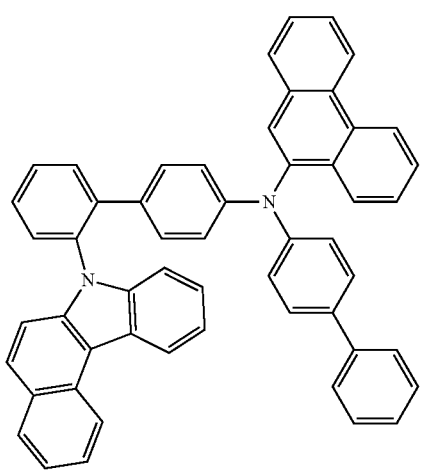
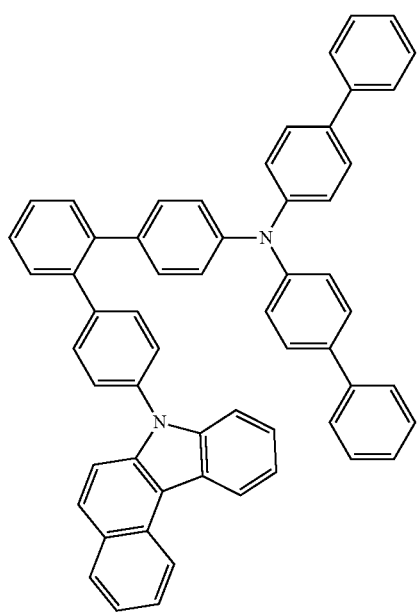
134
-continued
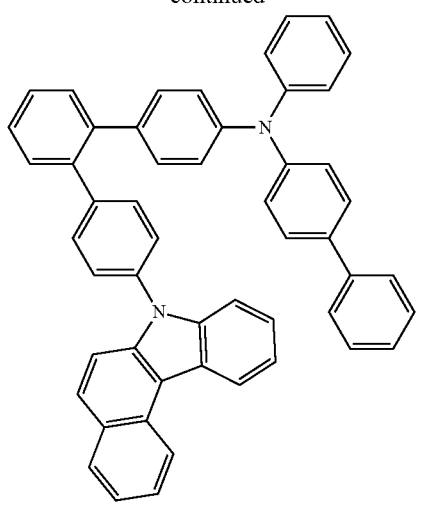
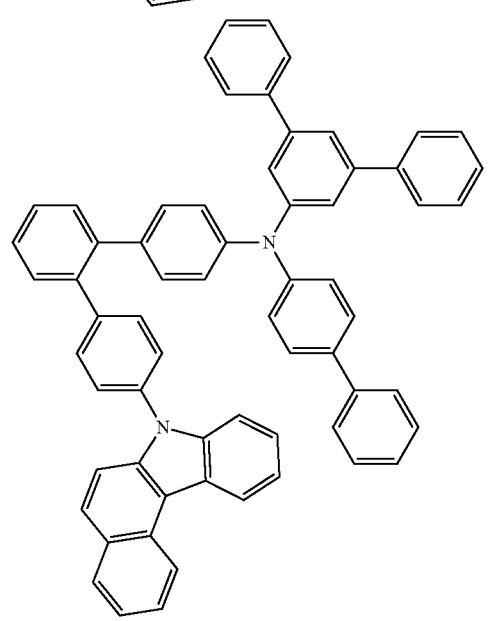
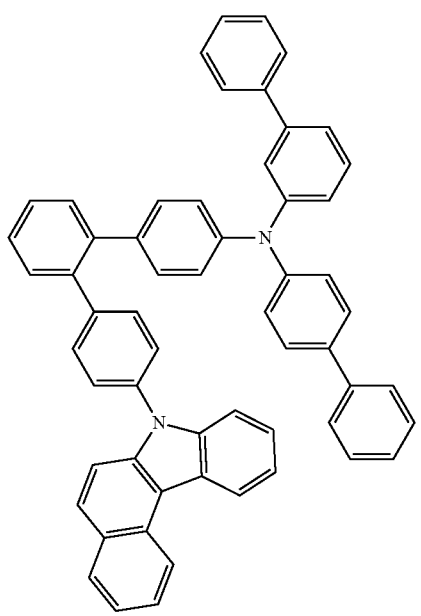

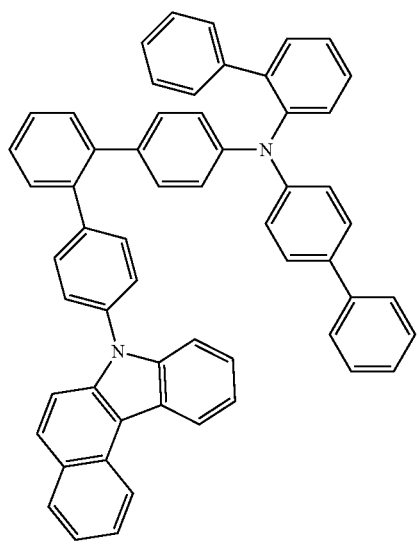
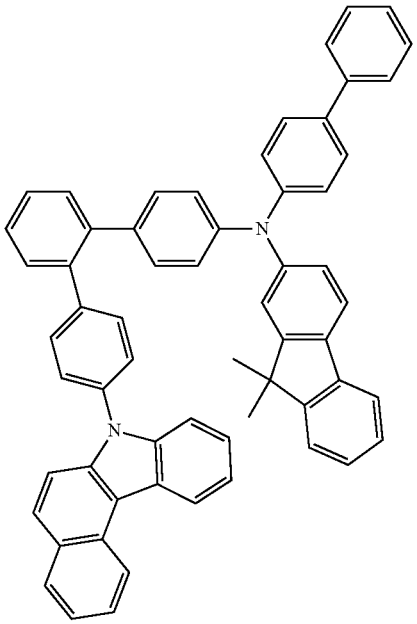
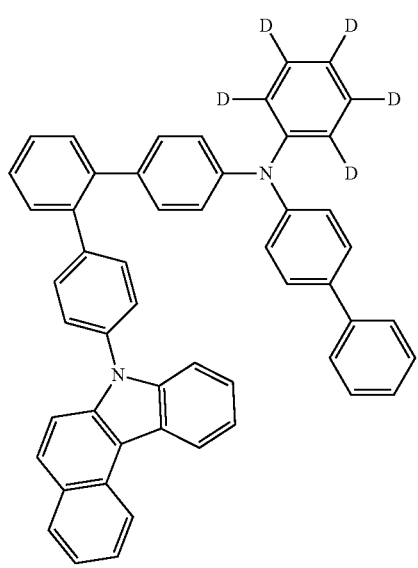
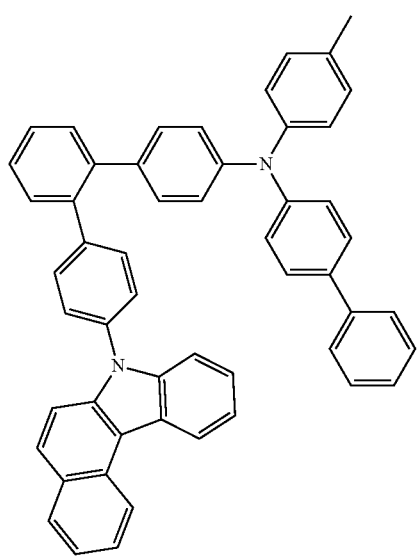
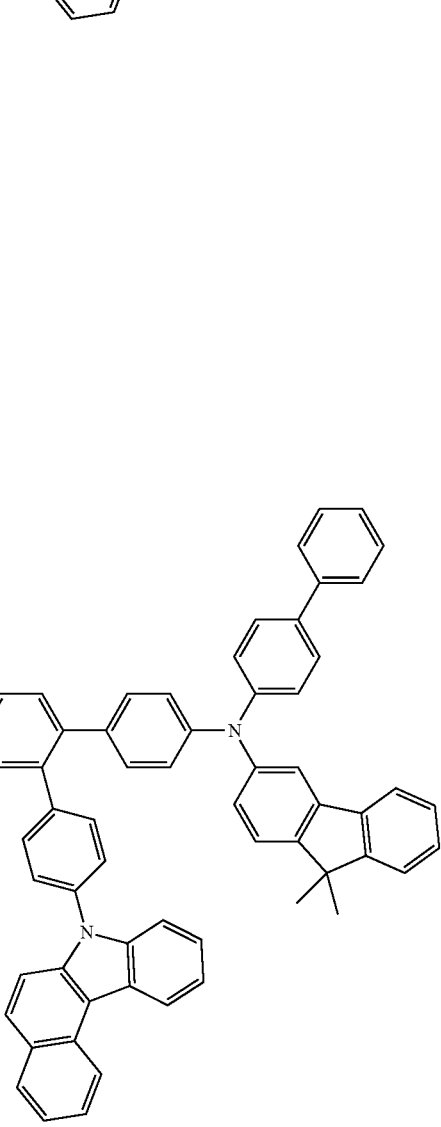

137
-continued
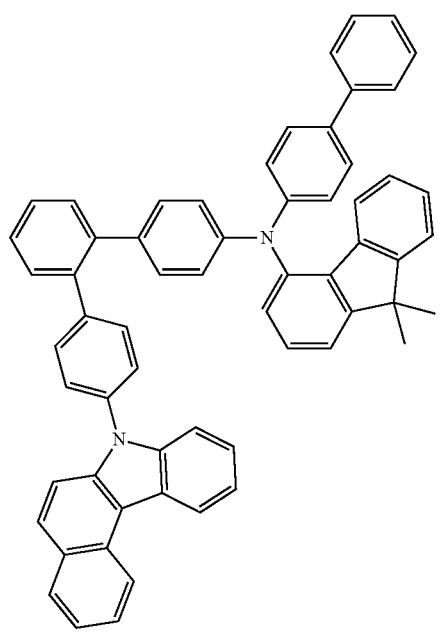
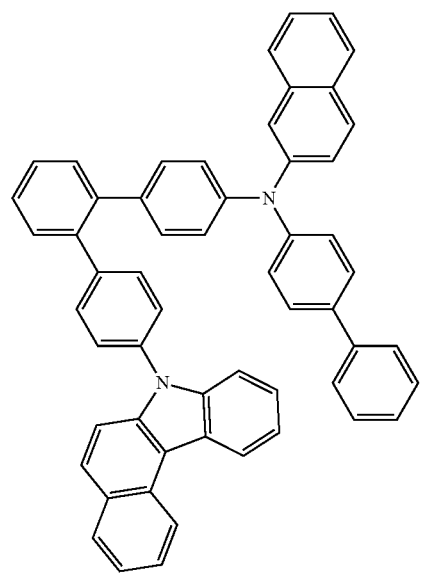
138
-continued
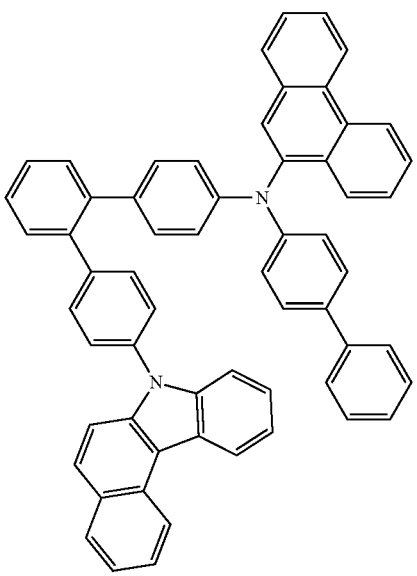
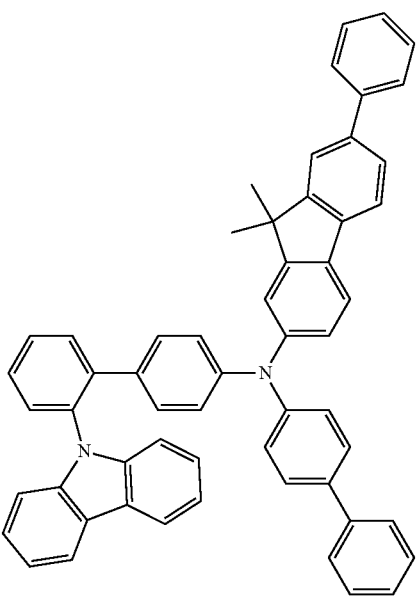

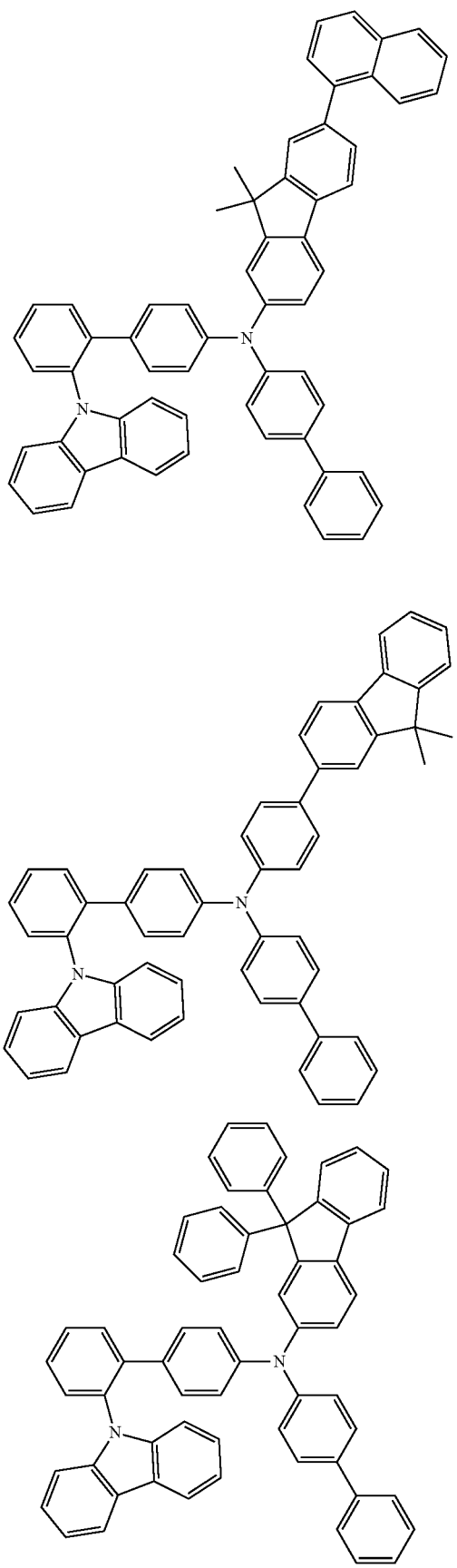
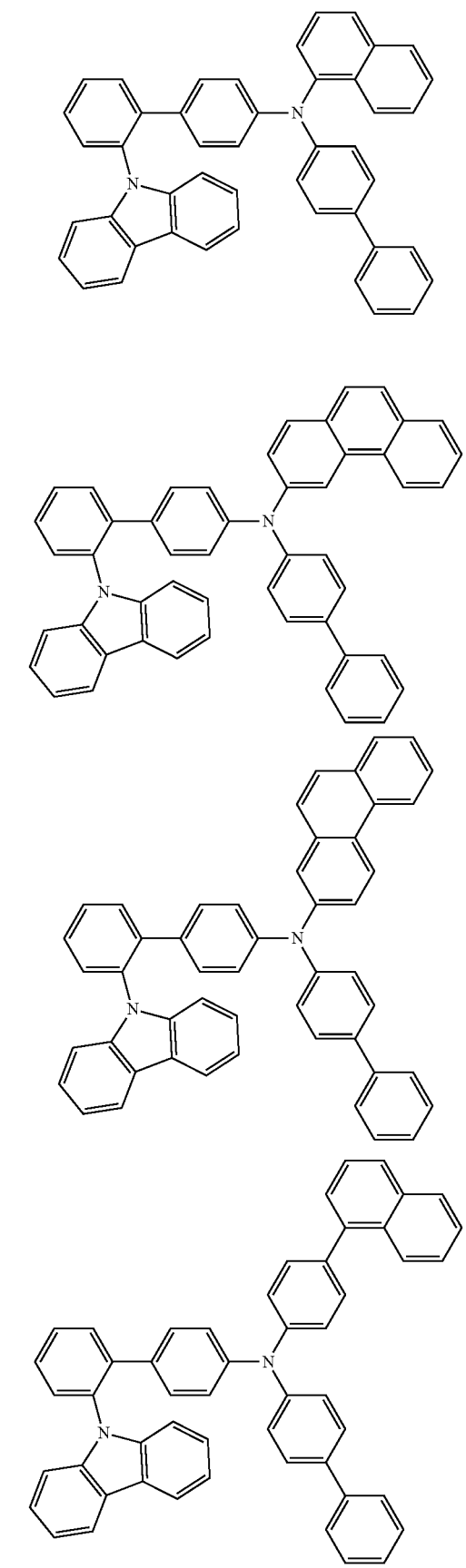

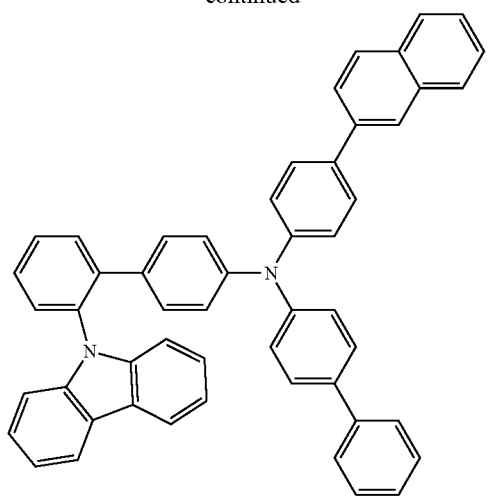
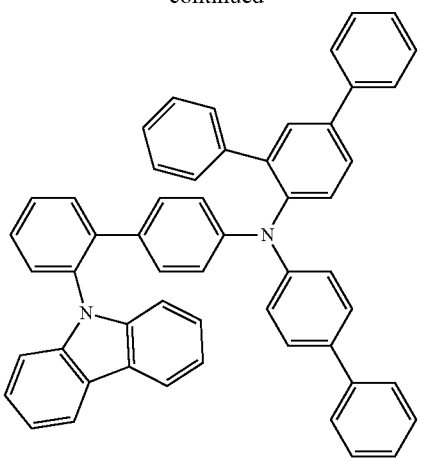
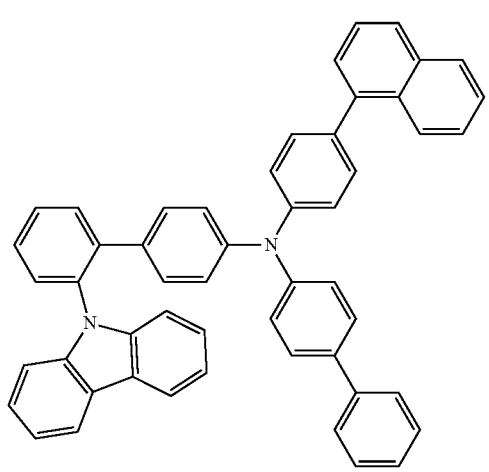
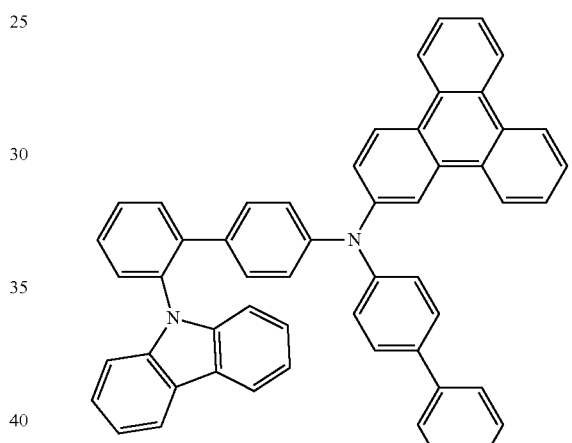
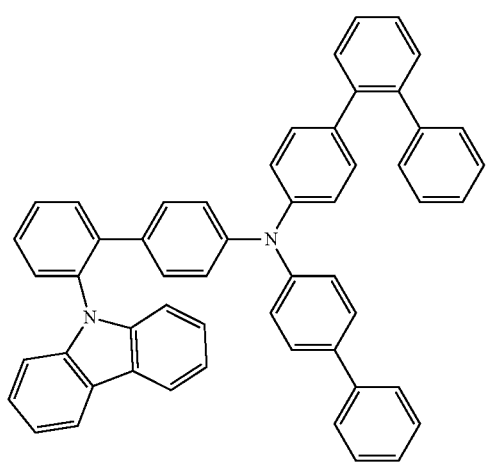
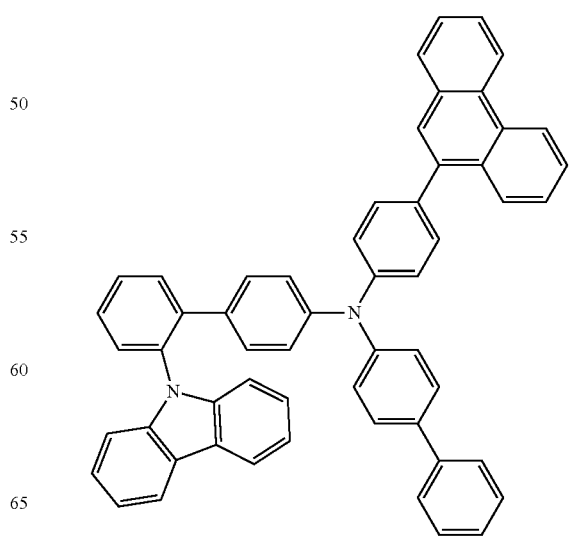

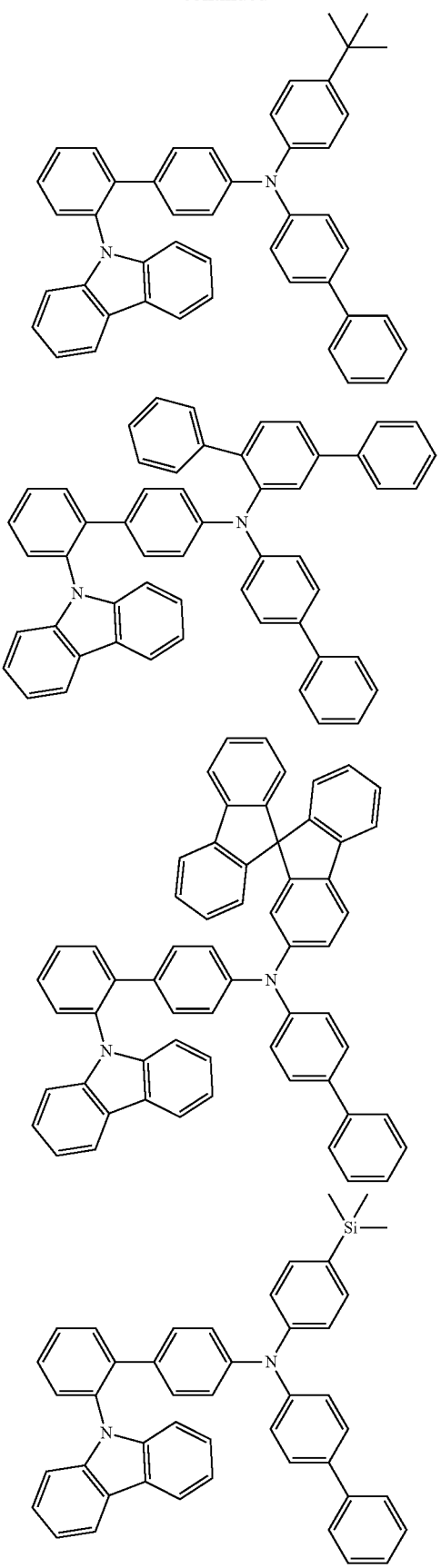

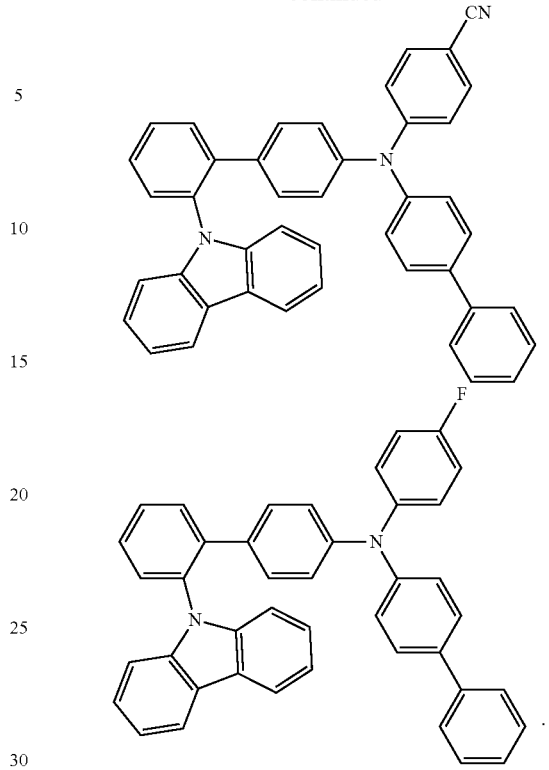

8. An organic electronic device comprising:
a first electrode;
a second electrode provided to face the first electrode; and
one or more organic material layers provided between the first electrode and the second electrode,
wherein one or more layers of the organic material layers comprise the compound of claim 1.

9. The organic electronic device of claim 8, wherein the organic material layer comprises a hole injection layer or a hole transport layer, and the hole injection layer or the hole transport layer comprises the compound.

10. The organic electronic device of claim 8, wherein the organic material layer comprises an electron blocking layer, and the electron blocking layer comprises the compound.

11. The organic electronic device of claim 8, further comprising:
one or two or more layers selected from a group consisting of a hole injection layer, a hole transport layer, and an electron blocking layer.

12. The organic electronic device of claim 8, wherein the organic electronic device is selected from a group consisting of an organic light emitting device, an organic phosphorescent device, an organic solar cell, an organic photoconductor (OPC), and an organic transistor.

13. The organic electronic device of claim 8, wherein the organic material layer comprises a light emitting layer, and the light emitting layer comprises a compound represented by the following Chemical Formula 1-A:

[Chemical Formula 1-A]

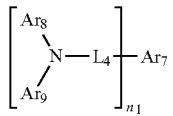

in Chemical Formula 1-A, $n_1$ is an integer of 1 or more, $Ar_7$ is a substituted or unsubstituted monovalent or more benzofluorene group; a substituted or unsubstituted monovalent or more fluoranthene group; a substituted or unsubstituted monovalent or more pyrene group; or a substituted or unsubstituted monovalent or more chrysene group, $L_4$ is a direct bond; a substituted or unsubstituted arylene group; or a substituted or unsubstituted heteroarylene group, $Ar_8$ and $Ar_9$ are the same as or different from each other, and are each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or optionally combine with each other to form a substituted or unsubstituted ring, and when $n_1$ is 2 or more, each of

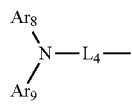

is the same as or different from each other.

14. The organic electronic device of claim 13, wherein $L_4$ is a direct bond, Ar7 is a divalent pyrene group, $Ar_8$ and $Ar_9$ are the same as or different from each other, and are each independently an aryl group which is unsubstituted or substituted with a germanium group substituted with an alkyl group, and $n_1$ is 2.

15. The organic electronic device of claim 8, wherein the organic material layer comprises a light emitting layer, and the light emitting layer comprises a compound represented by the following Chemical Formula 2-A:

[Chemical Formula 2-A]

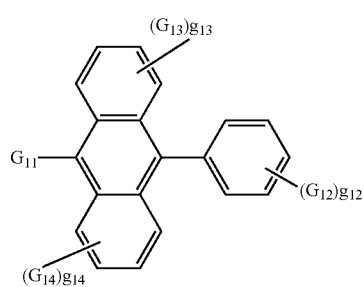

in Chemical Formula 2-A, $G_{11}$ is a 1-naphthyl group, a 2-naphthyl group, a 1-anthracenyl group, a 2-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

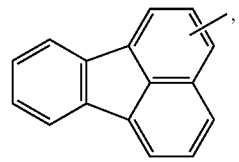

$G_{12}$ is a phenyl group, a 1-naphthyl group, a 2-naphthyl group, a 1-anthracenyl group, a 2-anthracenyl group, a 9-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthracenyl group, a 4'-methylbiphenylyl group, a 4''-t-butyl-p-terphenyl-4-yl group, or a 3-fluoranthenyl group, $G_{13}$ and $G_{14}$ are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, $g_{12}$ is an integer of 1 to 5, $g_{13}$ and $g_{14}$ are each an integer of 1 to 4, and when $g_{12}$ to $g_{14}$ are each 2 or more, G12s to G14s are each independently the same as or different from each other.

16. The organic electronic device of claim 15, wherein $G_{11}$ is a 1-naphthyl group, and $G_{12}$ is a 2-naphthyl group.

17. The organic electronic device of claim 13, wherein the light emitting layer comprises a compound represented by the following Chemical Formula 2-A:

[Chemical Formula 2-A]

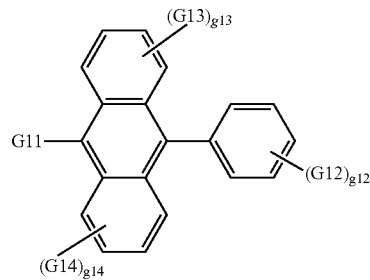

in Chemical Formula 2-A, $G_{11}$ is a phenyl group, a 1-naphthyl group, a 2-naphthyl group, a 1-anthracenyl group, a 2-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following Chemical Formula

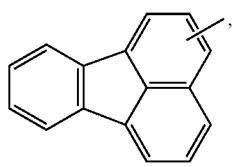

G$_{12}$ is a phenyl group, a 1-naphthyl group, a 2-naphthyl group, a 1-anthracenyl group, a 2-anthracenyl group, a 9-anthracenyl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthracenyl group, a 4'-methylbiphenylyl group, a 4"-t-butyl-p-terphenyl-4-yl group, or a 3-fluoranthenyl group, G$_{13}$ and G$_{14}$ are the same as or different from each other, and are each independently hydrogen; a substituted or unsubstituted alkyl group; a substituted or unsubstituted alkoxy group; a substituted or unsubstituted aryl group; or a substituted or unsubstituted heteroaryl group, g$_{12}$ is an integer of 1 to 5, g$_{13}$ and g$_{14}$ are each an integer of 1 to 4, and when g$_{12}$ to g$_{14}$ are each 2 or more, G$_{12}$s to G14s are each independently the same as or different from each other.

* * * * *